(12) United States Patent
Friedland et al.

(10) Patent No.: US 11,390,861 B2
(45) Date of Patent: Jul. 19, 2022

(54) CRISPR/CAS-RELATED METHODS AND COMPOSITIONS FOR TREATING HERPES SIMPLEX VIRUS

(71) Applicants: EDITAS MEDICINE, INC., Cambridge, MA (US); DUKE UNIVERSITY, Durham, NC (US)

(72) Inventors: Ari E. Friedland, Boston, MA (US); Penrose O'Donnell, Yarmouth, MA (US); David A. Bumcrot, Belmont, MA (US); Bryan R. Cullen, Durham, NC (US)

(73) Assignees: EDITAS MEDICINE, INC., Cambridge, MA (US); DUKE UNIVERSITY, Durham, NC (US)

( * ) Notice: Subject to any disclaimer, the term of this patent is extended or adjusted under 35 U.S.C. 154(b) by 0 days.

(21) Appl. No.: 16/395,833

(22) Filed: Apr. 26, 2019

(65) Prior Publication Data

US 2019/0249157 A1 Aug. 15, 2019

Related U.S. Application Data

(63) Continuation of application No. PCT/US2017/058670, filed on Oct. 27, 2017.

(60) Provisional application No. 62/414,561, filed on Oct. 28, 2016.

(51) Int. Cl.
*C12N 9/22* (2006.01)
*C12N 15/113* (2010.01)
*C12N 15/11* (2006.01)

(52) U.S. Cl.
CPC ............... *C12N 9/22* (2013.01); *C12N 15/11* (2013.01); *C12N 15/1133* (2013.01); *C12N 2310/20* (2017.05)

(58) Field of Classification Search
CPC ...... C12N 9/22; C12N 15/11; C12N 15/1133; C12N 2310/20; A61P 31/22
See application file for complete search history.

(56) References Cited

U.S. PATENT DOCUMENTS

| | | |
|---|---|---|
| 5,443,505 A | 8/1995 | Wong et al. |
| 5,593,972 A | 1/1997 | Weiner et al. |
| 5,766,242 A | 6/1998 | Wong et al. |
| 5,962,428 A | 10/1999 | Carrano et al. |
| 6,251,090 B1 | 6/2001 | Avery et al. |
| 6,299,895 B1 | 10/2001 | Hammang et al. |
| 6,413,540 B1 | 7/2002 | Yaacobi |
| 6,416,777 B1 | 7/2002 | Yaacobi |
| 2018/0251770 A1* | 9/2018 | Friedland ............... C12N 9/22 |

FOREIGN PATENT DOCUMENTS

| | | | |
|---|---|---|---|
| WO | WO 93/24640 | 12/1993 | |
| WO | WO 94/016737 | 8/1994 | |
| WO | WO 00/40089 | 7/2000 | |
| WO | WO 01/28474 | 4/2001 | |
| WO | WO 02/089767 | 11/2002 | |
| WO | WO 2015/126927 | 8/2015 | |
| WO | WO-2015126927 A2 * | 8/2015 | ......... C12N 15/1131 |
| WO | WO 2015/153789 | 10/2015 | |
| WO | WO 2015/153791 | 10/2015 | |
| WO | WO 2017/075475 | 5/2017 | |

OTHER PUBLICATIONS

Bumcrot, D. Vector-delivered CRISPR/Cas as a cure for HSV-1-induced keratitis. Editas Medicine, Inc., Cambridge, MA, USA. Start Date: Jul. 2, 2015. Project#: 1R43A1120302-01. Application #8978393.*
Kennedy EM, Cullen BR. Bacterial CRISPR/Cas DNA endonucleases: A revolutionary technology that could dramatically impact viral research and treatment. Virology. May 2015;479-480:213-20. Epub Mar. 7, 2015.*
Roehm PC, Shekarabi M, Wollebo HS, Bellizzi A, He L, Salkind J, Khalili K. Inhibition of HSV-1 Replication by Gene Editing Strategy. Sci Rep. Apr. 11, 2016,6:23146.*
Van Diemen FR, Kruse EM, Hooykaas MJ, Bruggeling CE, Schurch AC, van Ham PM, Imhof SM, Nijhuis M, Wiertz EJ, Lebbink RJ. CRISPR/Cas9-Mediated Genome Editing of Herpesviruses Limits Productive and Latent Infections. PLoS Pathog. Jun. 30, 2016;12(6):e1005701.*
Ambati et al., "Transscleral Delivery of Bioactive Protein to the Choroid and Retina", Investigative Ophthalmology & Visual Science, 41(5): 1186-1191 (2000).
Ambati et al., "Diffusion of High Molecular Weight Compounds through Sclera", Investigative Ophthalmology & Visual Science, 41(5):1181-1185 (2000).
Banerjee et al., "Immunopathological Aspects of HSV Infection", Human Herpesviruses, Cambridge University Press, Chapter 35, 22 pages (2007).
Bedadala et al., "Early Growth Response Gene 1 (EGR-1) Regulates HSV-1 ICP4 and ICP22 Gene Expression", Cell Research, 17:546-555 (2007).
Belshe et al., "Efficacy Results of a Trial of a Herpes Simplex Vaccine", The New England Journal of Medicine, 366(I):34-43 (2012).
Dawson et al., "Herpes Simplex Eye Infections: Clinical Manifestations, Pathogenesis and Management", Survey of Ophthalmology, 21(2):121-135 (1976).
Farooq et al., "Herpes Simplex Epithelial and Stromal Keratitis: An Epidemiologic Update", Survey of Ophthalmology, 57(5):448-462 (2012).

(Continued)

*Primary Examiner* — Rachel B Gill
(74) *Attorney, Agent, or Firm* — Baker Botts L.L.P.

(57) ABSTRACT

Genome editing systems and genetic constructs that target a herpes simplex virus (HSV) viral gene, where the systems comprise one Cas9 molecule, and a gRNA molecule, compositions and cells comprising such genome editing systems and genetic constructs as well as methods for using the genome editing systems, genetic constructs, compositions and cells for genome engineering, and for preventing, treating or reducing HSV infection.

16 Claims, 1 Drawing Sheet
Specification includes a Sequence Listing.

(56) References Cited

OTHER PUBLICATIONS

Homa et al., "Capsid Assembly and DNA Packaging in Herpes Simplex Virus", Reviews in Medical Virology, 7(2):107-122 (1997).
Hsu et al., "DNA Targeting Specificity of RNA-guided Cas9 Nucleases", Nature Biotechnology, 31(9):827-832, (2013).
Jin et al., "Silencing Herpes Simplex Virus Type 1 Capsid Protein Encoding Genes by siRNA: A Promising Antiviral Therapeutic Approach", PLOS One, 9(5):e96623, 12 pages (2014).
Jinek et al., "A Programmable Dual-RNA-Guided DNA Endonuclease in Adaptive Bacterial Immunity", Science, 337:816-821 (2012).
Kimberlin et al., "Safety and Efficacy of High-Dose Intravenous Acyclovir in the Management of Neonatal Herpes Simplex Virus Infections", Pediatrics, 108(2):230-238 (2001).
Kleinstiver et al., "Engineered CRISPR-Cas9 Nucleases with Altered PAM Specificities", Nature, 523(7561):481-485 (2015).
Labetoulle et al., "Incidence of Herpes Simplex Virus Keratitis in France", American Academy of Ophthalmology, 112(5):888-895 (2005).
Lee et al., "Nonendocytic Delivery of Functional Engineered Nanoparticles into the Cytoplasm of Live Cells Using a Novel, High-Throughput Microfluidic Device", Nano Letters, 12:6322-6327 (2012).
Lees-Miller et al., "Attenuation of DNA-Dependent Protein Kinase Activity and Its Catalytic Subunit by the Herpes Simplex Virus Type 1 Transactivator ICP0", Journal of Virology 70(11):7471-7477 (1996).
Leib et al., "Immediate-Early Regulatory Gene Mutants Define Different Stages in the Establishment and Reactivation of Herpes Simplex Virus Latency", Journal of Virology, 63(2):759-768 (1989).
Liesegang et al., Epidemiology of Ocular Herpes Simplex, Archives of Ophthalmology, 107:1155-1159 (1989).
McGeoch et al., "Topics in Herpesvirus Genomics and Evolution", Virus Research, 117:90-104 (2006).
Mefferd et al., "Expression of CRISPR/Cas Single Guide RNAs Using Small tRNA Promoters", RNA, 21(9):1683-1689 (2015).
Mettenleiter et al., "Herpesvirus Assembly: A Tale of Two Membranes", Current Opinion in Microbiology, 9:423-429 (2006).
Mossman et al., "Evidence that Herpes Simplex Virus VP16 Is Required for Viral Egress Downstream of the Initial Envelopment Event", Journal of Virology, 74(14):6287-6299 (2000).
Pinnoji et al., "Repressor Element-I Silencing Transcription Factor/neuronal Restrictive Silencer Factor (REST/NRSF) Can Regulate HSV-I Immediate-early Transcription via Histone Modification", Virology Journal, 4:56, 11 pages (2007).
Rajcani et al., "Peculiarities of Herpes Simplex Virus (HSV) Transcription: An Overview", Virus Genes 28(3):293-310 (2004).
Roizman et al., "The First 30 Minutes in the Life of a Virus: unREST in the Nucleus", Cell Cycle, 4(8):1019-1021 (2005).
Roy et al., "Acute Retinal Necrosis: Clinical Features, Management and Outcomes—a 10 Year Consecutive Case Series", Ocular Immunology and Inflammation, 22(3): 170-174 (2014).
Sacks et al., "Deletion Mutants in the Gene Encoding the Herpes Simplex Virus Type 1 Immediate-Early Protein ICP0 Exhibit Impaired Growth in Cell Culture", Journal of Virology 61(3):829-839 (1987).
Sambrook et al., Molecular Cloning, A Laboratory Manual, Second Edition, Cold Spring Harbor Laboratory Press (1989).
Sandri-Goldin, "The Many Roles of the Regulatory Protein ICP27 During Herpes Simplex Virus Infection", Frontiers in Bioscience, 13:5241-5256 (2008).
Svobodova et al., "Analysis of the Interaction between the Essential Herpes Simplex Virus 1 Tegument Proteins VP16 and VP1/2", Journal of Virology, 86(1):473-483 (2012).
Wilhelmus et al., "Prognostic Indicators of Herpetic Keratitis", Archives of Ophthalmology 99:1578-1582 (1981).
Zhou et al., "A Mutation in the DNA Polymerase Accessory Factor of Herpes Simplex Virus 1 Restores Viral DNA Replication in the Presence of Raltegravir", Journal of Virology, 88(19):11121-11129 (2014).

* cited by examiner

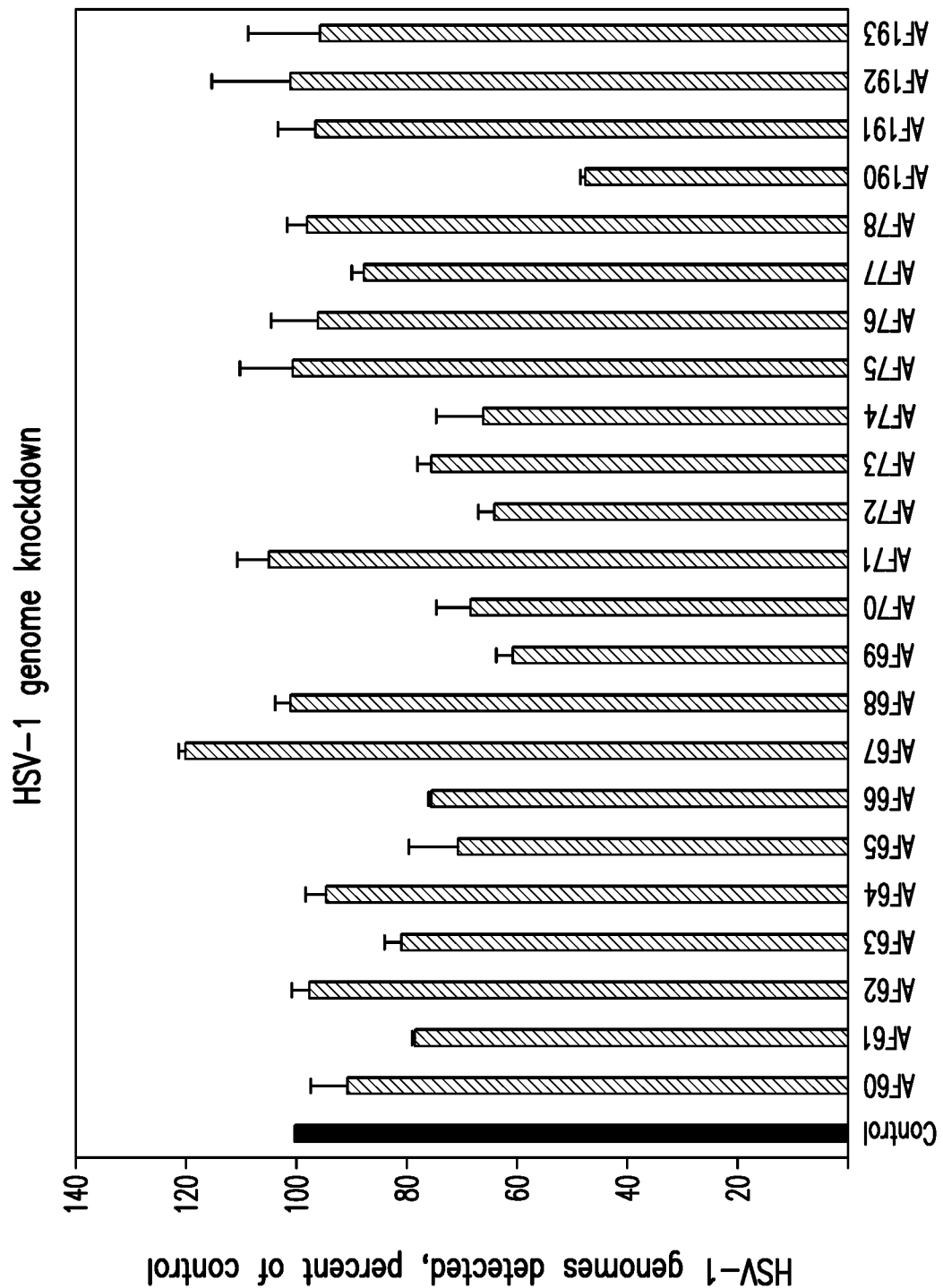

SEQUENCE LISTING

<160> NUMBER OF SEQ ID NOS: 39

<210> SEQ ID NO 1
<211> LENGTH: 22
<212> TYPE: RNA
<213> ORGANISM: Artificial Sequence
<220> FEATURE:
<223> OTHER INFORMATION: Synthetic

<400> SEQUENCE: 1
gcgucaucga ccucgucgga cu                                          22

<210> SEQ ID NO 2
<211> LENGTH: 20
<212> TYPE: RNA
<213> ORGANISM: Artificial Sequence
<220> FEATURE:
<223> OTHER INFORMATION: Synthetic

<400> SEQUENCE: 2
gucaucgacc ucgucggacu                                             20

<210> SEQ ID NO 3
<211> LENGTH: 22
<212> TYPE: RNA
<213> ORGANISM: Artificial Sequence
<220> FEATURE:
<223> OTHER INFORMATION: Synthetic

<400> SEQUENCE: 3
gggcgcggcg acaggcgguc cg                                          22

<210> SEQ ID NO 4
<211> LENGTH: 20
<212> TYPE: RNA
<213> ORGANISM: Artificial Sequence
<220> FEATURE:
<223> OTHER INFORMATION: Synthetic

<400> SEQUENCE: 4
gcgcggcgac aggcgguccg                                             20

<210> SEQ ID NO 5
<211> LENGTH: 20
<212> TYPE: RNA
<213> ORGANISM: Artificial Sequence
<220> FEATURE:
<223> OTHER INFORMATION: Synthetic

<400> SEQUENCE: 5
gacgggccuc caucccgggu                                             20

<210> SEQ ID NO 6
<211> LENGTH: 21
<212> TYPE: RNA
<213> ORGANISM: Artificial Sequence
<220> FEATURE:
<223> OTHER INFORMATION: Synthetic

<400> SEQUENCE: 6
gcgaggucgu gaagcuggaa u                                           21

<210> SEQ ID NO 7
<211> LENGTH: 21
<212> TYPE: RNA
<213> ORGANISM: Artificial Sequence

```
<220> FEATURE:
<223> OTHER INFORMATION: Synthetic

<400> SEQUENCE: 7
gacacgcacc gccaggagug u                                             21

<210> SEQ ID NO 8
<211> LENGTH: 20
<212> TYPE: RNA
<213> ORGANISM: Artificial Sequence
<220> FEATURE:
<223> OTHER INFORMATION: Synthetic

<400> SEQUENCE: 8
ggaguguucg agucgugucu                                               20

<210> SEQ ID NO 9
<211> LENGTH: 20
<212> TYPE: RNA
<213> ORGANISM: Artificial Sequence
<220> FEATURE:
<223> OTHER INFORMATION: Synthetic

<400> SEQUENCE: 9
ggagagccgc cgcgacgacc                                               20

<210> SEQ ID NO 10
<211> LENGTH: 22
<212> TYPE: RNA
<213> ORGANISM: Artificial Sequence
<220> FEATURE:
<223> OTHER INFORMATION: Synthetic

<400> SEQUENCE: 10
gaccuggaau cggacagcag cg                                            22

<210> SEQ ID NO 11
<211> LENGTH: 20
<212> TYPE: RNA
<213> ORGANISM: Artificial Sequence
<220> FEATURE:
<223> OTHER INFORMATION: Synthetic

<400> SEQUENCE: 11
gcgaccgucu ccucuaccuc                                               20

<210> SEQ ID NO 12
<211> LENGTH: 24
<212> TYPE: RNA
<213> ORGANISM: Artificial Sequence
<220> FEATURE:
<223> OTHER INFORMATION: Synthetic

<400> SEQUENCE: 12
gcccccccgg cccugagucg gagg                                          24

<210> SEQ ID NO 13
<211> LENGTH: 22
<212> TYPE: RNA
<213> ORGANISM: Artificial Sequence
<220> FEATURE:
<223> OTHER INFORMATION: Synthetic

<400> SEQUENCE: 13
gucucuguug uuugcaaggg gg                                            22
```

```
<210> SEQ ID NO 14
<211> LENGTH: 20
<212> TYPE: RNA
<213> ORGANISM: Artificial Sequence
<220> FEATURE:
<223> OTHER INFORMATION: Synthetic

<400> SEQUENCE: 14
ccuugugaaa caguacggcc                                                        20

<210> SEQ ID NO 15
<211> LENGTH: 20
<212> TYPE: RNA
<213> ORGANISM: Artificial Sequence
<220> FEATURE:
<223> OTHER INFORMATION: Synthetic

<400> SEQUENCE: 15
guacggcccc gaguucguga                                                        20

<210> SEQ ID NO 16
<211> LENGTH: 20
<212> TYPE: RNA
<213> ORGANISM: Artificial Sequence
<220> FEATURE:
<223> OTHER INFORMATION: Synthetic

<400> SEQUENCE: 16
gaggccgccg aggacgucag                                                        20

<210> SEQ ID NO 17
<211> LENGTH: 22
<212> TYPE: RNA
<213> ORGANISM: Artificial Sequence
<220> FEATURE:
<223> OTHER INFORMATION: Synthetic

<400> SEQUENCE: 17
gccccuccgg gggguuggg gu                                                      22

<210> SEQ ID NO 18
<211> LENGTH: 22
<212> TYPE: RNA
<213> ORGANISM: Artificial Sequence
<220> FEATURE:
<223> OTHER INFORMATION: Synthetic

<400> SEQUENCE: 18 gggggcguc uggccccucc gg                                                      22

<210> SEQ ID NO 19
<211> LENGTH: 20
<212> TYPE: RNA
<213> ORGANISM: Artificial Sequence
<220> FEATURE:
<223> OTHER INFORMATION: Synthetic

<400> SEQUENCE: 19
ucggggccgu acuguuucac                                                        20

<210> SEQ ID NO 20
<211> LENGTH: 24
<212> TYPE: RNA
<213> ORGANISM: Artificial Sequence
<220> FEATURE:
<223> OTHER INFORMATION: Synthetic
```

```
<400> SEQUENCE: 20
gguccgugcu guccgccucg gagg                                          24

<210> SEQ ID NO 21
<211> LENGTH: 24
<212> TYPE: RNA
<213> ORGANISM: Artificial Sequence
<220> FEATURE:
<223> OTHER INFORMATION: Synthetic

<400> SEQUENCE: 21
gccugauagu gggcgugacg ccca                                          24

<210> SEQ ID NO 22
<211> LENGTH: 24
<212> TYPE: RNA
<213> ORGANISM: Artificial Sequence
<220> FEATURE:
<223> OTHER INFORMATION: Synthetic

<400> SEQUENCE: 22
gucaucgucg ucggcucgaa aggc                                          24

<210> SEQ ID NO 23
<211> LENGTH: 24
<212> TYPE: RNA
<213> ORGANISM: Artificial Sequence
<220> FEATURE:
<223> OTHER INFORMATION: Synthetic

<400> SEQUENCE: 23
gccccgcucg ucgcggucug ggcu                                          24

<210> SEQ ID NO 24
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t

<400> SEQUENCE: 24 nngrrt                                                               6

<210> SEQ ID NO 25
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t

<400> SEQUENCE: 25 nngrrv                                                               6

<210> SEQ ID NO 26
<211> LENGTH: 3159
<212> TYPE: DNA
<213> ORGANISM: Staphylococcus aureus
```

<400> SEQUENCE: 26

```
atgaaaagga actacattct ggggctggcc atcgggatta caagcgtggg gtatgggatt      60
attgactatg aaacaaggga cgtgatcgac gcaggcgtca gactgttcaa ggaggccaac     120
gtggaaaaca atgagggacg agaagcaag aggggagcca ggcgcctgaa acgacggaga      180
aggcacagaa tccagagggt gaagaaactg ctgttcgatt acaacctgct gaccgaccat     240
tctgagctga gtggaattaa tccttatgaa gccagggtga aaggcctgag tcagaagctg     300
tcagaggaag agttttccgc agctctgctg cacctggcta agcgccgagg agtgcataac     360
gtcaatgagg tggaagagga caccggcaac gagctgtcta caaggaaca gatctcacgc     420
aatagcaaag ctctggaaga aagtatgtc gcagagctgc agctggaacg gctgaagaaa      480
gatggcgagg tgagagggtc aattaatagg ttcaagacaa gcgactacgt caaagaagcc     540
aagcagctgc tgaaagtgca aaggcttac caccagctgg atcagagctt catcgatact      600
tatatcgacc tgctggagac tcggagaacc tactatgagg gaccaggaga agggagcccc     660
ttcggatgga aagacatcaa ggaatggtac gagatgctga tgggacattg cacctatttt     720
ccagaagagc tgagaagcgt caagtacgct tataacgcag atctgtacaa cgccctgaat     780
gacctgaaca acctggtcat caccagggat gaaaacgaga actgaata ctatgagaag       840
ttccagatca tcgaaaacgt gtttaagcag aagaaaaagc ctacactgaa acagattgct     900
aaggagatcc tggtcaacga agaggacatc aagggctacc gggtgacaag cactggaaaa     960
ccagagttca ccaatctgaa agtgtatcac gatattaagg acatcacagc acggaaagaa    1020
atcattgaga cgccgaact gctggatcag attgctaaga tcctgactat ctaccagagc     1080
tccgaggaca tccaggaaga gctgactaac ctgaacagcg agctgaccca ggaagagatc    1140
gaacagatta gtaatctgaa ggggtacacc ggaacacaca acctgtccct gaaagctatc    1200
aatctgattc tggatgagct gtggcataca aacgacaatc agattgcaat cttaaccgg    1260
ctgaagctgg tcccaaaaaa ggtggacctg agtcagcaga aagagatccc aaccacactg    1320
gtggacgatt tcattctgtc acccgtggtc aagcggagct tcatccagag catcaaagtg    1380
atcaacgcca tcatcaagaa gtacggcctg cccaatgata tcattatcga gctggctagg    1440
gagaagaaca gcaaggacgc acagaagatg atcaatgaga tgcagaaacg aaaccggcag    1500
accaatgaac gcattgaaga gattatccga actaccggga agagaacgc aaagtacctg     1560
attgaaaaaa tcaagctgca cgatatgcag gagggaaagt gtctgtattc tctggaggcc    1620
atccccctgg aggacctgct gaacaatcca ttcaactacg aggtcgatca tattatcccc    1680
agaagcgtgt ccttcgacaa ttccttaac aacaaggtgc tggtcaagca ggaagagaac     1740
tctaaaaagg gcaataggac tccttttcag tacctgtcta gttcagattc caagatctct    1800
tacgaaaacct ttaaaaagca cattctgaat ctggccaaag gaagggccg catcagcaag    1860
accaaaaagg agtacctgct ggaagagcgg gacatcaaca gattctccgt ccagaaggat    1920
tttattaacc ggaatctggt ggacacaaga tacgctactc gcggcctgat gaatctgctg    1980
cgatcctatt tccgggtgaa caatctggat gtgaaagtca agtccatcaa cggcgggttc    2040
acatctttc tgaggcgcaa atggaagttt aaaaaggagc gcaacaaagg gtacaagcac    2100
catgccgaag atgctctgat tatcgcaaat gccgacttca tctttaagga gtggaaaaag    2160
ctggacaaag ccaagaaagt gatggagaac cagatgttcg aagagaagca ggccgaatct    2220
atgcccgaaa tcgagacaga acaggagtac aaggagattt tcatcactcc tcaccagatc    2280
aagcatatca aggatttcaa ggactacaag tactctcacc gggtggataa aaagcccaac    2340
```

```
agagagctga tcaatgacac cctgtatagt acaagaaaag acgataaggg gaataccctg    2400
attgtgaaca atctgaacgg actgtacgac aaagataatg acaagctgaa aaagctgatc    2460
aacaaaagtc ccgagaagct gctgatgtac caccatgatc ctcagacata tcagaaactg    2520
aagctgatta tggagcagta cggcgacgag aagaacccac tgtataagta ctatgaagag    2580
actgggaact acctgaccaa gtatagcaaa aaggataatg gccccgtgat caagaagatc    2640
aagtactatg gaacaagct gaatgcccat ctggacatca cagacgatta ccctaacagt    2700
cgcaacaagg tggtcaagct gtcactgaag ccatacagat cgatgtcta tctggacaac    2760 ggcgtgtata aatttgtgac tgtcaagaat ctggatgtca tcaaaaagga gaactactat    2820
gaagtgaata gcaagtgcta cgaagaggct aaaaagctga aaaagattag caaccaggca    2880
gagttcatcg cctccttta caacaacgac ctgattaaga tcaatggcga actgtatagg    2940
gtcatcgggg tgaacaatga tctgctgaac cgcattgaag tgaatatgat tgacatcact    3000
taccgagagt atctggaaaa catgaatgat aagcgccccc ctcgaattat caaaacaatt    3060
gcctctaaga ctcagagtat caaaaagtac tcaaccgaca ttctgggaaa cctgtatgag    3120
gtgaagagca aaaagcaccc tcagattatc aaaaagggc                          3159

<210> SEQ ID NO 27
<211> LENGTH: 3159
<212> TYPE: DNA
<213> ORGANISM: Staphylococcus aureus

<400> SEQUENCE: 27
atgaaaagga actacattct ggggctggac atcgggatta caagcgtggg gtatgggatt     60
attgactatg aaacaaggga cgtgatcgac gcaggcgtca gactgttcaa ggaggccaac    120
gtggaaaaca atgagggacg gagaagcaag aggggagcca ggcgcctgaa acgacggaga    180
aggcacagaa tccagagggt gaagaaactg ctgttcgatt acaacctgct gaccgaccat    240
tctgagctga gtggaattaa tccttatgaa gccagggtga aaggcctgag tcagaagctg    300
tcagaggaag agttttccgc agctctgctg cacctggcta gcgccgaggg agtgcataac    360
gtcaatgagg tggaagagga caccggcaac gagctgtcta caaaggaaca gatctcacgc    420
aatagcaaag ctctggaaga gaagtatgtc gcagagctgc agctggaacg gctgaagaaa    480
gatggcgagg tgagagggtc aattaatagg ttcaagacaa gcgactacgt caaagaagcc    540
aagcagctgc tgaaagtgca gaaggcttac caccagctgg atcagagctt catcgatact    600
tatatcgacc tgctggagac tcggagaacc tactatgagg accaggagag gggagccccc    660
ttcggatgga agacatcaa ggaatggtac gagatgctga tgggacattg cacctatttt    720
ccagaagagc tgaaagcgt caagtacgct tataacgcag atctgtacaa cgccctgaat    780
gacctgaaca acctggtcat caccagggat gaaaacgaga actggaata ctatgagaag    840 ttccagatca tcgaaaacgt gtttaagcag aagaaaagc ctacactgaa acagattgct    900
aaggagatcc tggtcaacga gaggacatc aagggctacc gggtgacaag cactggaaaa    960
ccagagttca ccaatctgaa agtgtatcac gatattaagg acatcacagc acggaaagaa   1020
atcattgaga acgccgaact gctggatcag attgctaaga tcctgactat ctaccagagc   1080
tccgaggaca tccaggaaga gctgactaac ctgaacagcg agctgaccca ggaagagatc   1140
gaacagatta gtaatctgaa ggggtacacc ggaacacaca cctgtcccct gaaagctatc   1200
aatctgattc tggatgagct gtggcataca aacgacaatc agattgcaat ctttaaccgg   1260
```

```
ctgaagctgg tcccaaaaaa ggtggacctg agtcagcaga aagagatccc aaccacactg    1320
gtggacgatt tcattctgtc acccgtggtc aagcggagct tcatccagag catcaaagtg    1380
atcaacgcca tcatcaagaa gtacggcctg cccaatgata tcattatcga gctggctagg    1440
gagaagaaca gcaaggacgc acagaagatg atcaatgaga tgcagaaacg aaaccggcag    1500
accaatgaac gcattgaaga gattatccga actaccggga agagaacgc aaagtacctg    1560 attgaaaaaa tcaagctgca cgatatgcag gagggaaagt gtctgtattc tctggaggcc    1620 atcccccctgg aggacctgct gaacaatcca ttcaactacg aggtcgatca tattatcccc    1680
agaagcgtgt ccttcgacaa ttcctttaac aacaaggtgc tggtcaagca ggaagaggcc    1740
tctaaaaagg gcaataggac tccttttccag tacctgtcta gttcagattc caagatctct    1800
tacgaaacct ttaaaaagca cattctgaat ctggccaaag aaagggccg catcagcaag    1860 accaaaaagg agtacctgct ggaagagcgg gacatcaaca gattctccgt ccagaaggat    1920
tttattaacc ggaatctggt ggacacaaga tacgctactc gcggcctgat gaatctgctg    1980
cgatcctatt tccgggtgaa caatctggat gtgaaagtca agtccatcaa cggcgggttc    2040 acatctttc tgaggcgcaa atggaagttt aaaaaggagc gcaacaaagg gtacaagcac    2100
catgccgaag atgctctgat tatcgcaaat gccgacttca tctttaagga gtggaaaaag    2160
ctggacaaag ccaagaaagt gatggagaac cagatgttcg aagagaagca ggccgaatct    2220
atgcccgaaa tcgagacaga acaggagtac aaggagattt tcatcactcc tcaccagatc    2280
aagcatatca aggatttcaa ggactacaag tactctcacc gggtggataa aaagcccaac    2340
agagagctga tcaatgacac cctgtatagt acaagaaaag acgataaggg gaatacctg    2400 attgtgaaca atctgaacgg actgtacgac aaagataatg acaagctgaa aaagctgatc    2460
aacaaaagtc ccgagaagct gctgatgtac caccatgatc ctcagacata tcagaaactg    2520
aagctgatta tggagcagta cggcgacgag aagaaccaac tgtataagta ctatgaagag    2580
actgggaact acctgaccaa gtatagcaaa aaggataatg gccccgtgat caagaagatc    2640
aagtactatg ggaacaagct gaatgcccat ctggacatca cagacgatta ccctaacagt    2700
cgcaacaagg tggtcaagct gtcactgaag ccatacagat tcgatgtcta tctggacaac    2760
ggcgtgtata aatttgtgac tgtcaagaat ctggatgtca tcaaaaagga gaactactat    2820
gaagtgaata gcaagtgcta cgaagaggct aaaaagctga aaaagattag caaccaggca    2880
gagttcatcg cctcctttta caacaacgac ctgattaaga tcaatggcga actgtatagg    2940
gtcatcgggg tgaacaatga tctgctgaac cgcattgaag tgaatatgat tgacatcact    3000
taccgagagt atctggaaaa catgaatgat aagcgccccc tcgaattat caaaacaatt    3060 gcctctaaga ctcagagtat caaaaagtac tcaaccgaca ttctgggaaa cctgtatgag    3120
gtgaagagca aaaagcaccc tcagattatc aaaaagggc                          3159
```

<210> SEQ ID NO 28
<211> LENGTH: 4107
<212> TYPE: DNA
<213> ORGANISM: Streptococcus pyogenes

<400> SEQUENCE: 28

```
atggataaaa agtacagcat cgggctggac atcggtacaa actcagtggg gtgggccgtg     60
attacgacgc agtacaaggt accctccaaa aaatttaaag tgctgggtaa cacggacaga    120
cactctataa agaaaaatct tattggagcc ttgctgttcg actcaggcga gacagccgaa    180
gccacaaggt tgaagcggac cgccaggagg cggtatacca ggagaaagaa ccgcatatgc    240
```

```
tacctgcaag aaatcttcag taacgagatg gcaaaggttg acgatagctt tttccatcgc    300
ctggaagaat cctttcttgt tgaggaagac aagaagcacg aacggcaccc catctttggc    360
aatattgtcg acgaagtggc atatcacgaa aagtacccga ctatctacca cctcaggaag    420
aagctggtgg actctaccga taaggcggac ctcagactta tttatttggc actcgcccac    480
atgattaaat ttagaggaca tttcttgatc gagggcgacc tgaacccgga caacagtgac    540
gtcgataagc tgttcatcca acttgtgcag acctacaatc aactgttcga agaaaaccct    600
ataaatgctt caggagtcga cgctaaagca atcctgtccg cgcgcctctc aaaatctaga    660
agacttgaga atctgattgc tcagttgccc ggggaaaaga aaatggatt gtttggcaac    720 ctgatcgccc tcagtctcgg actgacccca aatttcaaaa gtaacttcga cctggccgaa    780
gacgctaagc tccagctgtc caaggacaca tacgatgacg acctcgacaa tctgctggcc    840
cagattgggg atcagtacgc cgatctcttt ttggcagcaa agaacctgtc cgacgccatc    900
ctgttgagcg atatcttgag agtgaacacc gaaattacta agcacccct tagcgcatct    960 atgatcaagc ggtacgacga gcatcatcag gatctgaccc tgctgaaggc tcttgtgagg   1020
caacagctcc ccgaaaaata caaggaaatc ttctttgacc agagcaaaaa cggctacgct   1080
ggctatatag atggtggggc cagtcaggag gaattctata aattcatcaa gcccattctc   1140
gagaaaatgg acggcacaga ggagttgctg gtcaaactta acaggagga cctgctgcgg   1200 aagcagcgga cctttgacaa cgggtctatc ccccaccaga ttcatctggg cgaactgcac   1260
gcaatcctga ggaggcagga ggattttat ccttttctta aagataaccg cgagaaaata   1320
gaaaagattc ttacattcag gatcccgtac tacgtgggac ctctcgcccg gggcaattca   1380
cggtttgcct ggatgacaag gaagtcagag gagactatta caccttggaa cttcgaagaa   1440
gtggtggaca agggtgcatc tgcccagtct ttcatcgagc ggatgacaaa ttttgacaag   1500
aacctcccta atgagaaggt gctgcccaaa cattctctgc tctacgagta ctttaccgtc   1560
tacaatgaac tgactaaagt caagtacgtc accgagggaa tgaggaagcc ggcattcctt   1620
agtggagaac agaagaaggc gattgtagac ctgttgttca agaccaacag gaaggtgact   1680
gtgaagcaac ttaagaaga ctactttaag aagatcgaat gttttgacag tgtgaaaatt   1740
tcaggggttg aagaccgctt caatgcgtca ttggggactt accatgatct tctcaagatc   1800
ataaaggaca aagacttcct ggacaacgaa gaaaatgagg atattctcga agacatcgtc   1860 ctcacctga ccctgttcga agacagggaa atgatagaag agcgcttgaa aacctatgcc   1920
cacctcttcg acgataaagt tatgaagcag ctgaagcgca ggagatacac aggatgggga   1980
agattgtcaa ggaagctgat caatggaatt agggataaac agagtggcaa gaccatactg   2040
gatttcctca atctgatgg cttcgccaat aggaacttca tgcaactgat tcacgatgac   2100
tctcttacct tcaaggagga cattcaaaag gctcaggtga gcgggcaggg agactccctt   2160
catgaacaca tcgcgaattt ggcaggttcc ccgctattaa aaagggcat ccttcaaact   2220 gtcaaggtgg tggatgaatt ggtcaaggta atgggcagac ataagccaga aaatattgtg   2280
atcgagatgg cccgcgaaaa ccagaccaca cagaagggcc agaaaaatag tagagagcgg   2340
atgaagagga tcgaggaggg catcaaagag ctggatctc agattctcaa agaacaccc   2400 gtagaaaaca cacagctgca gaacgaaaaa ttgtacttgt actatctgca gaacggcaga   2460
gacatgtacg tcgaccaaga acttgatatt aatagactgt ccgactatga cgtagaccat   2520
atcgtgcccc agtccttcct gaaggacgac tccattgata caaagtctt gacaagaagc   2580
```

```
gacaagaaca ggggtaaaag tgataatgtg cctagcgagg aggtggtgaa aaaaatgaag    2640
aactactggc gacagctgct taatgcaaag ctcattacac aacggaagtt cgataatctg    2700
acgaaagcag agagaggtgg cttgtctgag ttggacaagg cagggtttat taagcggcag    2760
ctggtggaaa ctaggcagat cacaaagcac gtggcgcaga ttttggacag ccggatgaac    2820
acaaaatacg acgaaaatga taaactgata cgagaggtca agttatcac gctgaaaagc    2880 aagctggtgt ccgattttcg gaaagacttc cagttctaca agttcgcga gattaataac    2940 taccatcatg ctcacgatgc gtacctgaac gctgttgtcg ggaccgcctt gataaagaag    3000
tacccaaagc tggaatccga gttcgtatac ggggattaca aagtgtacga tgtgaggaaa    3060
atgatagcca agtccgagca ggagattgga aaggccacag ctaagtactt ctttttattct   3120 aacatcatga atttttttaa gacggaaatt accctggcca acggagagat cagaaagcgg    3180 cccctttatag agacaaatgg tgaaacaggt gaaatcgtct gggataaggg cagggatttc   3240
gctactgtga ggaaggtgct gagtatgcca caggtaaata tcgtgaaaaa aaccgaagta    3300
cagaccggag gattttccaa ggaaagcatt ttgcctaaaa gaaactcaga caagctcatc    3360
gcccgcaaga aagattggga ccctaagaaa tacgggggat ttgactcacc caccgtagcc    3420
tattctgtgc tggtggtagc taaggtgaaa aaaggaaagt ctaagaagct gaagtccgtg    3480
aaggaactct tgggaatcac tatcatggaa agatcatcct ttgaaaagaa ccctatcgat    3540
ttcctggagg ctaagggtta caaggaggtc aagaaagacc tcatcattaa actgccaaaa    3600
tactctctct tcgagctgga aaatggcagg aagagaatgt tggccagcgc cggagagctg    3660
caaaagggaa acgagcttgc tctgcccctcc aaatatgtta attttctcta tctcgcttcc    3720
cactatgaaa agctgaaagg gtctcccgaa gataacgagc agaagcagct gttcgtcgaa    3780
cagcacaagc actatctgga tgaaataatc gaacaaataa gcgagttcag caaaaggggtt    3840 atcctggcgg atgctaattt ggacaaagta ctgtctgctt ataacaagca ccgggataag    3900
cctattaggg aacaagccga gaatataatt caccctcttta cactcacgaa tctcggagcc    3960
cccgccgcct tcaaatactt tgatacgact atcgaccgga acggtatac cagtaccaaa    4020 gaggtcctcg atgccaccct catccaccag tcaattactg gcctgtacga aacacggatc    4080
gacctctctc aactgggcgg cgactag                                         4107
```

<210> SEQ ID NO 29
<211> LENGTH: 1368
<212> TYPE: PRT
<213> ORGANISM: Streptococcus pyogenes
<220> FEATURE:
<221> NAME/KEY: misc_feature
<222> LOCATION: (10)..(21)
<223> OTHER INFORMATION: N-terminal RuvC-like domain
<220> FEATURE:
<221> NAME/KEY: misc_feature
<222> LOCATION: (759)..(766)
<223> OTHER INFORMATION: RuvC-like domain
<220> FEATURE:
<221> NAME/KEY: misc_feature
<222> LOCATION: (837)..(863)
<223> OTHER INFORMATION: HNH-like domain
<220> FEATURE:
<221> NAME/KEY: misc_feature
<222> LOCATION: (982)..(989)
<223> OTHER INFORMATION: RuvC-like domain

<400> SEQUENCE: 29

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile

-continued

```
                435                 440                 445
Pro Tyr Tyr Val Gly Pro Leu Ala Arg Gly Asn Ser Arg Phe Ala Trp
450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
                515                 520                 525
Tyr Val Thr Glu Gly Met Arg Lys Pro Ala Phe Leu Ser Gly Glu Gln
530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
                675                 680                 685
Ala Asn Arg Asn Phe Met Gln Leu Ile His Asp Asp Ser Leu Thr Phe
690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
                755                 760                 765
Thr Thr Gln Lys Gly Gln Lys Asn Ser Arg Glu Arg Met Lys Arg Ile
770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
                835                 840                 845
Asp Asp Ser Ile Asp Asn Lys Val Leu Thr Arg Ser Asp Lys Asn Arg
850                 855                 860
```

```
Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260
```

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

<210> SEQ ID NO 30
<211> LENGTH: 1368
<212> TYPE: PRT
<213> ORGANISM: Streptococcus pyogenes
<220> FEATURE:
<221> NAME/KEY: misc_feature
<223> OTHER INFORMATION: S. pyogenes Cas9 variant: EQR variant

<400> SEQUENCE: 30

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

```
Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670
```

-continued

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
    755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr

```
                    1085                1090                1095

Glu Val Gln Thr Gly Gly Phe Ser Lys Glu Ser Ile Leu Pro Lys
            1100                1105                1110

Arg Asn Ser Asp Lys Leu Ile Ala Arg Lys Lys Asp Trp Asp Pro
            1115                1120                1125

Lys Lys Tyr Gly Gly Phe Glu Ser Pro Thr Val Ala Tyr Ser Val
            1130                1135                1140

Leu Val Val Ala Lys Val Glu Lys Gly Lys Ser Lys Lys Leu Lys
            1145                1150                1155

Ser Val Lys Glu Leu Leu Gly Ile Thr Ile Met Glu Arg Ser Ser
            1160                1165                1170

Phe Glu Lys Asn Pro Ile Asp Phe Leu Glu Ala Lys Gly Tyr Lys
            1175                1180                1185

Glu Val Lys Lys Asp Leu Ile Ile Lys Leu Pro Lys Tyr Ser Leu
            1190                1195                1200

Phe Glu Leu Glu Asn Gly Arg Lys Arg Met Leu Ala Ser Ala Gly
            1205                1210                1215

Glu Leu Gln Lys Gly Asn Glu Leu Ala Leu Pro Ser Lys Tyr Val
            1220                1225                1230

Asn Phe Leu Tyr Leu Ala Ser His Tyr Glu Lys Leu Lys Gly Ser
            1235                1240                1245

Pro Glu Asp Asn Glu Gln Lys Gln Leu Phe Val Glu Gln His Lys
            1250                1255                1260

His Tyr Leu Asp Glu Ile Ile Glu Gln Ile Ser Glu Phe Ser Lys
            1265                1270                1275

Arg Val Ile Leu Ala Asp Ala Asn Leu Asp Lys Val Leu Ser Ala
            1280                1285                1290

Tyr Asn Lys His Arg Asp Lys Pro Ile Arg Glu Gln Ala Glu Asn
            1295                1300                1305

Ile Ile His Leu Phe Thr Leu Thr Asn Leu Gly Ala Pro Ala Ala
            1310                1315                1320

Phe Lys Tyr Phe Asp Thr Thr Ile Asp Arg Lys Gln Tyr Arg Ser
            1325                1330                1335

Thr Lys Glu Val Leu Asp Ala Thr Leu Ile His Gln Ser Ile Thr
            1340                1345                1350

Gly Leu Tyr Glu Thr Arg Ile Asp Leu Ser Gln Leu Gly Gly Asp
            1355                1360                1365

<210> SEQ ID NO 31
<211> LENGTH: 1368
<212> TYPE: PRT
<213> ORGANISM: Streptococcus pyogenes
<220> FEATURE:
<221> NAME/KEY: misc_feature
<223> OTHER INFORMATION: S. pyogenes Cas9 variant: VRER variant

<400> SEQUENCE: 31

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60
```

-continued

```
Lys Arg Thr Ala Arg Arg Tyr Thr Arg Lys Asn Arg Ile Cys
 65                  70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
```

```
            485                 490                 495
Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910
```

-continued

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Val Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Arg
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

| | | | | | | | | | | |
|---|---|---|---|---|---|---|---|---|---|---|
| Ile | Ile | His | Leu | Phe | Thr | Leu | Thr | Asn | Leu | Gly | Ala | Pro | Ala | Ala |
| | 1310 | | | | 1315 | | | | 1320 | |

Phe Lys Tyr Phe Asp Thr Thr Ile Asp Arg Lys Glu Tyr Arg Ser
    1325                    1330                    1335

Thr Lys Glu Val Leu Asp Ala Thr Leu Ile His Gln Ser Ile Thr
    1340                    1345                    1350

Gly Leu Tyr Glu Thr Arg Ile Asp Leu Ser Gln Leu Gly Gly Asp
    1355                    1360                    1365

<210> SEQ ID NO 32
<211> LENGTH: 3159
<212> TYPE: DNA
<213> ORGANISM: Staphylococcus aureus

<400> SEQUENCE: 32

| | |
|---|---|
| atgaaaagga actacattct ggggctggac atcgggatta caagcgtggg gtatgggatt | 60 |
| attgactatg aaacaaggga cgtgatcgac gcaggcgtca gactgttcaa ggaggccaac | 120 |
| gtggaaaaca atgaggacg gagaagcaag aggggagcca ggcgcctgaa cgacggaga | 180 |
| aggcacagaa tccagagggt gaagaaactg ctgttcgatt acaacctgct gaccgaccat | 240 |
| tctgagctga gtggaattaa tcctttatgaa gccagggtga aaggcctgag tcagaagctg | 300 |
| tcagaggaag agttttccgc agctctgctg cacctggcta agcgccgagg agtgcataac | 360 |
| gtcaatgagg tggaagagga caccggcaac gagctgtcta caaggaaca gatctcacgc | 420 |
| aatagcaaag ctctggaaga gaagtatgtc gcagagctgc agctggaacg gctgaagaaa | 480 |
| gatggcgagg tgagagggtc aattaatagg ttcaagacaa gcgactacgt caaagaagcc | 540 |
| aagcagctgc tgaaagtgca gaaggcttac caccagctgg atcagagctt catcgatact | 600 |
| tatatcgacc tgctggagac tcggagaacc tactatgagg gaccaggaga agggagcccc | 660 |
| ttcggatgga aagacatcaa ggaatggtac gagatgctga tgggacattg cacctatttt | 720 |
| ccagaagagc tgaagagcgt caagtacgct tataacgcag atctgtacaa cgccctgaat | 780 |
| gacctgaaca acctggtcat caccagggat gaaaacgaga actggaata ctatgagaag | 840 |
| ttccagatca tcgaaaacgt gtttaagcag aagaaaaagc ctacactgaa acagattgct | 900 |
| aaggagatcc tggtcaacga gaggacatc aagggctacc gggtgacaag cactggaaaa | 960 |
| ccagagttca ccaatctgaa agtgtatcac gatattaagg acatcacagc acggaaagaa | 1020 |
| atcattgaga acgccgaact gctggatcag attgctaaga tcctgactat ctaccagagc | 1080 |
| tccgaggaca tccaggaaga gctgactaac ctgaacagcg agctgaccca ggaagagatc | 1140 |
| gaacagatta gtaatctgaa ggggtacacc ggaacacaca acctgtccct gaaagctatc | 1200 |
| aatctgattc tggatgagct gtggcataca aacgacaatc agattgcaat ctttaaccgg | 1260 |
| ctgaagctgg tcccaaaaaa ggtggacctg agtcagcaga aagagatccc aaccacactg | 1320 |
| gtggacgatt tcattctgtc acccgtggtc aagcggagct tcatccagag catcaaagtg | 1380 |
| atcaacgcca tcatcaagaa gtacggcctg cccaatgata tcattatcga gctggctagg | 1440 |
| gagaagaaca gcaaggacgc acagaagatg atcaatgaga tgcagaaacg aaaccggcag | 1500 |
| accaatgaac gcattgaaga gattatccga actaccggga agagaacgc aaagtacctg | 1560 |
| attgaaaaaa tcaagctgca cgatatgcag gagggaaagt gtctgtattc tctggaggcc | 1620 |
| atccccctgg aggacctgct gaacaatcca ttcaactacg aggtcgatca tattatcccc | 1680 |
| agaagcgtgt ccttcgacaa ttccttaac aacaaggtgc tggtcaagca ggaagagaac | 1740 |
| tctaaaaagg gcaataggac tccttttccag tacctgtcta gttcagattc caagatctct | 1800 |

```
tacgaaacct ttaaaaagca cattctgaat ctggccaaag gaaagggccg catcagcaag    1860
accaaaaagg agtacctgct ggaagagcgg gacatcaaca gattctccgt ccagaaggat    1920
tttattaacc ggaatctggt ggacacaaga tacgctactc gcggcctgat gaatctgctg    1980
cgatcctatt tccgggtgaa caatctggat gtgaaagtca agtccatcaa cggcgggttc    2040
acatctttc tgaggcgcaa atggaagttt aaaaaggagc gcaacaaagg gtacaagcac    2100
catgccgaag atgctctgat tatcgcaaat gccgacttca tctttaagga gtggaaaaag    2160
ctggacaaag ccaagaaagt gatggagaac cagatgttcg aagagaagca ggccgaatct    2220
atgcccgaaa tcgagacaga acaggagtac aaggagattt tcatcactcc tcaccagatc    2280
aagcatatca aggatttcaa ggactacaag tactctcacc gggtggataa aaagcccaac    2340
agagagctga tcaatgacac cctgtatagt acaagaaaag acgataaggg gaataccctg    2400
attgtgaaca atctgaacgg actgtacgac aaagataatg caagctgaa aaagctgatc    2460
aacaaaagtc ccgagaagct gctgatgtac caccatgatc ctcagacata tcagaaactg    2520
aagctgatta tggagcagta cggcgacgag aagaacccac tgtataagta ctatgaagag    2580
actgggaact acctgaccaa gtatagcaaa aaggataatg gccccgtgat caagaagatc    2640
aagtactatg gaacaagct gaatgcccat ctggacatca cagacgatta ccctaacagt    2700
cgcaacaagg tggtcaagct gtcactgaag ccatacagat cgatgtcta tctggacaac    2760
ggcgtgtata aatttgtgac tgtcaagaat ctggatgtca tcaaaaagga gaactactat    2820
gaagtgaata gcaagtgcta cgaagaggct aaaaagctga aaaagattag caaccaggca    2880
gagttcatcg cctcctttta caacaacgac ctgattaaga tcaatggcga actgtatagg    2940
gtcatcgggg tgaacaatga tctgctgaac cgcattgaag tgaatatgat tgacatcact    3000
taccgagagt atctggaaaa catgaatgat aagcgccccc tcgaattat caaaacaatt    3060
gcctctaaga ctcagagtat caaaaagtac tcaaccgaca ttctgggaaa cctgtatgag    3120
gtgaagagca aaaagcaccc tcagattatc aaaaagggc                          3159
```

<210> SEQ ID NO 33
<211> LENGTH: 3159
<212> TYPE: DNA
<213> ORGANISM: Staphylococcus aureus

<400> SEQUENCE: 33

```
atgaagcgga actacatcct gggcctggac atcggcatca ccagcgtggg ctacggcatc      60
atcgactacg agacacggga cgtgatcgat gccggcgtgc ggctgttcaa agaggccaac     120
gtggaaaaca cgagggcag gcggagcaag agaggcgcca aaggctgaa gcggcggagg       180
cggcatagaa tccagagagt gaagaagctg ctgttcgact acaacctgct gaccgaccac     240
agcgagctga gcggcatcaa ccctacgag gccagagtga agggcctgag ccagaagctg     300
agcgaggaag agttctctgc cgccctgctg cacctggcca agagaagagg cgtgcacaac     360
gtgaacgagg tggaagagga caccggcaac gagctgtcca ccaaagagca gatcagccgg     420
aacagcaagg ccctggaaga gaaatacgtg gccgaactgc agctggaacg gctgaagaaa     480
gacggcgaag tgcgggcag catcaacaga ttcaagacca cgcgactacgt gaaagaagcc     540
aaacagctgc tgaaggtgca gaaggcctac caccagctgg accagagctt catcgacacc     600
tacatcgacc tgctggaaac ccggcggacc tactatgagg acctggcga gggcagcccc     660
ttcggctgga aggacatcaa agaatggtac gagatgctga tgggccactg cacctacttc     720
```

```
cccgaggaac tgcggagcgt gaagtacgcc tacaacgccg acctgtacaa cgccctgaac    780
gacctgaaca atctcgtgat caccagggac gagaacgaga agctggaata ttacgagaag    840
ttccagatca tcgagaacgt gttcaagcag aagaagaagc ccaccctgaa gcagatcgcc    900
aaagaaatcc tcgtgaacga agaggatatt aagggctaca gagtgaccag caccggcaag    960
cccgagttca ccaacctgaa ggtgtaccac gacatcaagg acattaccgc cggaaagag   1020 attattgaga cgccgagct gctggatcag attgccaaga tcctgaccat ctaccagagc    1080
agcgaggaca tccaggaaga actgaccaat ctgaactccg agctgaccca ggaagagatc    1140
gagcagatct ctaatctgaa gggctatacc ggcacccaca acctgagcct gaaggccatc    1200
aacctgatcc tggacgagct gtggcacacc aacgacaacc agatcgctat cttcaaccgg    1260
ctgaagctgg tgcccaagaa ggtggacctg tcccagcaga agagatccc caccaccctg    1320 gtggacgact tcatcctgag ccccgtcgtg aagagaagct tcatccagag catcaaagtg    1380
atcaacgcca tcatcaagaa gtacggcctg cccaacgaca tcattatcga gctggcccgc    1440
gagaagaact ccaaggacgc ccagaaaatg atcaacgaga tgcagaagcg gaaccggcag    1500
accaacgagc ggatcgagga aatcatccgg accaccggca agagaacgc caagtacctg    1560 atcgagaaga tcaagctgca cgacatgcag gaaggcaagt gcctgtacag cctggaagcc    1620
atccctctgg aagatctgct gaacaacccc ttcaactatg aggtggacca catcatcccc    1680
agaagcgtgt ccttcgacaa cagcttcaac aacaaggtgc tcgtgaagca ggaagaaaac    1740
agcaagaagg gcaaccggac cccattccag tacctgagca gcagcgacag caagatcagc    1800
tacgaaacct tcaagaagca catcctgaat ctggccaagg gcaagggcag aatcagcaag    1860
accaagaaag agtatctgct ggaagaacgg gacatcaaca ggttctccgt gcagaaagac    1920
ttcatcaacc ggaacctggt ggataccaga tacgccacca gaggcctgat gaacctgctg    1980
cggagctact tcagagtgaa caacctggac gtgaaagtga agtccatcaa tggcggcttc    2040
accagctttc tgcggcggaa gtggaagttt aagaaagagc ggaacaaggg gtacaagcac    2100
cacgccgagg acgccctgat cattgccaac gccgatttca tcttcaaaga gtggaagaaa    2160
ctggacaagg ccaaaaaagt gatggaaaac cagatgttcg aggaaaagca ggccgagagc    2220
atgcccgaga tcgaaaccga gcaggagtac aaagagatct tcatcacccc caccagatc    2280 aagcacatta aggacttcaa ggactacaag tacagccacc gggtggacaa gaagcctaat    2340
agagagctga ttaacgacac cctgtactcc acccggaagg acgacaaggg caacaccctg    2400
atcgtgaaca atctgaacgg cctgtacgac aaggacaatg acaagctgaa aaagctgatc    2460
aacaagagcc ccgaaaagct gctgatgtac caccacgacc cccagaccta ccagaaactg    2520
aagctgatta tggaacagta cggcgacgag aagaatcccc tgtacaagta ctacgaggaa    2580
accgggaact acctgaccaa gtactccaaa aaggacaacg gccccgtgat caagaagatt    2640
aagtattacg gcaacaaact gaacgcccat ctggacatca ccgacgacta ccccaacagc    2700
agaaacaagg tcgtgaagct gtccctgaag ccctacagat cgacgtgta cctggacaat    2760 ggcgtgtaca agttcgtgac cgtgaagaat ctggatgtga tcaaaaaaga aaactactac    2820
gaagtgaata gcaagtgcta tgaggaagct aagaagctga gaagatcag caaccaggcc    2880 gagtttatcg cctccttcta caacaacgat ctgatcaaga tcaacggcga gctgtataga    2940
gtgatcggcg tgaacaacga cctgctgaac cggatcgaag tgaacatgat cgacatcacc    3000
taccgcgagt acctggaaaa catgaacgac aagaggcccc ccaggatcat taagacaatc    3060
gcctccaaga cccagagcat taagaagtac agcacagaca ttctgggcaa cctgtatgaa    3120
```

```
gtgaaatcta agaagcaccc tcagatcatc aaaaagggc                            3159
```

<210> SEQ ID NO 34
<211> LENGTH: 3159
<212> TYPE: DNA
<213> ORGANISM: Staphylococcus aureus

<400> SEQUENCE: 34

```
atgaagcgca actacatcct cggactggac atcggcatta cctccgtggg atacggcatc     60
atcgattacg aaactaggga tgtgatcgac gctggagtca ggctgttcaa agaggcgaac    120
gtggagaaca acgaggggcg gcgctcaaag aggggggccc gccggctgaa gcgccgccgc    180
agacatagaa tccagcgcgt gaagaagctg ctgttcgact acaaccttct gaccgaccac    240
tccgaacttt ccggcatcaa cccatatgag gctagagtga agggattgtc ccaaaagctg    300
tccgaggaag agttctccgc cgcgttgctc cacctcgcca gcgcagggg agtgcacaat     360
gtgaacgaag tggaagaaga taccggaaac gagctgtcca ccaaggagca gatcagccgg    420
aactccaagg ccctggaaga gaaatacgtg gcggaactgc aactggagcg gctgaagaaa    480
gacgagaag tgcgcggctc gatcaaccgc ttcaagacct cggactacgt gaaggaggcc     540
aagcagctcc tgaaagtgca aaaggcctat caccaacttg accagtcctt tatcgatacc    600
tacatcgatc tgctcgagac tcggcggact tactacgagg gtccagggga gggctcccca    660
tttggttgga aggatattaa ggagtggtac gaaatgctga tgggacactg cacatacttc    720
cctgaggagc tgcggagcgt gaaatacgca tacaacgcag acctgtacaa cgcgctgaac    780
gacctgaaca atctcgtgat cacccgggac gagaacgaaa agctcgagta ttacgaaaag    840
ttccagatta ttgagaacgt gttcaaacag aagaagaagc cgacactgaa gcagattgcc    900
aaggaaatcc tcgtgaacga gaggacatc aagggctatc gagtgacctc aacgggaaag     960
ccggagttca ccaatctgaa ggtctaccac gacatcaaag acattaccgc ccggaaggag   1020
atcattgaga acgcggagct gttggaccag attgcgaaga ttctgaccat ctaccaatcc   1080
tccgaggata ttcaggaaga actcaccaac ctcaacagcg aactgaccca ggaggagata   1140
gagcaaatct ccaacctgaa gggctacacc ggaactcata acctgagcct gaaggccatc   1200
aacttgatcc tggacgagct gtggcacacc aacgataacc agatcgctat tttcaatcgg   1260
ctgaagctgg tccccaagaa agtggacctc tcacaacaaa aggagatccc tactacccctt  1320
gtggacgatt tcattctgtc ccccgtggtc aagagaagct tcatacagtc aatcaaagtg   1380
atcaatgcca ttatcaagaa atacggtctg cccaacgaca ttatcattga gctcgcccgc   1440
gagaagaact cgaaggacgc ccagaagatg attaacgaaa tgcagaagag gaaccgacag   1500
actaacgaac ggatcgaaga atcatccgg accaccggga aggaaaacgc gaagtacctg    1560
atcgaaaaga tcaagctcca tgacatgcag gaaggaaagt gtctgtactc gctggaggcc   1620
attccgctgg aggacttgct gaacaaccct tttaactacg aagtggatca tatcattccg   1680
aggagcgtgt cattcgacaa ttccttcaac aacaaggtcc tcgtgaagca ggaggaaaac   1740
tcgaagaagg gaaaccgcac gccgttccag tacctgagca gcagcgactc caagatttcc   1800
tacgaaacct tcaagaagca catcctcaac ctggcaaagg ggaagggtcg catctccaag   1860
accaagaagg aatatctgct ggaagaaaga gacatcaaca gattctccgt gcaaaaggac   1920
ttcatcaacc gcaacctcgt ggatactaga tacgctactc ggggtctgat gaacctcctg   1980
agaagctact ttagagtgaa caatctggac gtgaaggtca agtcgattaa cggaggtttc   2040
```

-continued

| | | |
|---|---|---|
| acctccttcc tgcggcgcaa gtggaagttc aagaaggaac ggaacaaggg ctacaagcac | 2100 |
| cacgccgagg acgccctgat cattgccaac gccgacttca tcttcaaaga atggaagaaa | 2160 |
| cttgacaagg ctaagaaggt catggaaaac cagatgttcg aagaaaagca ggccgagtct | 2220 |
| atgcctgaaa tcgagactga acaggagtac aaggaaatct ttattacgcc acaccagatc | 2280 |
| aaacacatca aggatttcaa ggattacaag tactcacatc gcgtggacaa aaagccgaac | 2340 |
| agggaactga tcaacgacac cctctactcc acccggaagg atgacaaagg gaataccctc | 2400 |
| atcgtcaaca accttaacgg cctgtacgac aaggacaacg ataagctgaa gaagctcatt | 2460 |
| aacaagtcgc ccgaaaagtt gctgatgtac caccacgacc ctcagactta ccagaagctc | 2520 |
| aagctgatca tggagcagta tgggacgag aaaaacccgt tgtacaagta ctacgaagaa | 2580 |
| actgggaatt atctgactaa gtactccaag aaagataacg ccccgtgat taagaagatt | 2640 |
| aagtactacg gcaacaagct gaacgcccat ctggacatca ccgatgacta ccctaattcc | 2700 |
| cgcaacaagg tcgtcaagct gagcctcaag ccctaccggt ttgatgtgta ccttgacaat | 2760 |
| ggagtgtaca gttcgtgac tgtgaagaac cttgacgtga tcaagaagga gaactactac | 2820 |
| gaagtcaact ccaagtgcta cgaggaagca aagaagttga agaagatctc gaaccaggcc | 2880 |
| gagttcattg cctccttcta taacaacgac ctgattaaga tcaacggcga actgtaccgc | 2940 |
| gtcattggcg tgaacaacga tctcctgaac cgcatcgaag tgaacatgat cgacatcact | 3000 |
| taccgggaat acctggagaa tatgaacgac aagcgcccgc ccggatcat taagactatc | 3060 |
| gcctcaaaga cccagtcgat caagaagtac agcaccgaca tcctgggcaa cctgtacgag | 3120 |
| gtcaaatcga gaagcaccc ccagatcatc aagaaggga | 3159 |

<210> SEQ ID NO 35
<211> LENGTH: 3255
<212> TYPE: DNA
<213> ORGANISM: Staphylococcus aureus

<400> SEQUENCE: 35

| | | |
|---|---|---|
| atggccccaa agaagaagcg gaaggtcggt atccacggag tcccagcagc caagcggaac | 60 |
| tacatcctgg gcctggacat cggcatcacc agcgtgggct acggcatcat cgactacgag | 120 |
| acacgggacg tgatcgatgc cggcgtgcgg ctgttcaaag aggccaacgt ggaaaacaac | 180 |
| gagggcaggc ggagcaagag aggcgccaga aggctgaagc ggcggaggcg catagaatc | 240 |
| cagagagtga agaagctgct gttcgactac aacctgctga ccgaccacag cgagctgagc | 300 |
| ggcatcaacc cctacgaggc cagagtgaag ggcctgagcc agaagctgag cgaggaagag | 360 |
| ttctctgccg ccctgctgca cctggccaag agaagaggcg tgcacaacgt gaacgaggtg | 420 |
| gaagaggaca ccggcaacga gctgtccacc agagagcaga tcagccggaa cagcaaggcc | 480 |
| ctggaagaga atacgtggc cgaactgcag ctggaacggc tgaagaaaga cggcgaagtg | 540 |
| cggggcagca tcaacagatt caagaccagc gactacgtga agaagccaa acagctgctg | 600 |
| aaggtgcaga aggcctacca ccagctggac cagagcttca tcgacaccta catcgacctg | 660 |
| ctggaaaccc ggcggaccta ctatgaggga cctggcgagg cagccccctt cggctggaag | 720 |
| gacatcaaag aatggtacga gatgctgatg ggccactgca cctacttccc cgaggaactg | 780 |
| cggagcgtga agtacgccta caacgccgac ctgtacaacg ccctgaacga cctgaacaat | 840 |
| ctcgtgatca ccaggggacga gaacgagaag ctggaatatt acgagaagtt ccagatcatc | 900 |
| gagaacgtgt tcaagcagaa gaagaagccc accctgaagc agatcgccaa gaaaatcctc | 960 |
| gtgaacgaag aggatattaa gggctacaga gtgaccagca ccggcaagcc cgagttcacc | 1020 |

```
aacctgaagg tgtaccacga catcaaggac attaccgccc ggaaagagat tattgagaac   1080
gccgagctgc tggatcagat tgccaagatc ctgaccatct accagagcag cgaggacatc   1140
caggaagaac tgaccaatct gaactccgag ctgacccagg aagagatcga gcagatctct   1200
aatctgaagg gctataccgg cacccacaac ctgagcctga aggccatcaa cctgatcctg   1260
gacgagctgt ggcacaccaa cgacaaccag atcgctatct caaccggct gaagctggtg    1320 cccaagaagg tggacctgtc ccagcagaaa gagatcccca ccaccctggt ggacgacttc   1380
atcctgagcc ccgtcgtgaa gagaagcttc atccagagca tcaaagtgat caacgccatc   1440
atcaagaagt acggcctgcc caacgacatc attatcgagc tggcccgcga agaactcc     1500 aaggacgccc agaaaatgat caacgagatg cagaagcgga accggcagac caacgagcgg   1560
atcgaggaaa tcatccggac caccggcaaa gagaacgcca agtacctgat cgagaagatc   1620
aagctgcacg acatgcagga aggcaagtgc ctgtacagcc tggaagccat ccctctggaa   1680
gatctgctga caaccccctt caactatgag gtggaccaca tcatccccag aagcgtgtcc   1740
ttcgacaaca gcttcaacaa caaggtgctc gtgaagcagg aagaaaacag caagaagggc   1800
aaccggaccc cattccagta cctgagcagc agcgacagca agatcagcta cgaaaccttc   1860
aagaagcaca tcctgaatct ggccaagggc aagggcagaa tcagcaagac caagaaagag   1920
tatctgctgg aagaacggga catcaacagg ttctccgtgc agaaagactt catcaaccgg   1980
aacctggtgg ataccagata cgccaccaga ggcctgatga acctgctgcg gagctacttc   2040
agagtgaaca acctggacgt gaaagtgaag tccatcaatg gcggcttcac cagctttctg   2100
cggcggaagt ggaagtttaa gaaagagcgg aacaagggt acaagcacca cgccgaggac   2160
gccctgatca ttgccaacgc cgatttcatc ttcaaagagt ggaagaaact ggacaaggcc   2220
aaaaaagtga tggaaaacca gatgttcgag gaaaggcagg ccgagagcat gcccgagatc   2280
gaaaccgagc aggagtacaa agagatcttc atcacccccc accagatcaa gcacattaag   2340
gacttcaagg actacaagta cagccaccgg gtggacaaga gcctaatag agagctgatt   2400 aacgacaccc tgtactccac ccggaaggac gacaagggca cacccctgat cgtgaacaat   2460
ctgaacggcc tgtacgacaa ggacaatgac aagctgaaaa agctgatcaa caagagcccc   2520
gaaaagctgc tgatgtacca ccacgacccc cagacctacc agaaactgaa gctgattatg   2580
gaacagtacg gcgacgagaa gaatcccctg tacaagtact acgaggaaac cgggaactac   2640
ctgaccaagt actccaaaaa ggacaacggc cccgtgatca gaagattaa gtattacggc   2700 aacaaactga acgcccatct ggacatcacc gacgactacc ccaacagcag aaacaaggtc   2760
gtgaagctgt ccctgaagcc ctacagattc gacgtgtacc tggacaatgg cgtgtacaag   2820
ttcgtgaccg tgaagaatct ggatgtgatc aaaaagaaa actactacga agtgaatagc   2880
aagtgctatg aggaagctaa gaagctgaag aagatcagca accaggccga gtttatcgcc   2940
tccttctaca caacgatct gatcaagatc aacggcgagc tgtatagagt gatcggcgtg   3000
aacaacgacc tgctgaaccg gatcgaagtg aacatgatcg acatcaccta ccgcgagtac   3060
ctggaaaaca tgaacgacaa gaggcccccc aggatcatta agacaatcgc ctccaagacc   3120
cagagcatta agaagtacag cacagacatt ctgggcaacc tgtatgaagt gaaatctaag   3180
aagcaccctc agatcatcaa aaagggcaaa aggccggcgg ccacgaaaaa ggccggccag   3240
gcaaaaaaga aaaag                                                    3255

<210> SEQ ID NO 36
```

```
<211> LENGTH: 3242
<212> TYPE: DNA
<213> ORGANISM: Staphylococcus aureus

<400> SEQUENCE: 36
accggtgcca ccatgtaccc atacgatgtt ccagattacg cttcgccgaa gaaaaagcgc      60
aaggtcgaag cgtccatgaa aggaactac attctggggc tggacatcgg gattacaagc     120
gtggggtatg ggattattga ctatgaaaca agggacgtga tcgacgcagg cgtcagactg     180
ttcaaggagg ccaacgtgga aaacaatgag ggacggagaa gcaagagggg agccaggcgc     240
ctgaaacgac ggagaaggca cagaatccag agggtgaaga aactgctgtt cgattacaac     300
ctgctgaccg accattctga gctgagtgga attaatcctt atgaagccag ggtgaaaggc     360
ctgagtcaga agctgtcaga ggaagagttt tccgcagctc tgctgcacct ggctaagcgc     420
cgaggagtgc ataacgtcaa tgaggtggaa gaggacaccg caacgagct gtctacaaag     480 gaacagatct cacgcaatag caaagctctg gaagagaagt atgtcgcaga gctgcagctg     540
gaacggctga agaaagatgg cgaggtgaga gggtcaatta ataggttcaa gacaagcgac     600
tacgtcaaag aagccaagca gctgctgaaa gtgcagaagg cttaccacca gctggatcag     660
agcttcatcg atacttatat cgacctgctg gagactcgga gaacctacta tgagggacca     720
ggagaaggga gccccttcgg atggaaagac atcaaggaat ggtacgagat gctgatggga     780
cattgcacct attttccaga agagctgaga agcgtcaagt acgcttataa cgcagatctt     840
acaacgccct gaatgacctg aacaacctgg tcatcaccag ggatgaaaac gagaaactgg     900
aatactatga gaagttccag atcatcgaaa acgtgtttaa gcagaagaaa aagcctacac     960
tgaaacagat tgctaaggag atcctggtca acgaagagga catcaagggc taccgggtga    1020
caagcactgg aaaaccagag ttcaccaatc tgaaagtgta tcacgatatt aaggacatca    1080
cagcacggaa agaaatcatt gagaacgccg aactgctgga tcagattgct aagatcctga    1140
ctatctacca gagctccgag gacatccagg aagagctgac taacctgaac agcgagctga    1200
cccaggaaga gatcgaacag attagtaatc tgaaggggta caccggaaca cacaacctgt    1260
ccctgaaagc tatcaatctg attctggatg agctgtggca tacaaacgac aatcagattg    1320
caatctttaa ccggctgaag ctggtcccaa aaaaggtgga cctgagtcag cagaaagaga    1380
tcccaaccac actggtggac gatttcattc tgtcacccgt ggtcaagcgg agcttcatcc    1440
agagcatcaa agtgatcaac gccatcatca agaagtacgg cctgcccaat gatatcatta    1500
tcgagctggc tagggagaag aacagcaagg acgcacagaa gatgatcaat gagatgcaga    1560
aacgaaaccg gcagaccaat gaacgcattg aagagattat ccgaactacc gggaaagaga    1620
acgcaaagta cctgattgaa aaaatcaagc tgcacgatat gcaggaggga aagtgtctgt    1680
attctctgga ggccatcccc ctggaggacc tgctgaacaa tccattcaac tacgaggtcg    1740
atcatattat ccccagaagc gtgtccttcg acaattcctt taacaacaag gtgctggtca    1800
agcaggaaga gaactctaaa aagggcaata ggactccttt ccagtacctg tctagttcag    1860
attccaagat ctcttacgaa acctttaaaa agcacattct gaatctggcc aaaggaaagg    1920
gccgcatcag caagaccaaa aaggagtacc tgctggaaga gcgggacatc aacagattct    1980
ccgtccagaa ggattttatt aaccggaatc tggtggacac aagatacgct actcgcggcc    2040
tgatgaatct gctgcgatcc tatttccggg tgaacaatct ggatgtgaaa gtcaagtcca    2100
tcaacggcgg gttcacatct tttctgaggc gcaaatggaa gtttaaaaag gagcgcaaca    2160
aagggtacaa gcaccatgcc gaagatgctc tgattatcgc aaatgccgac ttcatcttta    2220
```

```
aggagtggaa aaagctggac aaagccaaga aagtgatgga gaaccagatg ttcgaagaga   2280
agcaggccga atctatgccc gaaatcgaga cagaacagga gtacaaggag attttcatca   2340
ctcctcacca gatcaagcat atcaaggatt tcaaggacta caagtactct caccgggtgg   2400
ataaaaagcc aacagagag ctgatcaatg cacccctgta tagtacaaga aaagacgata   2460
aggggaatac cctgattgtg aacaatctga acggactgta cgacaaagat aatgacaagc   2520
tgaaaaagct gatcaacaaa gtcccgaga agctgctgat gtaccaccat gatcctcaga   2580
catatcagaa actgaagctg attatggagc agtacggcga cgagaagaac ccactgtata   2640
agtactatga agagactggg aactacctga ccaagtatag caaaaaggat aatggccccg   2700
tgatcaagaa gatcaagtac tatgggaaca agctgaatgc ccatctggac atcacagacg   2760
attaccctaa cagtcgcaac aaggtggtca agctgtcact gaagccatac agattcgatg   2820
tctatctgga caacggcgtg tataaatttg tgactgtcaa gaatctggat gtcatcaaaa   2880
aggagaacta ctatgaagtg aatagcaagt gctacgaaga ggctaaaaag ctgaaaaaga   2940
ttagcaacca ggcagagttc atcgcctcct tttacaacaa cgacctgatt aagatcaatg   3000
gcgaactgta tagggtcatc ggggtgaaca atgatctgct gaaccgcatt gaagtgaata   3060
tgattgacat cacttaccga gagtatctgg aaaacatgaa tgataagcgc cccctcgaa   3120 ttatcaaaac aattgcctct aagactcaga gtatcaaaaa gtactcaacc gacattctgg   3180
gaaacctgta tgaggtgaag agcaaaaagc accctcagat tatcaaaaag ggctaagaat   3240
tc                                                                 3242
```

<210> SEQ ID NO 37
<211> LENGTH: 1053
<212> TYPE: PRT
<213> ORGANISM: Staphylococcus aureus

<400> SEQUENCE: 37

```
Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
```

```
                180                185                190
Leu Asp Gln Ser Phe Ile Asp Thr Tyr Ile Asp Leu Leu Glu Thr Arg
            195                200                205
Arg Thr Tyr Tyr Glu Gly Pro Gly Glu Gly Ser Pro Phe Gly Trp Lys
        210                215                220
Asp Ile Lys Glu Trp Tyr Glu Met Leu Met Gly His Cys Thr Tyr Phe
225                230                235                240
Pro Glu Glu Leu Arg Ser Val Lys Tyr Ala Tyr Asn Ala Asp Leu Tyr
                245                250                255
Asn Ala Leu Asn Asp Leu Asn Asn Leu Val Ile Thr Arg Asp Glu Asn
            260                265                270
Glu Lys Leu Glu Tyr Tyr Glu Lys Phe Gln Ile Ile Glu Asn Val Phe
        275                280                285
Lys Gln Lys Lys Lys Pro Thr Leu Lys Gln Ile Ala Lys Glu Ile Leu
                295                300
        290
Val Asn Glu Glu Asp Ile Lys Gly Tyr Arg Val Thr Ser Thr Gly Lys
305                310                315                320
Pro Glu Phe Thr Asn Leu Lys Val Tyr His Asp Ile Lys Asp Ile Thr
                325                330                335
Ala Arg Lys Glu Ile Ile Glu Asn Ala Glu Leu Leu Asp Gln Ile Ala
            340                345                350
Lys Ile Leu Thr Ile Tyr Gln Ser Ser Glu Asp Ile Gln Glu Glu Leu
        355                360                365
Thr Asn Leu Asn Ser Glu Leu Thr Gln Glu Glu Ile Glu Gln Ile Ser
    370                375                380
Asn Leu Lys Gly Tyr Thr Gly Thr His Asn Leu Ser Leu Lys Ala Ile
385                390                395                400
Asn Leu Ile Leu Asp Glu Leu Trp His Thr Asn Asp Asn Gln Ile Ala
                405                410                415
Ile Phe Asn Arg Leu Lys Leu Val Pro Lys Lys Val Asp Leu Ser Gln
            420                425                430
Gln Lys Glu Ile Pro Thr Thr Leu Val Asp Asp Phe Ile Leu Ser Pro
        435                440                445
Val Val Lys Arg Ser Phe Ile Gln Ser Ile Lys Val Ile Asn Ala Ile
    450                455                460
Ile Lys Lys Tyr Gly Leu Pro Asn Asp Ile Ile Ile Glu Leu Ala Arg
465                470                475                480
Glu Lys Asn Ser Lys Asp Ala Gln Lys Met Ile Asn Glu Met Gln Lys
                485                490                495
Arg Asn Arg Gln Thr Asn Glu Arg Ile Glu Glu Ile Ile Arg Thr Thr
            500                505                510
Gly Lys Glu Asn Ala Lys Tyr Leu Ile Glu Lys Ile Lys Leu His Asp
        515                520                525
Met Gln Glu Gly Lys Cys Leu Tyr Ser Leu Glu Ala Ile Pro Leu Glu
    530                535                540
Asp Leu Leu Asn Asn Pro Phe Asn Tyr Glu Val Asp His Ile Ile Pro
545                550                555                560
Arg Ser Val Ser Phe Asp Asn Ser Phe Asn Asn Lys Val Leu Val Lys
                565                570                575
Gln Glu Glu Asn Ser Lys Lys Gly Asn Arg Thr Pro Phe Gln Tyr Leu
            580                585                590
Ser Ser Ser Asp Ser Lys Ile Ser Tyr Glu Thr Phe Lys Lys His Ile
        595                600                605
```

```
Leu Asn Leu Ala Lys Gly Lys Gly Arg Ile Ser Lys Thr Lys Lys Glu
        610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
            675                 680                 685

Lys Phe Lys Lys Glu Arg Asn Lys Gly Tyr Lys His His Ala Glu Asp
690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
                740                 745                 750

Ile Phe Ile Thr Pro His Gln Ile Lys His Ile Lys Asp Phe Lys Asp
            755                 760                 765

Tyr Lys Tyr Ser His Arg Val Asp Lys Lys Pro Asn Arg Glu Leu Ile
770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
            835                 840                 845

Asp Glu Lys Asn Pro Leu Tyr Lys Tyr Tyr Glu Glu Thr Gly Asn Tyr
850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
            915                 920                 925

Lys Asn Leu Asp Val Ile Lys Lys Glu Asn Tyr Tyr Glu Val Asn Ser
930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
            995                 1000                1005

Asn Asp Lys Arg Pro Pro Arg Ile Ile Lys Thr Ile Ala Ser Lys
    1010                1015                1020
```

```
Thr Gln Ser Ile Lys Lys Tyr Ser Thr Asp Ile Leu Gly Asn Leu
    1025                1030                1035

Tyr Glu Val Lys Ser Lys Lys His Pro Gln Ile Ile Lys Lys Gly
    1040                1045                1050

<210> SEQ ID NO 38
<211> LENGTH: 20
<212> TYPE: RNA
<213> ORGANISM: Artificial Sequence
<220> FEATURE:
<223> OTHER INFORMATION: Synthetic

<400> SEQUENCE: 38
gauauuuccu uguaacuagu                                                   20

<210> SEQ ID NO 39
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 39 nngrrn                                                                   6
```

CRISPR/CAS-RELATED METHODS AND COMPOSITIONS FOR TREATING HERPES SIMPLEX VIRUS

CROSS-REFERENCE TO RELATED APPLICATIONS

This application is a Continuation of International Application No. PCT/US17/58670 filed Oct. 27, 2017, which claims priority to U.S. Provisional Application No. 62/414,561, filed Oct. 28, 2016, the contents of each of which are incorporated by reference in their entireties, and to each of which priority is claimed.

GRANT INFORMATION

This invention was made with government support under 1R43AI120302-01 awarded by the National Institutes of Health. The government has certain rights in the invention.

TECHNICAL FIELD

The present disclosure relates to the field of gene expression alteration, genome engineering and genomic alteration of genes using Clustered Regularly Interspaced Short Palindromic Repeats (CRISPR)/CRISPR-associated (Cas) 9-based systems and viral delivery systems. The present disclosure also relates to the field of genome engineering and genomic alteration of one or more herpes simplex virus (HSV) viral gene, e.g., UL19, UL30, UL48, UL54, RS1, RL2, and/or LAT genes.

SEQUENCE LISTING

The specification further incorporates by reference the Sequence Listing submitted herewith via EFS on Apr. 26, 2019. Pursuant to 37 C.F.R. § 1.52(e)(5), the Sequence Listing text file, identified as 0841770217SL.txt, is 85,970 bytes and was created on Apr. 26, 2019. The entire contents of the Sequence Listing are hereby incorporated by reference. The Sequence Listing does not extend beyond the scope of the specification and thus does not contain new matter.

BACKGROUND

Herpes simplex virus (HSV), e.g., herpes simplex virus type 1 (HSV-1) and herpes simplex virus type 2 (HSV-2), is a ubiquitous and highly contagious pathogen. HSV-1 generally causes intermittent, painful blistering of the mouth and mucous membranes. HSV-2 generally causes intermittent, painful blistering in the genital region. HSV can cause lifelong, recurring bouts of viral reactivity. Infection with HSV-1 and/or HSV-2 is permanent. After initial infection with HSV-1 or HSV-2, the virus establishes latent infection that lasts for the lifetime of the host. Initial infection with HSV-1 generally causes painful blistering of the mucous membranes of the mouth, including the lips, mouth and nose. HSV-1 initial infection less commonly affects the anogenital region, causing painful blistering of the mucous membranes of the genital and anal region. Initial infection with HSV-2 generally causes painful blistering of the mucous membranes of the anogenital region. HSV-2 initial infection less commonly affects the mouth, causing painful blistering of the mucous membranes of the lips, mouth and nose.

Following establishment of latent infection, reactivation of HSV-1 or HSV-2 can occur at any point during the lifetime of the subject. Reactivation of HSV-1 or HSV-2 is more likely to occur in the elderly and in immunocompromised individuals, including in those who have cancer, those who have HIV/AIDs and in those who have undergone solid organ or hematopoietic stem cell transplant. HSV-1 and HSV-2 both cause ocular herpes. Historically, HSV-1 has been the causative agent in the majority of ocular herpes infections. However, HSV-2 related ocular infections have been increasing in incidence worldwide over the recent years.

Ocular infection with HSV-1 or HSV-2 can affect the epithelium of the eye, causing keratitis. Ocular herpes may also affect the retina, causing retinitis.

There are no curative or preventative treatments for HSV-1 or HSV-2. Therapy is primarily given during acute infection. Primary HSV-1 or HSV-2 infections can be treated with antiviral therapy, including acyclovir, valacyclovir and famciclovir. However, in controlled clinical trials, vaccination efficacy has been limited. A recent vaccine for both HSV-1 and HSV-2 infections was only 35% effective in preventing HSV-1 infections (Belshe et al., 2012; New England Journal of Medicine 366(1): 34-43). Despite advances in antiretroviral therapies, there remains a need for the treatment and prevention of HSV-1 and HSV-2 infections, particularly the treatment and prevention of HSV-1 and HSV-2 associated ocular infections, including keratitis and retinitis. A therapy that can cure, prevent, or treat HSV-1 and HSV-2 ocular infections would be superior to the current standard of care.

SUMMARY OF THE INVENTION

The presently disclosed subject matter provides a vector encoding a guide RNA (gRNA) molecule and one Cas9 molecule, wherein the gRNA molecule comprises a targeting domain comprising the nucleotide sequence selected from SEQ ID NOS: 1 to 23. In certain embodiments, the vector is a viral vector. In addition, the presently disclosed subject matter provides a composition comprising the vector described herein.

Furthermore, the presently disclosed subject matter provides a genome editing system comprising: (a) a gRNA molecule comprising a targeting domain that comprises the nucleotide sequence selected from SEQ ID NOS: 1 to 23, (b) a Cas9 molecule.

In certain embodiments, the vector or genome editing system is configured to alter a HSV viral gene selected from the group consisting of a UL19 gene, a UL30 gene, a UL48 gene, a UL54 gene, a RS1 gene, or a RL2 gene. In certain embodiments, the Cas9 molecule is an *S. aureus* Cas9 molecule. In certain embodiments the Cas9 molecule recognizes a Protospacer Adjacent Motif (PAM) of either NNGRRT (SEQ ID NO: 24) or NNGRRV (SEQ ID NO: 25).

The presently disclosed subject matter also provides cells comprising the vector or genome editing system describe herein.

In certain embodiments, the vector or genome editing system is used in reducing or preventing herpes simplex virus (HSV) infection in a cell.

The presently disclosed subject matter further provides a method of reducing or preventing HSV infection in a cell, comprising administering to the cell: (a) a vector encoding a gRNA molecule and one Cas9 molecule; or (b) a genome editing system comprising a gRNA molecule and a Cas9 molecule; wherein the gRNA molecule comprises a targeting domain comprising the nucleotide sequence selected from SEQ ID NOS: 1 to 23.

In certain embodiments, the cell is infected with HSV. In certain embodiments, the HSV infection is HSV-1 infection. In certain embodiments, the cell is selected from the group consisting of an epithelial cell, a neuronal cell and an optic cell.

In certain embodiments, the gRNA comprises a targeting domain comprises a nucleotide sequence selected from the group consisting of: SEQ ID NOS: 2, 6, 10, 15 and 16.

BRIEF DESCRIPTION OF THE DRAWINGS

FIG. 1 depicts the efficiency of plasmids encoding a Cas9 molecule and a presently disclosed gRNA molecule for reducing HSV-1 infection in HEK293T cells.

DETAILED DESCRIPTION

The genome editing systems, genetic constructs (e.g., vectors), compositions and methods described herein can be used for editing (altering) one or more HSV viral gene, e.g., UL19, UL30, UL48, UL54, RS1, and/or RL2 genes, thereby preventing, treating and/or reducing HSV infection in a cell or a subject. The genome editing systems or genetic constructs (e.g., vectors) comprise one guide RNA molecule that provide the DNA targeting specificity for the HSV viral gene, and a Cas9 molecule.

For purposes of clarity of disclosure and not by way of limitation, the detailed description is divided into the following subsections:

1. Definitions
2. Herpes Simplex Virus
3. Methods to Reduce and/or Prevent HSV Infection in Cells
4. Methods to Treat, Prevent and/or Reduce HSV-related Ocular Infection
5. Methods of Altering HSV viral gene(s)
6. Guide RNA (gRNA) Molecules
7. Genome Editing Systems Targeting HSV Viral Genes
8. Genetic Constructs for Genome Editing of HSV Viral Genes
9. Compositions
10. Target Cells
11. Delivery, Formulations and Routes of Administration

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the presently disclosed subject matter. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of", and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

"Target gene" as used herein, refers to any nucleotide sequence encoding a known or putative gene product. In certain embodiments, the target gene is a HSV viral gene. As used herein, a "HSV viral gene" refers to a (HSV-1 or HSV-2) UL19 gene, a (HSV-1 or HSV-2) UL30 gene, a (HSV-1 or HSV-2) UL48 gene, a (HSV-1 or HSV-2) UL54 gene, a (HSV-1 or HSV-2) RS1 gene, a (HSV-1 or HSV-2) RL2 gene, or a (HSV-1 or HSV-2) LAT gene. In certain embodiments, the target gene is a HSV-1 UL19 gene. In certain embodiments, the target gene is a HSV-1 UL30 gene. In certain embodiments, the target gene is a HSV-1 UL48 gene. In certain embodiments, the target gene is a HSV-1 UL54 gene. In certain embodiments, the target gene is a HSV-1 RS1 gene. In certain embodiments, the target gene is a HSV-1 RL2 gene. In certain embodiments, the target gene is a HSV-1 LAT gene.

As used herein, a "genome editing system" refers to any system having RNA-guided DNA editing activity. Genome editing systems of the present disclosure include at least two components adapted from naturally occurring CRISPR systems: a guide RNA (gRNA) and an RNA-guided nuclease. These two components form a complex that is capable of associating with a specific nucleic acid sequence in a cell and editing the DNA in or around that nucleic acid sequence, for instance by making one or more of a single-strand break (an SSB or nick), a double-strand break (a DSB) and/or a point mutation.

Genome editing systems may comprise, in various embodiments, (a) one or more Cas9/gRNA complexes, and (b) separate Cas9 molecules and gRNAs that are capable of associating in a cell to form one or more Cas9/gRNA complexes. A genome editing system according to the present disclosure may be encoded by one or more nucleotides (e.g. RNA, DNA) comprising coding sequences for Cas9 and/or gRNAs that can associate to form a Cas9/gRNA complex, and the one or more nucleotides encoding the gene editing system may be carried by a vector as described herein.

In certain embodiments, the genome editing system targets a HSV viral gene selected from the group consisting of a (HSV-1 or HSV-2) UL19 gene, a (HSV-1 or HSV-2) UL30 gene, a (HSV-1 or HSV-2) UL48 gene, a (HSV-1 or HSV-2) UL54 gene, a (HSV-1 or HSV-2) RS1 gene, a (HSV-1 or HSV-2) RL2 gene, and a (HSV-1 or HSV-2) LAT gene. In certain embodiments, the UL19 gene is a HSV-1 UL19 gene. In certain embodiments, the UL30 gene is a HSV-1 UL30 gene. In certain embodiments, the UL48 gene is a HSV-1 UL48 gene. In certain embodiments, the UL54 gene is a HSV-1 UL54 gene. In certain embodiments, the RS1 gene is a HSV-1 RS1 gene. In certain embodiments, the RL2 gene is a HSV-1 RL2 gene. In certain embodiments, the LAT gene is a HSV-1 LAT gene.

In certain embodiments, the genome editing system is implemented in a cell in an in vivo contact. In certain embodiments, the genome editing system is implemented in a cell in an in vitro contact. In certain embodiments, the genome editing system is used in a medicament, e.g., a medicament for modifying (knocking down or knocking out) one or more target genes (e.g., one or more HSV viral gene selected from the group consisting of a (HSV-1 or HSV-2) UL19 gene, a (HSV-1 or HSV-2) UL30 gene, a (HSV-1 or HSV-2) UL48 gene, a (HSV-1 or HSV-2) UL54 gene, a (HSV-1 or HSV-2) RS1 gene, a (HSV-1 or HSV-2) RL2 gene), and a (HSV-1 or HSV-2) LAT gene, or a medicament for treating, preventing, or reducing HSV infection (HSV-1 or HSV-2 infection). In certain embodiments, the genome editing system is used in therapy.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered.

A "Cas9 molecule" or "Cas9 polypeptide" as used herein refers to a molecule or polypeptide, respectively, that can interact with a gRNA molecule and, in concert with the gRNA molecule, localize to a site comprising a target domain (also referred to as "target sequence") and, in certain embodiments, a PAM sequence. Cas9 molecules and Cas9 polypeptides include both naturally occurring Cas9 molecules and Cas9 polypeptides and engineered, altered, or modified Cas9 molecules or Cas9 polypeptides that differ, e.g., by at least one amino acid residue, from a reference sequence, e.g., the most similar naturally occurring Cas9 molecule.

In certain embodiments, the Cas9 molecule is a wild-type *S. pyogenes* Cas9, which recognizes a NGG PAM sequence. In certain embodiments, the Cas9 molecule is an *S. pyogenes* Cas9 EQR variant, which recognizes a NGAG PAM sequence, a NGCG PAM sequence, a NGGG PAM sequence, a NGTG PAM sequence, a NGAA PAM sequence, a NGAT PAM sequence or a NGAC PAM sequence. In certain embodiments, the Cas9 molecule is an *S. pyogenes* Cas9 VRER variant, which recognizes a NGCG PAM sequence, a NGCA PAM sequence, a NGCT PAM sequence, or a NGCC PAM sequence. In certain embodiments, the Cas9 molecule is a wild-type *S. aureus* Cas9, which recognizes a NNGRRT PAM sequence, or a NNGRRV PAM sequence.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids can be single stranded or double stranded, or may contain portions of both double stranded and single stranded sequence. The nucleic acid can be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which may be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In certain embodiments, the subject is a human. The subject or patient can be undergoing other forms of treatment.

"Treat", "treating" and "treatment", as used herein, refers to the treatment of a disease in a mammal, e.g., in a human, including (a) inhibiting the disease, i.e., arresting or preventing its development or progression; (b) relieving the disease, i.e., causing regression of the disease state; (c) relieving one or more symptoms of the disease; and (d) curing the disease.

"Prevent," "preventing," and "prevention" as used herein, refers to the prevention of a disease in a mammal, e.g., in a human, including (a) avoiding or precluding the disease; (b) affecting the predisposition toward the disease; (c) preventing or delaying the onset of at least one symptom of the disease.

"Vector" as used herein means a nucleic acid sequence containing an origin of replication. A vector can be a viral vector, bacteriophage, bacterial artificial chromosome or yeast artificial chromosome. A vector can be a DNA or RA vector. A vector can be a self-replicating extrachromosomal vector, e.g., a DNA plasmid. For example, the vector can encode one Cas9 molecule and a pair of gRNA molecules.

2. Herpes Simplex Virus

Herpes simplex viruses (HSVs) are categorized into at least two types: herpes simplex virus type 1 (HSV-1) and herpes simplex virus type 2 (HSV-2). HSV-1 and HSV-2 are also known as human herpesvirus 1 (HHV-1) and human herpesvirus (HHV-2), respectively.

The structure of herpes viruses includes a relatively large double-stranded, linear DNA genome encased within an icosahedral protein cage (capsid), which is wrapped in a lipid bilayer called (envelope). The envelope is joined to the capsid by means of a tegument. This complete particle is known as the virion (Mettenleiter et al. (2006) Curr. Opin. Microbiol. 9 (4): 423-429). HSV-1 and HSV-2 each contain at least 74 genes (or open reading frames, ORFs), or even as many as 84 unique protein coding genes by 94 putative ORFs, within their genomes (McGeoch et al. (2006) Virus Res. 117 (1): 90-104; Rajcáni et al. (2004) Virus Genes 28 (3): 293-310). These genes encode a variety of proteins involved in forming the capsid, tegument and envelope of the virus, as well as controlling the replication and infectivity of the virus.

The genomes of HSV-1 and HSV-2 are complex and contain two unique regions, i.e., the long unique region (UL) and the short unique region (US), each containing multiple viral genes. Immediate early genes encode, e.g., proteins that regulate the expression of early and late viral genes. Early genes encode, e.g., enzymes involved in DNA replication and the production of certain envelope glycoproteins. Late genes encode, e.g., proteins that form the virion particle. Transcription of HSV genes is catalyzed by RNA polymerase II of the infected host (McGeoch et al. (2006) Virus Res. 117 (1): 90-104).

Entry of HSV into the host cell involves interactions of several glycoproteins (e.g., glycoprotein B (gB), glycoprotein C (gC), glycoprogein D (gD), glycoprotein H (gH), and glycoprotein L (gL)) on the surface of the enveloped virus, with receptors (e.g., herpesvirus entry mediator (HVEM), nectin-1, or 3-O sulfated heparan sulfate) on the surface of the host cell. The envelope, when bound to specific receptors on the cell surface, will fuse with the host cell membrane and create a pore, through which the virus enters the host cell. The virus can also be endocytosed after binding to the receptors, and the fusion could occur at the endosome. After the viral capsid enters the cellular cytoplasm, it is transported to the cell nucleus. Once attached to the nucleus at a nuclear entry pore, the capsid ejects its DNA contents via the capsid portal. Following infection of a cell, a cascade of herpes virus proteins, e.g., immediate-early, early, and late, are produced.

HSVs may persist in a quiescent but persistent form known as latent infection. During latent infection of a cell, HSVs express Latency Associated Transcript (LAT) RNA. LAT can regulate the host cell genome and interfere with natural cell death mechanisms. By maintaining the host cells, LAT expression preserves a reservoir of the virus, which allows subsequent, usually symptomatic, periodic recurrences or "outbreaks" characteristic of non-latency. Whether or not recurrences are symptomatic, viral shedding occurs to produce further infections. Herpes virus DNA contains a gene that encodes ICP4, which is a transactivator of genes associated with lytic infection (Pinnoji et al. (2007) Virol. J. 4: 56). The human neuronal protein Neuronal Restrictive Silencing Factor (NRSF) or human Repressor Element Silencing Transcription Factor (REST) can bind to the elements surrounding the ICP4 gene and lead to histone deacetylation, which prevents initiation of transcription from this gene, thereby preventing transcription of other viral genes involved in the lytic cycle (Pinnoji et al. (2007) Virol. J. 4: 56; Bedadala et al. (2007) Cell Res. 17 (6): 546-555). The inhibition of ICP4 protein synthesis can be reversed by viral protein ICP0, which dissociates NRSF from the ICP4 gene and thus prevents silencing of the viral DNA (Roizman et al. (2005) Cell Cycle 4 (8): 1019-21).

2.1 HSV-Infections

The herpes simplex viruses enter the host via infection of epithelial cells within the skin and mucous membranes. Most commonly, HSV-1 enters the host via infection of epithelial cells of the oropharynx, including the epithelium of the mouth, lips and nose. Most commonly, HSV-2 enters the host via infection of epithelial cells of the anogenital region, including the epithelium of the genitals and anus. However, HSV-1 can primarily infect the anogenital region and HSV-2 can primarily infect the oropharynx.

HSV-1 causes intermittent sores of the mouth and mucous membranes. It is a ubiquitous and highly contagious pathogen. Initial infection with HSV-1 generally causes painful blistering of the mucous membranes of the lips and mouth.

HSV-2 is a sexually transmitted virus. It is most commonly known as genital herpes. Initial infection with HSV-2 generally causes painful blistering in the genital region. The disease causes lifelong, recurring bouts of viral reactivity. It is highly contagious and increases the risk of acquiring HIV infection, especially among patients with active lesions.

HSV-1 and HSV-2 infections persist for the lifetime of the host. During primary infection, the virus most often infects cells of the oropharynx and ano-genital region, causing painful vesicles in the affected region. Re-activation of HSV infections most often occurs in the oropharynx or ano-genital region. However, re-activation infections of the eye and central nervous system are the most severe and damaging HSV manifestations, as they can lead to blindness and permanent neurologic disability, respectively. Primary and re-activation infections can cause permanent neurologic sequelae and blindness. HSV-2 also increases a subject's risk of developing HIV. There is a considerable need for methods to treat and prevent HSV-1 and/or HSV-2 infections.

The herpes simplex virus produces immediate early genes within the epithelial cells, which encode enzymes and binding proteins necessary for viral synthesis. After primary infection, the virus travels up sensory nerve axons via retrograde transport to the sensory dorsal root ganglion (DRG). HSV-1 mainly travels to the trigeminal DRG, but can travel to other sensory ganglia depending upon the site of primary infection. HSV-2 mainly travels to the sensory DRG located within the sacrum, but can travel to other sensory ganglia depending upon the site of primary infection. Within the DRG, the virus establishes a latent infection. The latent infection persists for the lifetime of the host. Within the DRG cell, the virus uncoats, viral DNA is transported into the nucleus, and key viral RNAs associated with latency are transcribed (including the LAT RNAs).

During the primary infection, subjects generally experience painful blistering in the oral or ano-genital region that lasts 4-15 days. The sores most commonly involve the lips, gums and nasal mucous membranes in HSV-1 primary infections. Less commonly, HSV-1 primary infections may involve the ano-genital region. HSV-2 primary infections most commonly involve the ano-genital region, including the vagina, labia, cervix, penis, scrotum, anus and skin around the thighs. Less commonly, HSV-2 primary infections involve the oropharynx. Rarely, HSV-1 and HSV-2 primary infections may involve the eyes, central nervous system, the fingers and fingernail beds (herpetic whitlow). HSV-1 infection is transmitted primarily through saliva and/or sexual activity. HSV-2 infection is transmitted primarily through sexual activity but may also be transmitted through saliva. The blisters of an HSV infection may break, releasing clear fluid that is highly infectious. Primary infection is often accompanied by a flu-like illness, including fever, chills and muscle aches.

Host immune defense is very important to combating HSV infection. CD4+ T-cells and CD8+ cells are responsible for recognizing and clearing the pathogen. Subjects with impaired T-cell responses, including those with HIV, those receiving immunosuppressants following organ transplants, and neonates with developing immune systems, are subject to the most severe manifestations of HSV-1 and HSV-2 infections.

Reactivations of latent infections are generally less severe and may be of shorter duration. Reactivation of HSV-1 infection most often affects the oral region, but can also affect other areas, including the ano-genital region, the eye, the central nervous system (CNS), the fingernails, and the pharynx. Reactivation of HSV-2 infection most often affects the ano-genital region, but can also affect other areas, including the oral region, the eye, the central nervous system (CNS), the fingernails, and the pharynx. Reactivation of either HSV-1 or HSV-2 infection can cause ophthalmologic disease, including keratitis (epithelial keratitis, stromal keratitis and disciform keratitis). Generally, ophthalmologic manifestations of HSV-1 and HSV-2 include pain, tearing, redness of the eyes and sensitivity to light. Most HSV-related ocular infections resolve without permanent visual damage. However, ocular herpes infections may rarely cause scarring, secondary infection with bacterial pathogens and rarely, blindness. Reactivation of either HSV-1 or HSV-2 infection can also cause retinitis. HSV-associated retinitis is rare but severe and carries a high risk of permanent blindness.

Newborns are a population at particular risk for developing severe HSV-1 and HSV-2 infections. The disease is transmitted from the mother to the fetus during childbirth. The chance of maternal-fetal transmission is highest in cases where the mother developed primary HSV infection during pregnancy. The incidence of neonatal herpes is approximately 4-30 per 100,000 births. Neonates may develop severe HSV-1 or HSV-2 encephalitis and/or meningitis. In spite of prompt treatment with antiviral therapy, the rate of permanent neurologic sequelae in newborns infected with HSV-1 or HSV-2 is significant. In a study of infants with HSV-encephalitis or meningitis treated with high dose antiviral therapy, there was found to be a 4% mortality rate and 69% of survivors had permanent neurologic sequelae (Kimberlin et al., Pediatrics. 2001; 108: 230-238).

Primary HSV-1 and HSV-2 infections may be treated with antiviral therapy, including acyclovir, valacyclovir and famciclovir. These therapies have been demonstrated to reduce viral shedding, decrease pain and improve healing time of lesions. Re-activation of latent infections may resolve without treatment (it may be self-limiting) or may be treated with anti-viral therapy. Therapy is primarily given during acute infection. There are no curative or preventative treatments. Therapy may be given prophylactically in certain situations, including during childbirth in a mother with a recent HSV-1 or HSV-2 infection or reactivation.

There is no effective therapy that prevents HSV-1 or HSV-2 infection. The use of antiviral therapy during active infection and the use of condoms decrease transmission rates by approximately 50%.

Human immunodeficiency virus-1 (HIV-1) acquisition rates are dramatically increased in subjects who are seropositive for HSV-2. The risk of infection with HIV-1 is 3-fold higher in subjects with HSV-2. Antivirals have no impact on reducing risk of HIV acquisition.

2.2 HSV-Related Ocular Disease

HSV infections, e.g., HSV-1 and/or HSV-2 infections of the eye, either primary or reactivation infections, are called HSV-related ocular disease. HSV-related ocular disease most commonly causes infection of the anterior chamber of the eye, known as keratitis, stromal keratitis and/or disciform keratitis. HSV-related ocular disease may, more rarely, cause infection of the posterior chamber of the eye, known as retinitis. HSV-1 keratitis is acutely painful and unpleasant. It may, in rare instances, cause scarring, secondary infection with bacterial pathogens and rarely, blindness. HSV-related retinitis is a rare manifestation of HSV-related ocular disease but carries a much higher risk of permanent visual damage.

Reactivation infections occur in the eye via anterograde transport of the virus into the eye from the trigeminal ganglion, along the ophthalmic branch of the trigeminal nerve (the fifth cranial nerve) and into the eye. Re-activation of the virus may also occur from within the cornea. Latency within the trigeminal ganglion is established via one of two mechanisms. First, HSV-1 or HSV-2 can travel via retrograde transport along the trigeminal nerve from the eye (after an eye infection) into the trigeminal ganglion. Alternatively, it can spread to the trigeminal ganglion via hematogenous spread following infection of the oral mucosa, genital region, or other extraocular site. After establishing latent infection of the trigeminal ganglion, at any time, particularly in the event of an immunocompromised host, the virus can re-establish infection by traveling anterograde along the trigeminal nerve and into the eye.

When ocular herpes affects the posterior chamber of the eye, it causes retinitis. In adults, HSV-1 is responsible for the majority of cases of HSV-retinitis (Pepose et al., Ocular Infection and Immunity 1996; Mosby 1155-1168). In neonates and children, HSV-2 is responsible for the majority of cases of HSV-retinitis (Pepose et al., Ocular Infection and Immunity 1996; Mosby 1155-1168). HSV-related retinitis can lead to acute retinal necrosis (ARN), which will destroy the retina within 2 weeks without treatment (Banerjee and Rouse, Human Herpesviruses 2007; Cambridge University Press, Chapter 35). Even with treatment, the risk of permanent visual damage following ARN is higher than 50% (Roy et al., Ocular Immunology and Inflammation 2014; 22(3): 170-174).

Keratitis is the most common form of ocular herpes. HSV keratitis can manifest as dentritic keratitis, stromal keratitis, blepharatis and conjunctivitis. HSV-1 is responsible for the majority of HSV-associated keratitis, accounting for 58% of cases (Dawson et. al., Suvey of Ophthalmology 1976; 21(2): 121-135). HSV-2 accounts for the remainder of HSV-associated keratitis cases, or approximately 42% of cases. In the U.S., there are approximately 48,000 cases of recurrent or primary HSV-related keratitis infections annually (Liesegang et. al., 1989; 107(8): 1155-1159). Of all cases of HSV-related keratitis, approximately 1.5-3% of subjects experience severe, permanent visual impairment (Wilhelmus et. al., Archives of Ophthalmology 1981; 99(9): 1578-82). The risk to a subject of permanent visual damage due to HSV-related ocular disease increases with increasing numbers of ocular related HSV-reactivations.

Overall, stromal keratitis represents approximately 15% of keratitis cases and is associated with the highest risk of permanent visual damage from keratitis. Stromal keratitis results in scarring and irregular astimagtism. Previous ocular HSV infection increases the risk for developing stromal infection, which means that subjects who have had a prior ocular HSV infection have an increased risk for permanent visual damage on reactivation. In children, stromal keratitis represents up to 60% of all keratitis cases. Therefore, children are particularly at risk for permanent visual damage from HSV-associated keratitis. A retrospective study in the U.S. from 1950-1982 found that there are approximately 2.6 new or recurrent stromal keratitis cases per 100,000 person years, or approximately 8,000 cases of stromal keratitis annually (Liesegang et. al., 1989; 107(8): 1155-1159). A more recent study in France in 2002 estimated the incidence of new or recurrent stromal keratitis cases to be 9.6 per 100,000 (Labetoulle et al., Ophthalmology 2005; 112(5): 888-895). The incidence of HSV-associated keratitis may be increasing in the developed world (Farooq and Shukla 2012; Survey of Ophthalmology 57(5): 448-462).

The genome editing systems, genetic constructs (e.g., vectors), and compositions described herein can be used for treating, preventing, or reducing HSV-1 and/or HSV-2 ocular infections, including but not limited to HSV-1 stromal keratitis, HSV-1 dentritic keratitis, HSV-1 blepharatis, HSV-1 conjunctivitis, HSV-1 retinitis, HSV-2 stromal keratitis, HSV-2 dentritic keratitis, HSV-2 blepharatis, HSV-2 conjunctivitis, and HSV-2 retinitis.

3. Methods to Reduce and/or Prevent HSV Infection in Cells

The presently disclosed subject matter provides methods for reducing and/or preventing HSV infection in a cell. In certain embodiments, the cell is infected with HSV (HSV-1 and/or HSV-2 infection). In certain embodiments, the HSV infection is HSV-1 infection. In certain embodiments, the HSV infection is HSV-2 infection.

In certain embodiments, the method comprises administering to a tissue of a subject a presently disclosed genome editing system, genetic construct (e.g., a vector), or a composition.

In certain embodiments, the method comprises administering to the cell a presently disclosed genetic construct (e.g., a vector), which encodes a gRNA molecule and one Cas9 molecule. In certain embodiments, the method comprises administering to the cell a presently disclosed genome editing system comprising a gRNA molecule and a Cas9 molecule.

In certain embodiments, the gRNA molecule comprises a targeting domain comprising the nucleotide sequence selected from SEQ ID NOS: 1 to 23. In certain embodiments, the targeting domain comprises a nucleotide sequence selected from the group consisting of: SEQ ID NOS: 2, 6, 10, 15 and 16.

The UL19, UL30, UL48, UL54, RS1, RL2, and LAT genes of HSV-1 and HSV-2 are associated with viral infection, proliferation and assembly, as well as maintenance of latency and re-activation of the virus from latency. Knockout or knockdown of any of these genes singly or in combination can reduce and/or prevent HSV-1 and/or HSV-2 infections.

In certain embodiments, the method comprises knocking out or knocking down one or more HSV viral gene, e.g., UL19, UL30, UL48, UL54, RS1, RL2, and/or LAT genes.

In certain embodiments, knockout or knockdown of one or more of the UL19, UL30, UL48, UL54, RS1, RL2, and/or LAT genes inhibits viral functions, including, e.g., viral gene regulation, viral gene transcription, viral genome replication, expression of viral latency genes and viral capsid formation.

In certain embodiments, knockout or knockdown of the UL19, UL30, UL48, UL54, RS1, RL2, and/or LAT gene disables HSV-1 and/or HSV-2 gene expression, or reduces one or more of viral replication, assembly, maturation, packaging, or infection. In certain embodiments, knockout of UL19, UL30, UL48, UL54, RS1, RL2, and/or LAT gene expression shortens the duration of HSV-1 and/or HSV-2 infections. In certain embodiments, knockout or knockdown of UL19, UL30, UL48, UL54, RS1, RL2, and/or LAT gene expression reduces and/or prevents HSV-1 and/or HSV-2 infections.

In certain embodiments, inhibiting one or more viral functions, e.g., viral gene regulation, viral gene transcription, viral genome replication and viral capsid formation, decreases the duration of primary or recurrent infection and/or decreases shedding of viral particles.

In certain embodiments, the method comprises knocking down one HSV-1 and/or HSV-2 gene (e.g., UL19, UL30, UL48, UL54, RS1, RL2, or LAT gene). In certain embodiments, the method comprises knocking out two HSV-1 and/or HSV-2 genes, e.g., two of the UL19, UL30, UL48, UL54, RS1, RL2, and LAT genes. In certain embodiments, the method comprises knocking down two HSV-1 and/or HSV-2 genes, e.g., two of the UL19, UL30, UL48, UL54, RS1, RL2, and LAT genes. In certain embodiments, the method comprises knocking out three HSV-1 and/or HSV-2 genes, e.g., three of the UL19, UL30, UL48, UL54, RS1, RL2, and LAT genes. In certain embodiments, the method comprises knocking down three HSV-1 and/or HSV-2 genes, e.g., three of the UL19, UL30, UL48, UL54, RS1, RL2, and LAT genes. In certain embodiments, the method comprises knocking out four HSV-1 and/or HSV-2 genes, e.g., four of the UL19, UL30, UL48, UL54, RS1, RL2, and LAT genes. In certain embodiments, the method comprises knocking down four HSV-1 and/or HSV-2 genes, e.g., four of the UL19, UL30, UL48, UL54, RS1, RL2, and LAT genes. In certain embodiments, the method comprises knocking out five HSV-1 and/or HSV-2 genes, e.g., five of the UL19, UL30, UL48, UL54, RS1, RL2, and LAT genes. In certain embodiments, the method comprises knocking down five HSV-1 and/or HSV-2 genes, e.g., five of the UL19, UL30, UL48, UL54, RS1, RL2, and LAT genes. In certain embodiments, the method comprises knocking out six HSV-1 and/or HSV-2 genes, e.g., six of the UL19, UL30, UL48, UL54, RS1, RL2, and LAT genes. In certain embodiments, the method comprises knocking down six HSV-1 and/or HSV-2 genes, e.g., all six of the UL19, UL30, UL48, UL54, RS1, RL2, and LAT genes. In certain embodiments, the method comprises knocking out seven HSV-1 and/or HSV-2 genes, e.g., six of the UL19, UL30, UL48, UL54, RS1, RL2, and LAT genes. In certain embodiments, the method comprises knocking down seven HSV-1 and/or HSV-2 genes, e.g., all six of the UL19, UL30, UL48, UL54, RS1, RL2, and LAT genes.

When there are two alterations events (e.g., knocking down or knocking out the expression of the UL19, UL30, UL48, UL54, RS1, RL2, and/or LAT gene), the two alteration events may occur sequentially or simultaneously. In certain embodiments, the knockout of the UL19, UL30, UL48, UL54, RS1, RL2, and/or LAT gene occurs prior to knockdown of the UL19, UL30, UL48, UL54, RS1, RL2, and/or LAT gene. In certain embodiments, the knockout of the UL19, UL30, UL48, UL54, RS1, RL2, and/or LAT gene is concurrent with knockdown of the UL19, UL30, UL48, UL54, RS1, RL2, and/or LAT gene. In certain embodiments, the knockout of the UL19, UL30, UL48, UL54, RS1, RL2, and/or LAT gene is subsequent to the knockdown of the UL19, UL30, UL48, UL54, RS1, RL2, and/or LAT gene. In certain embodiments, the effect of the alterations is synergistic.

UL19 (also known as VP5) encodes the HSV-1 major capsid protein, VP5. Proper assembly of the viral capsid is known to be an essential part of viral replication, assembly, maturation and infection (Noma et al., Reviews of Medical Virology 1997; 7(2):107-122). RNAi-mediated knockdown of VP5 along with another capsid capsid protein, VP23, in vitro, greatly diminished HSV-1 proliferation (Jin et al., PLoS One 2014; 9(5): e96623). Knockout of UL19 can disable HSV-1 proliferation and therefore prevent, treat or cure HSV-1 infection.

UL30 encodes the DNA polymerase catalytic subunit (HSV-1 pol). The 5' domain of HSV-1 pol is required for viral replication. Knock out of UL30 can disable HSV-1 replication and therefore prevent and/or cure HSV-1 infection.

UL48 encodes the viral protein known as VP16 in HSV-1. VP-16 has been shown to be important in viral egress, the process by which the assembled viral capsid leaves the host nucleus and enters the cytoplasm (Mossman et al., Journal of Virology 2000; 74(14): 6287-6289). Mutation of UL48 in cell culture decreased the ability of HSV-1 to assemble efficiently (Svobodova et al., Journal of Virology 2012; 86(1): 473-483). Knockout of UL48 can disable HSV-1 assembly and egress and therefore prevent and/or cure HSV-1 infection.

UL54 encodes ICP27, a highly conserved, multi-functional protein. ICP27 is involved in transcription, RNA processing, RNA export and translation (Sandri-Goldin, Frontiers in Bioscience 2008; 13:5241-5256). ICP27 also shuts off host gene expression during HSV-1 infection. Knockout of UL54 can disable HSV-1 transcription, translation and RNA processing and therefore prevent and/or cure HSV-1 infection.

RS1 plays an important role in the expression of the immediate early genes by HSV-1 and HSV-2. RS1 is one of five immediate early genes expressed by herpes viruses and is a major transcriptional regulator. RS1 encodes the viral protein ICP4. ICP4 is important for controlling the overall expression of both early and late genes produced by HSV-1 and HSV-2. The RS1 gene is similar in HSV-1 and HSV-2.

RL2 encodes the gene ICP0, a 775 amino acid protein that is a transactivator of gene expression. The RL2 gene is one of five immediate early genes expressed by herpes viruses. ICP0 is involved in activating the expression of delayed early and late genes (Lees-Miller et al. 1996, Journal of Virology 70(11): 7471-7477). ICP0 is thought to be involved in neurovirulence. In cell culture, ICP0 has been found to be required for reactivation from latency (Leib et al. 1989, Journal of Virology 63:759-768). Deletion mutants not expressing RL2 have been shown to be unable to replicate in vitro (Sacks and Schaffer 1987, Journal of Virology 61(3):829-839). In certain embodiments, knock out of RL2 can disable the ability of HSV-1 and/or HSV-2 to reactivate from latency. In certain embodiments, knock out or knockdown of RL2 can disable the ability of HSV-1 and/or HSV-2 to replicate. In certain embodiments, knockout or knockdown of RL2 can disable the ability of HSV-1 and/or HSV-2 to infect and/or establish latent infections in neural tissue.

LAT encodes the only gene expressed by herpes viruses during the latency period. The latency period is the time in which the virus establishes a quiescent infection in host tissue, often in neural tissue, including the trigeminal ganglion or the sacral ganglia. LAT is thought to be involved in the reactivation of herpes virus infections, allowing the virus to re-infect epithelial and other tissue. In certain embodiments, knockout or knockdown of LAT can disable HSV-1 and/or HSV-2 gene latency and/or reactivation, disrupting the ability of HSV-1 and/or HSV-2 to sustain a latent infection and/or reactivate following latent infection. In certain embodiments, knockout or knockdown of LAT expression eliminates latent infection by HSV-1 and/or HSV-2. In certain embodiments, knockout or knockdown of LAT expression shortens the duration of, treats, and/or cures HSV-1 and/or HSV-2 infections.

4. Methods to Treat, Prevent and/or Reduce HSV-Related Ocular Infection

The presently disclosed subject matter provides methods for treating, preventing, and/or reducing HSV-related ocular infections by using the genome editing systems, genetic constructs, and compositions described herein. In certain embodiments, the method comprises administering to a tissue of a subject a presently disclosed genome editing system, genetic construct (e.g., a vector), or a composition. In certain embodiments, the method comprises administering to the one or both eyes of the subject a presently disclosed genome editing system, genetic construct (e.g., a vector), or a composition. In certain embodiments, the subject is suffering from HSV-related ocular infection, e.g., HSV-1 infection and/or HSV-2 infection. HSV-related ocular infection may be caused by an HSV-1 and/or HSV-2 infection. For example, and not by way of limitation, the methods, genome editing systems, genetic constructs, and compositions disclosed herein can be used to treat, prevent and/or reduce HSV-1 infection, HSV-2 infection, or both HSV-1 and HSV-2 infections. In certain embodiments, the method comprises knocking out or knocking down one or more.

HSV viral gene, e.g., UL19, UL30, UL48, UL54, RS1, and/or RL2 genes of HSV-1 and HSV-2. As the HSV-1 or HSV-2 virus establishes latency in discrete, localized regions within the body, it is highly amenable to local delivery that delivers a disabling treatment in the region of latency. Targeting knock-out to a discrete region or regions, (e.g., the trigeminal dorsal root ganglion, the cornea, the cervical dorsal root ganglia, or the sacral dorsal root ganglia) can reduce or eliminate latent infection by disabling the HSV-1 and/or HSV-2 virus.

In certain embodiments, knockout or knockdown of the UL19, UL30, UL48, UL54, RS1, and/or RL2 gene disables HSV-1 and/or HSV-2 gene expression, or reduces one or more of viral replication, assembly, maturation, packaging, or infection. In certain embodiments, knockout of UL19, UL30, UL48, UL54, RS1, and/or RL2 gene expression shortens the duration of HSV-1 and/or HSV-2 infections. In certain embodiments, knockout or knockdown of UL19, UL30, UL48, UL54, RS1, and/or RL2 gene expression treats or cures HSV-1 and/or HSV-2 infections.

In certain embodiments, reducing the duration, number and/or frequency of ocular related HSV-reactivations can decrease the risk of permanent visual damage in subjects infected with HSV-1 and/or HSV-2.

In certain embodiments, knocking out and/or knocking down UL19, UL30, UL48, UL54, RS1, and/or RL2 gene, individually or in combination can make HSV-1 and/or HSV-2 more susceptible to antiviral therapy. Mutations in important genes can render HSV-1, HSV-2 and other viruses more susceptible to treatment with antivirals (Zhou et al., Journal of Virology 2014; 88(19): 11121-11129). Knockout or knockdown of the UL19, UL30, UL48, UL54, RS1, and/or RL2 genes, individually or in combination may be combined with an antiviral therapy to prevent, treat and/or reduce HSV-1 and/or HSV-2 infection. The genome editing systems, genetic constructs, compositions, and methods described herein can be used in combination with another antiviral therapy, e.g., another anti-HSV-1 therapy or anti-HSV-2 therapy described herein, to prevent, treat and/or reduce HSV-1 or HSV-2 infection.

In certain embodiments, the method comprises knocking out one, two, three, four, five, six or seven HSV-1 and/or HSV-2 gene (e.g., UL19, UL30, UL48, UL54, RS1, or RL2 gene). In certain embodiments, the method comprises knocking down one, two, three, four, five, six or seven HSV-1 and/or HSV-2 gene (e.g., UL19, UL30, UL48, UL54, RS1, or RL2 gene).

In certain embodiments, inhibiting one or more viral functions, e.g., viral gene regulation, viral gene transcription, viral genome replication and viral capsid formation, decreases the duration of primary or recurrent infection and/or decreases shedding of viral particles. Subjects may also experience shorter duration(s) of illness, decreased risk of transmission to sexual partners, decreased risk of transmission to the fetus in the case of pregnancy and/or the potential for full clearance of HSV-1 and/or HSV-2 (cure).

Knockout or knockdown of one or more copies (e.g., 1, 2, 3, 4, 5, 6, 7, 8, 9, 10, 20, 30, 40 50, 100, 200, 300, 400, 500, 600, 700, 800, 900, 1000 or more copies) of one or more target gene(s) (e.g., the UL19, UL30, UL48, UL54, RS1, RL2, and/or LAT gene) may be performed prior to disease onset or after disease onset, preferably early in the disease course.

In certain embodiments, the method comprises initiating treatment of a subject prior to disease onset. In certain embodiments, the method comprises initiating treatment of a subject after disease onset.

In certain embodiments, the method comprises initiating treatment of a subject after disease onset, e.g., 1, 2, 3, 4, 5, 6, 7, 8, 9, 10, 12, 16, 24, 36, 48 or more months after onset of an HSV-1 and/or HSV-2 infection. In certain embodiments, the method comprises initiating treatment of a subject after disease onset, e.g., 1, 2, 3, 4, 5, 10, 15, 20, 25, 40, 50 or 60 years after onset of an HSV-1 and/or HSV-2 infection.

In certain embodiments, the method comprises initiating treatment of a subject in an advanced stage of disease, e.g., during acute or latent periods. In certain embodiments, the method comprises initiating treatment of a subject in severe, acute stages of the disease affecting the central nervous system, eyes, oropharynx, genital region, and/or other regions.

Overall, initiation of treatment for subjects at all stages of disease is expected to improve healing, decrease duration of disease and be of benefit to subjects.

In certain embodiments, the method comprises initiating treatment of a subject prior to disease progression. In certain embodiments, the method comprises initiating treatment of a subject in an early stage of disease, e.g., when a subject has been exposed to HSV-1 and/or HSV-2 or is thought to have been exposed to HSV-1 and/or HSV-2.

In certain embodiments, the method comprises initiating treatment of a subject prior to disease progression. In certain embodiments, the method comprises initiating treatment of a subject in an early stage of disease, e.g., when a subject has tested positive for HSV-1 and/or HSV-2 infections but has no signs or symptoms.

In certain embodiments, the method comprises initiating treatment at the appearance of one or more of the following findings consistent or associated with an HSV-1 and/or HSV-2 infection: fever, headache, body aches, ano-genital blistering, oral ulceration, encephalitis, or keratitis.

In certain embodiments, the method comprises initiating treatment of a subject at the appearance of painful blistering in or around the mouth, e.g., oral or oropharynx, e.g., in an infant, child, adult or young adult.

In certain embodiments, the method comprises initiating treatment of a subject at the appearance of painful blistering in the ano-genital region, geneital ulcers, and/or a flu-like symptom, e.g., in an infant, child, adult or young adult.

In certain embodiments, the method comprises initiating treatment of a subject suspected of having HSV-1 and/or HSV-2 meningitis and/or HSV-1 and/or HSV-2 encephalitis.

In certain embodiments, the method comprises initiating treatment at the appearance of one or more of the following symptoms consistent or associated with HSV-1 and/or HSV-2 meningitis and/or encephalitis: fever, headache, vomiting, photophobia, seizure, decline in level of consciousness, lethargy, or drowsiness.

In certain embodiments, the method comprises initiating treatment at the appearance of any of the following signs consistent or associated with HSV-1 and/or HSV meningitis and/or encephalitis: positive CSF culture for HSV-1 and/or HSV-2, elevated WBC in CSF, neck stiffness/positive Brudzinski's sign. In certain embodiments, the method comprises initiating treatment in a patient with signs consistent with HSV-1 and/or HSV-2 encephalitis and/or meningitis on EEG, CSF exam, MRI, PCR of CSF specimen, and/or PCR of brain biopsy specimen.

In certain embodiments, the method comprises initiating treatment at the appearance of any of the following symptoms consistent or associated with optic HSV-1 and/or HSV-2: pain, photophobia, blurred vision, tearing, redness/injection, loss of vision, floaters, or flashes.

In certain embodiments, the method comprises initiating treatment at the appearance of any of the following findings on ophthalmologic exam consistent or associated with optic HSV-1 and/or HSV-2, also known as HSV-1 and/or HSV-2 keratitis: small, raised clear vesicles on corneal epithelium; irregular corneal surface, punctate epithelial erosions; dense stromal infiltrate; ulceration; necrosis; focal, multifocal, or diffuse cellular infiltrates; immune rings; neovascularization; or ghost vessels at any level of the cornea.

In certain embodiments, the method comprises initiating treatment at the appearance of any of the following findings on ophthalmologic exam consistent or associated with HSV-1 and/or HSV-2 retinitis or acute retinal necrosis: reduced visual acuity; uveitis; vitritis; scleral injection; inflammation of the anterior and/or vitreous chamber/s; vitreous haze; optic nerve edema; peripheral retinal whitening; retinal tear; retinal detachment; retinal necrosis; evidence of occlusive vasculopathy with arterial involvement, including arterioloar sheathing and arteriolar attenuation.

In certain embodiments, the method comprises initiating treatment at the appearance of symptoms and/or signs consistent or associated with either an HSV-1 or an HSV-2 infection of the eye, oropharynx, ano-genital region or central nervous system. In certain embodiments, intiating treatment for an HSV-1 and/or HSV-2 infection in a case of suspected HSV-1 or HSV-2 infection early in the disease course is beneficial.

In certain embodiments, the method comprises initiating treatment in utero. In certain embodiments, the subject is at high risk of maternal-to-fetal transmission.

In certain embodiments, the method comprises initiating treatment during pregnancy in case of mother who has an active HSV-1 and/or HSV-2 infection or has recent primary HSV-1 and/or HSV-2 infection.

In certain embodiments, the method comprises initiating treatment prior to organ transplantation or immediately following organ transplantation.

In certain embodiments, the method comprises initiating treatment in case of suspected exposure to HSV-1 and/or HSV-2.

In certain embodiments, the method comprises initiating treatment prophylactically, in case of suspected HSV-encephalitis or meningitis.

In certain embodiments, both HIV positive subjects and post-transplant subjects may experience severe HSV-1 and/or HSV-2 activation or reactivation, including HSV-encephalitis and meningitis, due to immunodeficiency. Neonates are also at risk for severe HSV-encephalitis due to maternal-fetal transmission during childbirth. Inhibiting one or more viral functions, e.g., viral gene regulation, viral gene transcription, viral genome replication, and viral capsid formation, may provide superior protection to said populations at risk for severe HSV-1 and/or HSV-2 infections. Subjects may experience lower rates of HSV-1 and/or HSV-2 encephalitis and/or lower rates of severe neurologic sequelae following HSV-1 and/or HSV-2 encephalitis, which will profoundly improve quality of life.

In certain embodiments, the method comprises initiating treatment of a subject who suffers from or is at risk of developing severe manifestations of HSV-1 and/or HSV-2 infections, e.g., a neonates, a subjects with HIV, a subject who is undergoing an immunosuppressant therapy, e.g., following organ transplantation, a subject who hascancer, a subject who is undergoing chemotherapy, a subject who is undergoing chemotherapy, a subject who is undergoing radiation therapy, a subject who will undergo radiation therapy.

In certain embodiments, both HIV positive subjects and post-transplant subjects may experience severe HSV-1 and/or HSV-2 activation or reactivation, including HSV-encephalitis and meningitis, due to immunodeficiency. Neonates are also at risk for severe HSV-encephalitis due to maternal-fetal transmission during childbirth. Inhibiting essential viral functions, e.g., viral gene regulation, viral gene transcription, expression of viral latency genes, viral genome replication and viral capsid formation, may provide superior protection to said populations at risk for severe HSV-1 and/or HSV-2 infections. Subjects may experience lower rates of HSV-1 and/or HSV-2 encephalitis and/or lower rates of severe neurologic sequelae following HSV-1 and/or HSV-2 encephalitis, which will profoundly improve quality of life.

In certain embodiments, the method comprises initiating treatment of a subject who has tested positive for HSV-1 and/or HSV-2.

In certain embodiments, the method comprises initiating treatment in a subject who has tested positive for HSV-1 and/or HSV-2 infection. HSV-1 and/or HSV-2 infections can be tested, e.g., using viral culture, direct fluorescent antibody study, skin biopsy, PCR, blood serologic test, CSF serologic test, CSF PCR, or brain biopsy. In certain embodiments, the method comprises initiating treatment in a subject who has tested positive for HSV-2 infection via diagnostic vitrectomy, endoretinal biopsy, or PCR of aqueous fluid, PCR of vitreous sample.

In certain embodiments, the method comprises initiating treatment in a subject exposed to HSV-1 and/or HSV-2 and at high risk for severe sequelae from HSV infection.

In certain embodiments, a cell is manipulated by editing (e.g., introducing a mutation in) one or more target genes, e.g., the UL19, UL30, UL48, UL54, RS1, and/or RL2 gene. In certain embodiments, the expression of one or more target genes (e.g., one or more of UL19, UL30, UL48, UL54, RS1, and RL2 gene described herein) is modulated, e.g., in vivo.

In certain embodiments, the method comprises delivery of gRNA molecule by an adeno-associated virus (AAV). In certain embodiments, the method comprises delivery of gRNA molecule by a lentivirus (LV). In certain embodiments, the method comprises delivery of gRNA molecule by a nanoparticle.

In certain embodiments, the method further comprising administering to the subject a second antiviral therapy or therapeutic agent, e.g., an anti-HSV-1 or anti-HSV-2 therapy or therapeutic agent described herein. The composition and the other therapy or therapeutic agent can be administered in any order. For example, the compositions described herein can be administered concurrently with, prior to, or subsequent to, one or more additional therapies or therapeutic agents. In certain embodiments, the effect of the two or more therapies or therapeutic agents is synergistic. Exemplary anti-HSV-1 and anti-HSV-2 therapies and therapeutic agents include, but are not limited to, acyclovir, valacyclovir, famciclovir, penciclovir, or a vaccine.

5. Methods of Altering HSV Viral Gene(s)

As disclosed herein, the HSV viral gene(s) (e.g., UL19, UL30, UL48, UL54, RS1, and/or RL2 gene) can be altered by the genome editing systems, genetic constructs, compositions or methods disclosed herein.

Alteration of the HSV viral genes can be achieved, e.g., by:
(1) knocking out the HSV viral gene (UL19, UL30, UL48, UL54, RS1, RL2, and/or LAT gene) by:
  (a) insertion or deletion (e.g., NHEJ-mediated insertion or deletion) of one or more nucleotides in close proximity to or within the early coding region of the UL19, UL30, UL48, UL54, RS1, and/or RL2 gene; or
  (b) deletion (e.g., NHEJ-mediated deletion) of a genomic sequence or multiple genomic sequences including at least a portion of the UL19, UL30, UL48, UL54, RS1, RL2, and/or LAT gene gene; or
(2) knocking down the UL19, UL30, UL48, UL54, RS1, RL2, and/or LAT gene mediated by an eiCas9 molecule or an eiCas9-fusion protein by targeting a non-coding region, e.g., a promoter region, of the UL19, UL30, UL48, UL54, RS1, RL2, and/or LAT gene gene.

All approaches give rise to alteration (e.g., knockout or knockdown) of the HSV viral gene(s) (e.g., the UL19, UL30, UL48, UL54, RS1, RL2, and/or LAT gene(s)). Exemplary mechanisms that can be associated with an alteration of the HSV viral genes include, but are not limited to, non-homologous end joining (e.g., classical or alternative), microhomology-mediated end joining (MMEJ), homology-directed repair (e.g., endogenous donor template mediated), SDSA (synthesis dependent strand annealing), single strand annealing or single strand invasion.

In certain embodiments, the methods, genome editing systems, genetic constructs, and composition described herein introduce one or more breaks near the early coding region of the HSV viral gene(s). In certain embodiments, methods, genetic constructs, genome editing systems, and compositions described herein introduce two or more breaks to flank at least a portion of the HSV viral gene(s). The two or more breaks remove (e.g., delete) a genomic sequence including at least a portion of the HSV viral gene(s). In certain embodiments, the methods described herein comprise knocking down the HSV viral gene(s) mediated by eiCas9 molecule or an eiCas9-fusion protein by targeting the promoter region of the UL19, UL30, UL48, UL54, RS1, RL2, and/or LAT genes.

5.1 Knocking Out the HSV Viral Gene by Introducing an Indel or a Deletion in the Gene In certain embodiments, the method comprises introducing an insertion or deletion of one or more nucleotides in close proximity to the early coding region of the HSV viral gene(s). In certain embodiments, the method comprises the introduction of one or more breaks (e.g., single strand breaks or double strand breaks) sufficiently close to (e.g., either 5' or 3' to) the early coding region of the HSV viral gene, such that the break-induced indel could be reasonably expected to span a target position of the HSV viral gene. NHEJ-mediated repair of the break(s) allows for the NHEJ-mediated introduction of an indel in close proximity to or within the early coding region of the HSV viral gene.

In certain embodiments, the method comprises introducing a deletion of a genomic sequence comprising at least a portion of the HSV viral gene. In certain embodiments, the method comprises introducing two double stand breaks—one 5' and the other 3' to (i.e., flanking) a target position at the HSV viral gene. In certain embodiments, two gRNAs, e.g., unimolecular (or chimeric) or modular gRNA molecules, are configured to position two double strand breaks on opposite sides of a target position in the HSV viral gene.

In certain embodiments, a single strand break is introduced (e.g., positioned by one gRNA molecule) at or in close proximity to a target position in the HSV viral gene. In certain embodiments, a single gRNA molecule (e.g., with a Cas9 nickase) is used to create a single strand break at or in close proximity to a target position in the HSV viral gene, e.g., the gRNA molecule is configured such that the single strand break is positioned either upstream (e.g., within 200 bp upstream) or downstream (e.g., within 200 bp downstream) of a target position in the HSV viral gene. In certain embodiments, the break is positioned to avoid unwanted target chromosome elements, such as repeat elements, e.g., an Alu repeat. In certain embodiments, a double strand break is introduced (e.g., positioned by one gRNA molecule) at or in close proximity to a target position in the HSV viral gene. In certain embodiments, a single gRNA molecule (e.g., with a Cas9 nuclease other than a Cas9 nickase) is used to create a double strand break at or in close proximity to a target position in the HSV viral gene, e.g., the gRNA molecule is configured such that the double strand break is positioned either upstream (e.g., within 200 bp upstream) or downstream of (e.g., within 200 bp downstream) of a target position in the HSV viral gene. In certain embodiments, the break is positioned to avoid unwanted target chromosome elements, such as repeat elements, e.g., an Alu repeat.

In certain embodiments, two single strand breaks are introduced (e.g., positioned by two gRNA molecules) at or in close proximity to a target position in the HSV viral gene. In certain embodiments, two gRNA molecules (e.g., with one or two Cas9 nickases) are used to create two single strand breaks at or in close proximity to a target position in the HSV viral gene, e.g., the gRNAs molecules are configured such that both of the single strand breaks are positioned upstream (e.g., within 200 bp upstream) or downstream (e.g., within 200 bp downstream) of a target position in the HSV viral gene. In certain embodiments, two gRNA molecules (e.g., with two Cas9 nickases) are used to create two single strand breaks at or in close proximity to a target position in the HSV viral gene, e.g., the gRNAs molecules are configured such that one single strand break is positioned upstream (e.g., within 200 bp upstream) and a second single strand break is positioned downstream (e.g., within 200 bp downstream) of a target position in the HSV viral gene. In certain embodiments, the breaks are positioned to avoid unwanted target chromosome elements, such as repeat elements, e.g., an Alu repeat.

In certain embodiments, two double strand breaks are introduced (e.g., positioned by two gRNA molecules) at or in close proximity to a target position in the HSV viral gene. In certain embodiments, two gRNA molecules (e.g., with one or two Cas9 nucleases that are not Cas9 nickases) are used to create two double strand breaks to flank a target position in the HSV viral gene, e.g., the gRNA molecules are configured such that one double strand break is positioned upstream (e.g., within 200 bp upstream) and a second double strand break is positioned downstream (e.g., within 200 bp downstream) of a target position in the HSV viral gene. In certain embodiments, the breaks are positioned to avoid unwanted target chromosome elements, such as repeat elements, e.g., an Alu repeat.

In certain embodiments, one double strand break and two single strand breaks are introduced (e.g., positioned by three gRNA molecules) at or in close proximity to a target position in the HSV viral gene. In certain embodiments, three gRNA molecules (e.g., with a Cas9 nuclease other than a Cas9 nickase and one or two Cas9 nickases) to create one double strand break and two single strand breaks to flank a target position in the HSV viral gene, e.g., the gRNA molecules are configured such that the double strand break is positioned upstream or downstream of (e.g., within 200 bp upstream or downstream) of a target position in the HSV viral gene, and the two single strand breaks are positioned at the opposite site, e.g., downstream or upstream (within 200 bp downstream or upstream), of a target position in the HSV viral gene. In certain embodiments, the breaks are positioned to avoid unwanted target chromosome elements, such as repeat elements, e.g., an Alu repeat.

In certain embodiments, four single strand breaks are introduced (e.g., positioned by four gRNA molecules) at or in close proximity to a target position in the HSV viral gene. In certain embodiments, four gRNA molecule (e.g., with one or more Cas9 nickases are used to create four single strand breaks to flank a target position in the HSV viral gene, e.g., the gRNA molecules are configured such that a first and second single strand breaks are positioned upstream (e.g., within 200 bp upstream) of a target position in the HSV viral gene, and a third and a fourth single stranded breaks are positioned downstream (e.g., within 200 bp downstream) of a target position in the HSV viral gene. In certain embodiments, the breaks are positioned to avoid unwanted target chromosome elements, such as repeat elements, e.g., an Alu repeat.

In certain embodiments, two or more (e.g., three or four) gRNA molecules are used with one Cas9 molecule or Cas9-fusion protein. In certain embodiments, when two or more (e.g., three or four) gRNAs are used with two or more Cas9 molecules, at least one Cas9 molecule is from a different species than the other Cas9 molecule(s). For example, when two gRNA molecules are used with two Cas9 molecules, one Cas9 molecule can be from one species and the other Cas9 molecule can be from a different species. Both Cas9 species are used to generate a single or double-strand break, as desired.

5.2. Knocking Out the One or More of the HSV Viral Gene(S) by Deleting (e.g., NHEJ-Mediated Deletion) a Genomic Sequence or Multiple Genomic Sequences Comprising at Least a Portion of the Gene(S)

In certain embodiments, the method comprises deleting (e.g., NHEJ-mediated deletion) a genomic sequence including at least a portion of the HSV viral gene(s) or multiple genomic sequences including at least a portion of the HSV viral gene(s). In certain embodiments, the method comprises introducing two double stand breaks—one 5' and the other 3' to (i.e., flanking) a target position in the HSV viral gene. In certain embodiments, two gRNAs, e.g., unimolecular (or chimeric) or modular gRNA molecules, are configured to position the two double strand breaks on opposite sides of a target position in the HSV viral gene. In certain embodiments, two gRNAs, e.g., unimolecular (or chimeric) or modular gRNA molecules, are configured to position the two double strand breaks on opposite sides of a target position in the HSV viral gene. In certain embodiments, two gRNAs, e.g., unimolecular (or chimeric) or modular gRNA molecules, are configured to position the two double strand breaks on opposite sides of a target position in the HSV viral gene.

5.3 Genome Editing Approaches

In certain embodiments, the alteration of the HSV viral gene is mediated by Homology-directed repair (HDR). In certain embodiments, "Homology-directed repair" or "HDR" refers to a mechanism in cells to repair double strand DNA lesions when a homologous piece of DNA is present in the nucleus, mostly in G2 and S phase of the cell cycle.

In certain embodiments, the HDR-mediated sequence alteration uses an exogenously provided template nucleic acid (also referred to herein as a donor template). If a donor template is provided along with the genome editing system (CRISPR/Cas9-based systems), then the cellular machinery will repair the break by homologous recombination, which is enhanced several orders of magnitude in the presence of DNA cleavage. When the homologous DNA piece is absent, nonhomologous end joining may take place instead. In certain embodiments, a plasmid donor is used as a template for homologous recombination. In certain embodiments, a single stranded donor template is used as a template for the targeted alteration.

In certain embodiments, the donor template is double stranded. In certain embodiments, the donor template is single stranded. In certain embodiments, the donor template comprises a single stranded portion and a double stranded portion.

In certain embodiments, the alteration of the HSV viral gene is mediated by nuclease-induced non-homologous end-joining (NHEJ). In certain embodiments, "Non-homologous end joining (NHEJ) pathway" or "NHEJ" refers to a pathway that repairs double-strand breaks in DNA by directly ligating the break ends without the need for a homologous template. As described herein, nuclease-induced non-homologous end-joining (NHEJ) can be used to target gene-specific knockouts. Nuclease-induced NHEJ can also be used to remove (e.g., delete) sequence insertions in a gene of interest.

In certain embodiments, the genomic alterations associated with the methods described herein rely on nuclease-induced NHEJ and the error-prone nature of the NHEJ repair pathway. NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations typically alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein.

The indel mutations generated by NHEJ are unpredictable in nature; however, at a given break site certain indel sequences are favored and are over represented in the population, likely due to small regions of microhomology. The lengths of deletions can vary widely; they are most commonly in the 1-50 bp range, but can reach greater than 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it can also be used to delete small sequence motifs (e.g., motifs less than or equal to 50 nucleotides in length) as long as the generation of a specific final sequence is not required. If a double-strand break is targeted near to a target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. In this way, DNA segments as large as several hundred kilobases can be deleted. Both of these approaches can be used to delete specific DNA sequences; however, the error-prone nature of NHEJ may still produce indel mutations at the site of repair.

Both double strand cleaving eaCas9 molecules and single strand, or nickase, eaCas9 molecules can be used in the methods and compositions described herein to generate NHEJ-mediated indels. NHEJ-mediated indels targeted to the early coding region of the HSV viral gene can be used to knockout (i.e., eliminate expression) of the HSV viral gene. For example, early coding region of a HSV viral gene includes sequence immediately following a transcription start site, within a first exon of the coding sequence, or within 500 bp of the transcription start site (e.g., less than 500, 450, 400, 350, 300, 250, 200, 150, 100 or 50 bp).

6. Guide RNA (gRNA) Molecules

The presently disclosed subject matter provides gRNA molecules targeting a HSV viral gene (e.g., a (HSV-1 or HSV-2) UL19 gene, a (HSV-1 or HSV-2) UL30 gene, a (HSV-1 or HSV-2) UL48 gene, a (HSV-1 or HSV-2) UL54 gene, a (HSV-1 or HSV-2) RS1 gene, a (HSV-1 or HSV-2) RL2 gene), or a (HSV-1 or HSV-2) LAT gene). In certain embodiments, the gRNA molecule targets a HSV-1 UL19 gene, a HSV-1 UL30 gene, a HSV-1UL48 gene, a HSV- 1UL54 gene, a HSV-1 RS1 gene, a HSV-1 RL2 gene, or a HSV-1 LAT gene. gRNA can target a coding region or a non-coding region of a HSV viral gene. Non-limiting examples of non-coding regions include a promoter region, an enhancer region, an intron, the 3' UTR, the 5' UTR, or a polyadenylation signal region of the HSV viral gene. In certain embodiments, the coding region comprises an early coding region of the HSV viral gene.

6.1 Structures of gRNA Molecules

A gRNA molecule, as used herein, refers to a nucleic acid that promotes the specific targeting or homing of a gRNA molecule/Cas9 molecule complex to a target nucleic acid. gRNA molecules can be unimolecular (having a single RNA molecule) (e.g., chimeric), or modular (comprising more than one, and typically two, separate RNA molecules). In certain embodiments, a gRNA molecule comprises a targeting domain comprising, consisting of, or consisting essentially of a nucleic acid sequence fully or partially complementary to a target domain (also referred to as "target sequence") in a target gene, e.g., a HSV viral gene). In certain embodiments, the gRNA molecule further comprises one or more additional domains, including for example a first complementarity domain, a linking domain, a second complementarity domain, a proximal domain, a tail domain, and a 5' extension domain. In certain embodiments, one or more of the domains in the gRNA molecule comprises a nucleotide sequence identical to or sharing sequence homology with a naturally occurring sequence, e.g., from *S. pyogenes*, or *S. aureus*.

In certain embodiments, the targeting domain comprises a core domain and an optional secondary domain. In certain embodiments, the core domain is located 3' to the secondary domain, and in certain of these embodiments the core domain is located at or near the 3' end of the targeting domain. In certain embodiments, the core domain consists of or consists essentially of about 8 to about 13 nucleotides at the 3' end of the targeting domain. In certain embodiments, only the core domain is complementary or partially complementary to the corresponding portion of the target sequence, and in certain of these embodiments the core domain is fully complementary to the corresponding portion of the target sequence. In certain embodiments, the secondary domain is also complementary or partially complementary to a portion of the target sequence. In certain embodiments, the core domain is complementary or partially complementary to a core domain target in the target sequence, while the secondary domain is complementary or partially complementary to a secondary domain target in the target sequence. In certain embodiments, the core domain and secondary domain have the same degree of complementarity with their respective corresponding portions of the target sequence. In certain embodiments, the degree of complementarity between the core domain and its target and the degree of complementarity between the secondary domain and its target may differ. In certain embodiments, the core domain may have a higher degree of complementarity for its target than the secondary domain, whereas in other embodiments the secondary domain may have a higher degree of complementarity than the core domain.

In certain embodiments, the targeting domain and/or the core domain within the targeting domain is 3 to 100, 5 to 100, 10 to 100, or 20 to 100 nucleotides in length, and in certain of these embodiments the targeting domain or core domain is 3 to 15, 3 to 20, 5 to 20, 10 to 20, 15 to 20, 5 to 50, 10 to 50, or 20 to 50 nucleotides in length. In certain embodiments, the targeting domain and/or the core domain within the targeting domain is 6, 7, 8, 9, 10, 11, 12, 13, 14, 15, 16, 17, 18, 19, 20, 21, 22, 23, 24, 25, or 26 nucleotides in length. In certain embodiments, the targeting domain and/or the core domain within the targeting domain is 6+/−2, 7+/−2, 8+/−2, 9+/−2, 10+/−2, 10+/−4, 10+/−5, 11+/−2, 12+/−2, 13+/−2, 14+/−2, 15+/−2, or 16+/−2, 20+/−5, 30+/−5, 40+/−5, 50+/−5, 60+/−5, 70+/−5, 80+/−5, 90+/−5, or 100+/−5 nucleotides in length.

In certain embodiments, the targeting domain includes a core domain that is 3 to 20 nucleotides in length, e.g., 5 to 15, or 8 to 13 nucleotides in length. In certain embodiments, the targeting domain includes a secondary domain that is 0, 1, 2, 3, 4, 5, 6, 7, 8, 9, 10, 11, 12, 13, 14 or 15 nucleotides in length. In certain embodiments, the targeting domain comprises a core domain that is 8 to 13 nucleotides in length, the targeting domain is 26, 25, 24, 23, 22, 21, 20, 19, 18, 17, or 16 nucleotides in length, and the secondary domain is 13 to 18, 12 to 17, 11 to 16, 10 to 15, 9 to 14, 8 to 13, 7 to 12, 6 to 11, 5 to 10, 4 to 9, or 3 to 8 nucleotides in length, respectively.

gRNA molecule can comprise a "G" at the 5' end of the targeting domain. The targeting domain of a gRNA molecule can be at least a 10 base pair, at least a 11 base pair, at least a 12 base pair, at least a 13 base pair, at least a 14 base pair, at least a 15 base pair, at least a 16 base pair, at least a 17 base pair, at least a 18 base pair, at least a 19 base pair, at least a 20 base pair, at least a 21 base pair, at least a 22 base pair, at least a 23 base pair, at least a 24 base pair, at least a 25 base pair, at least a 30 base pair, or at least a 35 base pair. In certain embodiments, the targeting domain of a gRNA molecule has 19-24 nucleotides in length. In certain embodiments, the targeting domain of a gRNA molecule is 20 nucleotides in length. In certain embodiments, the targeting domain of a gRNA molecule is 21 nucleotides in length. In certain embodiments, the targeting domain of a gRNA molecule is 22 nucleotides in length. In certain embodiments, the targeting domain of a gRNA molecule is 23 nucleotides in length. In certain embodiments, the targeting domain of a gRNA molecule is 24 nucleotides in length.

The first and second complementarity (sometimes referred to alternatively as the crRNA-derived hairpin sequence and tracrRNA-derived hairpin sequences, respectively) domains are fully or partially complementary to one another. In certain embodiments, the degree of complementarity is sufficient for the two domains to form a duplexed region under at least some physiological conditions. In certain embodiments, the degree of complementarity between the first and second complementarity domains, together with other properties of the gRNA, is sufficient to allow targeting of a Cas9 molecule to a target nucleic acid.

In certain embodiments, the first complementarity domain is 5 to 30, 5 to 25, 7 to 25, 5 to 24, 5 to 23, 7 to 22, 5 to 22, 5 to 21, 5 to 20, 7 to 18, 7 to 15, 9 to 16, or 10 to 14 nucleotides in length. In certain of these embodiments, the first complementarity domain is 5, 6, 7, 8, 9, 10, 11, 12, 13, 14, 15, 16, 17, 18, 19, 20, 21, 22, 23, 24, or 25 nucleotides in length. In certain embodiments, the second complementarity domain is 5 to 27, 7 to 27, 7 to 25, 5 to 24, 5 to 23, 5 to 22, 5 to 21, 7 to 20, 5 to 20, 7 to 18, 7 to 17, 9 to 16, or 10 to 14 nucleotides in length. In certain embodiments, the second complementarity domain is 5, 6, 7, 8, 9, 10, 11, 12, 13, 14, 15, 16, 17, 18, 19, 20, 21, 22, 23, 24, 25, or 26 nucleotides in length. In certain embodiments, the first and second complementarity domains are each independently 6+/−2, 7+/−2, 8+/−2, 9+/−2, 10+/−2, 11+/−2, 12+/−2, 13+/−

2, 14+/−2, 15+/−2, 16+/−2, 17+/−2, 18+/−2, 19+/−2, or 20+/−2, 21+/−2, 22+/−2, 23+/−2, or 24+/−2 nucleotides in length. In certain embodiments, the second complementarity domain is longer than the first complementarity domain, e.g., 2, 3, 4, 5, or 6 nucleotides longer. In certain embodiments, the duplexed region formed by the first and second complementarity domains is, for example, 6, 7, 8, 9, 10, 11, 12, 13, 14, 15, 16, 17, 18, 19, 20, 21, or 22 bp in length, excluding any looped out or unpaired nucleotides.

The linking domain is disposed between and serves to link the first and second complementarity domains in a unimolecular or chimeric gRNA. In certain embodiments, part of the linking domain is from a crRNA-derived region, and another part is from a tracrRNA-derived region. In certain embodiments, the linking domain links the first and second complementarity domains covalently. In certain embodiments, the linking domain comprises a covalent bond. In certain embodiments, the linking domain links the first and second complementarity domains non-covalently. In certain embodiments, the linking domain is ten or fewer nucleotides in length, e.g., 1, 2, 3, 4, 5, 6, 7, 8, 9, or 10 nucleotides. In certain embodiments, the linking domain is greater than 10 nucleotides in length, e.g., 11, 12, 13, 14, 15, 16, 17, 18, 19, 20, 21, 22, 23, 24, or 25 or more nucleotides. In certain embodiments, the linking domain is 2 to 50, 2 to 40, 2 to 30, 2 to 20, 2 to 10, 2 to 5, 10 to 100, 10 to 90, 10 to 80, 10 to 70, 10 to 60, 10 to 50, 10 to 40, 10 to 30, 10 to 20, 10 to 15, 20 to 100, 20 to 90, 20 to 80, 20 to 70, 20 to 60, 20 to 50, 20 to 40, 20 to 30, or 20 to 25 nucleotides in length. In certain embodiments, the linking domain is 10+/−5, 20+/−5, 20+/−10, 30+/−5, 30+/−10, 40+/−5, 40+/−10, 50+/−5, 50+/−10, 60+/−5, 60+/−10, 70+/−5, 70+/−10, 80+/−5, 80+/−10, 90+/−5, 90+/−10, 100+/−5, or 100+/−10 nucleotides in length.

In certain embodiments, a modular gRNA as disclosed herein comprises a 5' extension domain, i.e., one or more additional nucleotides 5' to the second complementarity domain. In certain embodiments, the 5' extension domain is 2 to 10 or more, 2 to 9, 2 to 8, 2 to 7, 2 to 6, 2 to 5, or 2 to 4 nucleotides in length. In certain embodiments, the 5' extension domain is 2, 3, 4, 5, 6, 7, 8, 9, or 10 or more nucleotides in length.

In certain embodiments, the proximal domain is 5 to 20 or more nucleotides in length, e.g., 5, 6, 7, 8, 9, 10, 11, 12, 13, 14, 15, 16, 17, 18, 19, 20, 21, 22, 23, 24, 25, or 26 nucleotides in length. In certain embodiments, the proximal domain is 6+/−2, 7+/−2, 8+/−2, 9+/−2, 10+/−2, 11+/−2, 12+/−2, 13+/−2, 14+/−2, 14+/−2, 16+/−2, 17+/−2, 18+/−2, 19+/−2, or 20+/−2 nucleotides in length. In certain embodiments, the proximal domain is 5 to 20, 7, to 18, 9 to 16, or 10 to 14 nucleotides in length.

In certain embodiments, the tail domain is absent. In certain embodiments, the tail domain is 1 to 100 or more nucleotides in length, e.g., 1, 2, 3, 4, 5, 6, 7, 8, 9, 10, 20, 30, 40, 50, 60, 70, 80, 90, or 100 nucleotides in length. In certain embodiments, the tail domain is 1 to 5, 1 to 10, 1 to 15, 1 to 20, 1 to 50, 10 to 100, 20 to 100, 10 to 90, 20 to 90, 10 to 80, 20 to 80, 10 to 70, 20 to 70, 10 to 60, 20 to 60, 10 to 50, 20 to 50, 10 to 40, 20 to 40, 10 to 30, 20 to 30, 20 to 25, 10 to 20, or 10 to 15 nucleotides in length. In certain embodiments, the tail domain is 5+/−5, 10+/−5, 20+/−10, 20+/−5, 25+/−10, 30+/−10, 30+/−5, 40+/−10, 40+/−5, 50+/−10, 50+/−5, 60+/−10, 60+/−5, 70+/−10, 70+/−5, 80+/−10, 80+/−5, 90+/−10, 90+/−5, 100+/−10, or 100+/−5 nucleotides in length, In certain embodiments, the tail domain includes sequences that are complementary to each other and which, under at least some physiological conditions, form a duplexed region. In certain of these embodiments, the tail domain comprises a tail duplex domain which can form a tail duplexed region. In certain embodiments, the tail duplexed region is 3, 4, 5, 6, 7, 8, 9, 10, 11, or 12 bp in length. In certain embodiments, the tail domain comprises a single stranded domain 3' to the tail duplex domain that does not form a duplex. In certain of these embodiments, the single stranded domain is 3 to 10 nucleotides in length, e.g., 3, 4, 5, 6, 7, 8, 9, 10, or 4 to 6 nucleotides in length.

In certain embodiments, the tail domain includes nucleotides at the 3' end that are related to the method of in vitro or in vivo transcription. When a T7 promoter is used for in vitro transcription of the gRNA, these nucleotides may be any nucleotides present before the 3' end of the DNA template. In certain embodiments, the gRNA molecule includes a 3' polyA tail that is prepared by in vitro transcription from a DNA template. In certain embodiments, the 5' nucleotide of the targeting domain of the gRNA molecule is a guanine nucleotide, the DNA template comprises a T7 promoter sequence located immediately upstream of the sequence that corresponds to the targeting domain, and the 3' nucleotide of the T7 promoter sequence is not a guanine nucleotide. In certain embodiments, the 5' nucleotide of the targeting domain of the gRNA molecule is not a guanine nucleotide, the DNA template comprises a T7 promoter sequence located immediately upstream of the sequence that corresponds to the targeting domain, and the 3' nucleotide of the T7 promoter sequence is a guanine nucleotide which is downstream of a nucleotide other than a guanine nucleotide.

When a U6 promoter is used for in vivo transcription, these nucleotides may be the sequence UUUUUU. When an H1 promoter is used for transcription, these nucleotides may be the sequence UUUU. When alternate pol-III promoters are used, these nucleotides may be various numbers of uracil bases depending on, e.g., the termination signal of the pol-III promoter, or they may include alternate bases.

6.2. Methods for Designing gRNA Molecules

Methods for selecting, designing, and validating targeting domains for use in the gRNAs described herein are provided. Exemplary targeting domains for incorporation into gRNAs are also provided herein.

Methods for selection and validation of target sequences as well as off-target analyses have been described previously (see, e.g., *Mali* 2013; Hsu 2013; Fu 2014; Heigwer 2014; Bae 2014; Xiao 2014). For example, a software tool can be used to optimize the choice of potential targeting domains corresponding to a user's target sequence, e.g., to minimize total off-target activity across the genome. Off-target activity may be other than cleavage. For each possible targeting domain choice using *S. pyogenes* Cas9, the tool can identify all off-target sequences (preceding either NAG or NGG PAMs) across the genome that contain up to certain number (e.g., 1, 2, 3, 4, 5, 6, 7, 8, 9, or 10) of mismatched base-pairs. The cleavage efficiency at each off-target sequence can be predicted, e.g., using an experimentally-derived weighting scheme. Each possible targeting domain is then ranked according to its total predicted off-target cleavage; the top-ranked targeting domains represent those that are likely to have the greatest on-target cleavage and the least off-target cleavage. Other functions, e.g., automated reagent design for CRISPR construction, primer design for the on-target Surveyor assay, and primer design for high-throughput detection and quantification of off-target cleavage via next-gen sequencing, can also be included in the tool. Candidate targeting domains and gRNAs comprising those targeting domains can be functionally evaluated using methods known in the art and/or as set forth herein.

As a non-limiting example, targeting domains for use in gRNAs for use with *S. pyogenes* and *S. aureus* Cas9s were identified using a DNA sequence searching algorithm. 17-mer and 20-mer targeting domains were designed for *S. pyogenes* targets, while 18-mer, 19-mer, 20-mer, 21-mer, 22-mer, 23-mer, and 24-mer targeting domains were designed for *S. aureus* targets. gRNA design was carried out using custom gRNA design software based on the public tool cas-offinder (Bae 2014). This software scores guides after calculating their genome-wide off-target propensity. Typically matches ranging from perfect matches to 7 mismatches are considered for guides ranging in length from 17 to 24. Once the off-target sites are computationally determined, an aggregate score is calculated for each guide and summarized in a tabular output using a web-interface. In addition to identifying potential target sites adjacent to PAM sequences, the software also identifies all PAM adjacent sequences that differ by 1, 2, 3, or more than 3 nucleotides from the selected target sites. Genomic DNA sequences for each gene were obtained from the UCSC Genome browser and sequences were screened for repeat elements using the publically available RepeatMasker program. RepeatMasker searches input DNA sequences for repeated elements and regions of low complexity. The output is a detailed annotation of the repeats present in a given query sequence.

Targeting domains were identified for both single-gRNA nuclease cleavage and for a dual-gRNA paired "nickase" strategy. Criteria for selecting targeting domains and the determination of which targeting domains can be used for the dual-gRNA paired "nickase" strategy is based on two considerations:
 (1) Targeting domain pairs should be oriented on the DNA such that PAMs are facing out and cutting with the D10A Cas9 nickase can result in 5' overhangs; and
 (2) An assumption that cleaving with dual nickase pairs will result in deletion of the entire intervening sequence at a reasonable frequency. However, cleaving with dual nickase pairs can also result in indel mutations at the site of only one of the gRNAs. Candidate pair members can be tested for how efficiently they remove the entire sequence versus causing indel mutations at the target site of one targeting domain.

6.3 Exemplary gRNA Molecules

Exemplary targeting domains comprised in gRNA molecules for knocking out a HSV (e.g., HSV-1) UL19 gene, a HSV (e.g., HSV-1) UL30 gene, a HSV (e.g., HSV-1) UL48 gene, a HSV (e.g., HSV-1) UL54 gene, a HSV (e.g., HSV-1) RS1 gene, or a HSV (e.g., HSV-1) RL2 gene are provided in Table 1 below. Any of the targeting domains disclosed in Table 1 can be used with an *S. aureus* Cas9 molecule to generate a double stranded break (Cas9 nuclease) or a single-stranded break (Cas9 nickase). In certain embodiments, the *S. aureus* Cas9 molecule is a wild type *S. aureus* Cas9 molecule, which recognizes an NNGRRT (SEQ ID NO: 24) or NNGRRV (SEQ ID NO: 25) PAM. In certain embodiments, the *S. aureus* Cas9 molecule is a wild type *S. aureus* Cas9 molecule, which recognizes an NNGRRT (SEQ ID NO: 24) PAM.

TABLE 1

| Nucleotide sequence for the targeting domain of the gRNA molecule | The gene knocked out by the gRNA molecule |
|---|---|
| GCGUCAUCGACCUCGUCGGACU (SEQ ID NO: 1) | HSV-1 RS1 gene |
| GUCAUCGACCUCGUCGGACU (SEQ ID NO: 2) | HSV-1 RS1 gene |
| GGGCGCGGCGACAGGCGGUCCG (SEQ ID NO: 3) | HSV-1 RS1 gene |
| GCGCGGCGACAGGCGGUCCG (SEQ ID NO: 4) | HSV-1 RS1 gene |
| GACGGGCCUCCAUCCCGGGU (SEQ ID NO: 5) | HSV-1 UL19 gene |
| GCGAGGUCGUGAAGCUGGAAU (SEQ ID NO: 6) | HSV-1 UL48 gene |
| GACACGCACCGCCAGGAGUGU (SEQ ID NO: 7) | HSV-1 UL54 gene |
| GGAGUGUUCGAGUCGUGUCU (SEQ ID NO: 8) | HSV-1 UL54 gene |
| GGAGAGCCGCCGCGACGACC (SEQ ID NO: 9) | HSV-1 UL54 gene |
| GACCUGGAAUCGGACAGCAGCG (SEQ ID NO: 10) | HSV-1 UL54 gene |
| GCGACCGUCUCCUCUACCUC (SEQ ID NO: 11) | HSV-1 UL30 gene |
| GCCCCCCCGGCCCUGAGUCGGAGG (SEQ ID NO: 12) | HSV-1 RL2 gene |
| GUCUCUGUUGUUUGCAAGGGGG (SEQ ID NO: 13) | HSV-1 RL2 gene |
| CCUUGUGAAACAGUACGGCC (SEQ ID NO: 14) | HSV-1 UL30 gene |
| GUACGGCCCCGAGUUCGUGA (SEQ ID NO: 15) | HSV-1 UL30 gene |
| GAGGCCGCCGAGGACGUCAG (SEQ ID NO: 16) | HSV-1 RL2 gene |
| GCCCCUCCGGGGGGUUGGGGU (SEQ ID NO: 17) | HSV-1 RL2 gene |
| GGGGGGCGUCUGGCCCCUCCGG (SEQ ID NO: 18) | HSV-1 RL2 gene |
| UCGGGGCCGUACUGUUUCAC (SEQ ID NO: 19) | HSV-1 UL30 gene |
| GGUCCGUGCUGUCCGCCUCGGAGG (SEQ ID NO: 20) | HSV-1 RL2 gene |

TABLE 1-continued

| Nucleotide sequence for the targeting domain of the gRNA molecule | The gene knocked out by the gRNA molecule |
|---|---|
| GCCUGAUAGUGGGCGUGACGCCCA (SEQ ID NO: 21) | HSV-1 RL2 gene |
| GUCAUCGUCGUCGGCUCGAAAGGC (SEQ ID NO: 22) | HSV-1 RL2 gene |
| GCCCCGCUCGUCGCGGUCUGGGCU (SEQ ID NO: 23) | HSV-1 UL30 gene |

In certain embodiments, the gRNA comprises a targeting domain comprising a nucleotide sequence that is identical to, or differs by no more than 1 nucleotide, no more than 2 nucleotides, or no more than 3 nucleotides from, a nucleotide sequence selected from the group consisting of: SEQ ID NOS: 1-23. In certain embodiments, the gRNA comprises a targeting domain comprises a nucleotide sequence selected from the group consisting of: SEQ ID NOS: 1-23.

In certain embodiments, the gRNA comprises a targeting domain comprises a nucleotide sequence that is identical to, or differs by no more than 1 nucleotide, no more than 2 nucleotides, or no more than 3 nucleotides from, a nucleotide sequence selected from the group consisting of: SEQ ID NOS: 20-23. In certain embodiments, the gRNA comprises a targeting domain comprises a nucleotide sequence selected from the group consisting of: SEQ ID NOS: 20-23.

In certain embodiments, the gRNA comprises a targeting domain comprises a nucleotide sequence that is identical to, or differs by no more than 1 nucleotide, no more than 2 nucleotides, or no more than 3 nucleotides from, a nucleotide sequence selected from the group consisting of: SEQ ID NOS: 2, 6, 10, 15 and 16. In certain embodiments, the gRNA comprises a targeting domain comprises a nucleotide sequence selected from the group consisting of: SEQ ID NOS: 2, 6, 10, 15 and 16.

7. Genome Editing Systems Targeting HSV Viral Genes

Provided herein are genome editing systems (e.g., CRISPR/Cas9-based engineered systems) for use in altering one or more HSV viral gene, and in treating, preventing or reducing HSV infection. The genome editing systems are designed to target one or more HSV viral gene. The genome editing system (e.g., a CRISPR/Cas9 system) includes a gRNA molecule targeting a HSV viral gene (e.g., a UL19 gene (e.g., a HSV-1 UL19 gene), a UL30 gene (e.g., a HSV-1 UL30 gene, a UL48 gene (e.g., a HSV-1 UL48 gene), a UL54 gene (e.g., a HSV-1 UL54 gene), a RS1 gene (e.g., a HSV-1 RS1 gene), a RL2 gene (e.g., a HSV-1 RL2 gene), or a LAT gene (e.g., a HSV-1 LAT gene). The genome editing system can include two or more gRNA molecules, which target different DNA sequences.

7.1 CRISPR/Cas System Specific for a HSV Viral Gene

In certain embodiments, the genome editing system is a CRISPR/Cas9 system. "Clustered Regularly Interspaced Short Palindromic Repeats" and "CRISPRs", as used interchangeably herein, refers to loci containing multiple short direct repeats that are found in the genomes of approximately 40% of sequenced bacteria and 90% of sequenced archaea. The CRISPR system is a microbial nuclease system involved in defense against invading phages and plasmids that provides a form of acquired immunity. The CRISPR loci in microbial hosts contain a combination of CRISPR-associated (Cas) genes as well as non-coding RNA elements capable of programming the specificity of the CRISPR-mediated nucleic acid cleavage. Short segments of foreign DNA, called spacers, are incorporated into the genome between CRISPR repeats, and serve as a "memory" of past exposures. Cas9 forms a complex with the 3' end of the sgRNA, and the protein-RNA pair recognizes its genomic target by complementary base pairing between the 5' end of the sgRNA sequence and a predefined 20 bp DNA sequence, known as the protospacer. This complex is directed to homologous loci of pathogen DNA via regions encoded within the crRNA, i.e., the protospacers, and PAMs within the pathogen genome. The non-coding CRISPR array is transcribed and cleaved within direct repeats into short crRNAs containing individual spacer sequences, which direct Cas nucleases to the target site (protospacer). By simply exchanging the 20 bp recognition sequence of the expressed sgRNA, the Cas9 nuclease can be directed to new genomic targets. CRISPR spacers are used to recognize and silence exogenous genetic elements in a manner analogous to RNAi in eukaryotic organisms.

In certain embodiments, complementarity refers to a property shared between two nucleic acid sequences, such that when they are aligned antiparallel to each other, the nucleotide bases at each position will be complementary.

There are three known classes of CRISPR systems (Types I, II and III effector systems). The Type II effector system carries out targeted DNA double-strand break in four sequential steps, using a single effector enzyme, Cas9, to cleave dsDNA. Compared to the Type I and Type III effector systems, which require multiple distinct effectors acting as a complex, the Type II effector system may function in alternative contexts such as eukaryotic cells. The Type II effector system consists of a long pre-crRNA, which is transcribed from the spacer-containing CRISPR locus, the Cas9 protein, and a tracrRNA, which is involved in pre-crRNA processing. The tracrRNAs hybridize to the repeat regions separating the spacers of the pre-crRNA, thus initiating dsRNA cleavage by endogenous RNase III. This cleavage is followed by a second cleavage event within each spacer by Cas9, producing mature crRNAs that remain associated with the tracrRNA and Cas9, forming a Cas9:crRNA-tracrRNA complex.

The Cas9:crRNA-tracrRNA complex unwinds the DNA duplex and searches for sequences matching the crRNA to cleave. Target recognition occurs upon detection of complementarity between a "protospacer" sequence in the target DNA and the remaining spacer sequence in the crRNA. Cas9 mediates cleavage of target DNA if a correct PAM is also present at the 3' end of the protospacer. For protospacer targeting, the sequence must be immediately followed by the PAM, a short sequence recognized by the Cas9 nuclease that is required for DNA cleavage. Different Type II systems have differing PAM requirements. The *S. pyogenes* CRISPR system may have the PAM sequence for this Cas9 (SpCas9) as 5'-NRG-3', where R is either A or G, and characterized the specificity of this system in human cells. A unique capability of the CRISPR/Cas9 system is the straightforward ability to simultaneously target multiple distinct genomic loci by co-expressing a single Cas9 protein with two or more gRNAs. For example, the *S. pyogenes* Type II system naturally prefers to use an "NGG" sequence, where "N" can be any nucleotide, but also accepts other PAM sequences, such as "NAG" in engineered systems (Hsu et al, Nature Biotechnology (2013) doi: 10.1038/nbt.2647). A Cas9 molecule of *S. aureus* recognizes the sequence motif NNGRRT (SEQ ID NO: 24) or NNGRRV (SEQ ID NO: 25) (R=A or G) and directs cleavage of a target nucleic acid sequence 1 to 10, e.g., 3 to 5, bp upstream from that sequence. In certain embodiments, a Cas9 molecule of *S. aureus* recognizes the sequence motif NNGRRT (R=A or G) (SEQ ID NO: 24) and directs cleavage of a target nucleic acid sequence 1 to 10, e.g., 3 to 5, bp upstream from that sequence. In certain embodiments, a Cas9 molecule of *S. aureus* recognizes the sequence motif NNGRRV (R=A or G) (SEQ ID NO: 25) and directs cleavage of a target nucleic acid sequence 1 to 10, e.g., 3 to 5, bp upstream from that sequence. In the aforementioned embodiments, N can be any nucleotide residue, e.g., any of A, G, C, or T. Cas9 molecules can be engineered to alter the PAM specificity of the Cas9 molecule.

7.2 Cas9 Molecules

In certain embodiments, the genome editing system further comprises at least one Cas9 molecule (a Cas9 protein or Cas9 fusion protein) in addition to at least one gRNA molecule. The Cas9 fusion protein may, for example, include a domain that has a different activity that what is endogenous to Cas9, such as a transactivation domain.

The Cas9 protein can be from any bacterial or archaea species, including, but not limited to, *Streptococcus pyogenes* (*S. pyogenes*), *Staphylococcus aureus* (*S. aureus*), *Acidovorax avenae, Actinobacillus pleuropneumonias, Actinobacillus succinogenes, Actinobacillus suis, Actinomyces* sp., *cycliphilus denitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterosporus, Campylobacter coli, Campylobacter jejuni, Campylobacter lari, Candidatus Puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, gamma proteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus lugdunensis, Streptococcus* sp., *Subdoligranulum* sp., *Tistrella mobilis, Treponema* sp., or *Verminephrobacter eiseniae*.

In certain embodiments, the Cas9 molecule is an *S. pyogenes* Cas9 molecule. In certain embodiments, the Cas9 molecule is an *S. pyogenes* Cas9 variant.

In certain embodiments, the *S. pyogenes* Cas9 variant is an *S. pyogenes* Cas9 EQR variant. In certain embodiments, an *S. pyogenes* Cas9 EQR variant recognizes a PAM sequence selected from the group consisting of NGAG, NGCG, NGGG, NGTG, NGAA, NGAT and NGAC, and directs cleavage of a target nucleic acid sequence at 1 to 10, e.g., 3 to 5, base pairs upstream from that sequence. See Kleinstiver et al., *NATURE* 2015; 523(7561):481-5. In certain embodiments, an *S. pyogenes* Cas9 EQR variant recognizes a PAM sequence of NGAG and directs cleavage of a target nucleic acid sequence at 1 to 10, e.g., 3 to 5, base pairs upstream from that sequence. See Kleinstiver et al., *NATURE* 2015; 523(7561):481-5.

In certain embodiments, the *S. pyogenes* Cas9 variant is an *S. pyogenes* Cas9 VRER variant. In certain embodiments, a *S. pyogenes* Cas9 VRER variant recognizes a PAM sequence selected from the group consisting of NGCG, NGCA, NGCT, and NGCC and directs cleavage of a target nucleic acid sequence at 1 to 10, e.g., 3 to 5, base pairs upstream from that sequence. In certain embodiments, an *S. pyogenes* Cas9 VRER variant recognizes an NGCG PAM sequence and directs cleavage of a target nucleic acid sequence 1 to 10, e.g., 3 to 5, base pairs upstream from that sequence. See Kleinstiver Kleinstiver et al., *NATURE* 2015; 523(7561):481-5.

In certain embodiments, the Cas9 molecule is an *S. aureus* Cas9 molecule. In certain embodiments, the *S. aureus* Cas9 molecule recognizes a PAM sequence of NNGRR (R=A or G) (SEQ ID NO: 39) and directs cleavage of a target nucleic acid sequence 1 to 10, e.g., 3 to 5, bp upstream from that sequence. In certain embodiments, the *S. aureus* Cas9 molecule recognizes a PAM sequence of NNGRRN (R=A or G) (SEQ ID NO: 39) and directs cleavage of a target nucleic acid sequence 1 to 10, e.g., 3 to 5, bp upstream from that sequence. In certain embodiments, the *S. aureus* Cas9 molecule recognizes a PAM sequence of NNGRRT (R=A or G) (SEQ ID NO: 24) and directs cleavage of a target nucleic acid sequence 1 to 10, e.g., 3 to 5, bp upstream from that sequence. In certain embodiments, the *S. aureus* Cas9 molecule recognizes a PAM sequence of NNGRRV (R=A or G) (SEQ ID NO: 25) and directs cleavage of a target nucleic acid sequence 1 to 10, e.g., 3 to 5, bp upstream from that sequence.

In certain embodiments, the Cas9 molecule is an an enzymatically active Cas9 (eaCas9) molecule. An eaCas9 molecule or eaCas9 polypeptide is a Cas9 molecule or Cas9 polypeptide that is capable of cleaving a target nucleic acid molecule.

In certain embodiments, an eaCas9 molecule or eaCas9 polypeptide comprises one or more of the following enzymatic activities:

a nickase activity, i.e., the ability to cleave a single strand, e.g., the non-complementary strand or the complementary strand, of a nucleic acid molecule;

a double stranded nuclease activity, i.e., the ability to cleave both strands of a double stranded nucleic acid and create a double stranded break, which in certain embodiments is the presence of two nickase activities;

an endonuclease activity;

an exonuclease activity; and a helicase activity, i.e., the ability to unwind the helical structure of a double stranded nucleic acid.

In certain embodiments, an eaCas9 molecule or eaCas9 polypeptide cleaves both DNA strands and results in a double stranded break. In certain embodiments, an eaCas9 molecule or eaCas9 polypeptide cleaves only one strand, e.g., the strand to which the gRNA hybridizes to, or the strand complementary to the strand the gRNA hybridizes with. In certain embodiments, an eaCas9 molecule or eaCas9 polypeptide comprises cleavage activity associated with an HNH domain. In certain embodiments, an eaCas9 molecule or eaCas9 polypeptide comprises cleavage activity associated with a RuvC domain. In certain embodiments, an eaCas9 molecule or eaCas9 polypeptide comprises cleavage activity associated with an HNH domain and cleavage activity associated with a RuvC domain. In certain embodiments, an eaCas9 molecule or eaCas9 polypeptide comprises an active, or cleavage competent, HNH domain and an inactive, or cleavage incompetent, RuvC domain. In certain embodiments, an eaCas9 molecule or eaCas9 polypeptide comprises an inactive, or cleavage incompetent, HNH domain and an active, or cleavage competent, RuvC domain.

In certain embodiments, the Cas9 molecule is an enzymatically inactive Cas9 ("eiCas9") eiCas9 molecule or eiCas9 polypeptide. A eiCas9 molecule or eiCas9 polypeptide is a Cas9 molecule or polypeptide that has no or no substantial cleavage activity. Knockdown of one or more HSV viral gene can be mediated by an eiCas9 molecule or polypeptide.

Alternatively or additionally, the genome editing system (e.g., CRISPR/Cas9-based system) can include a fusion protein. The fusion protein can comprise two heterologous polypeptide domains, wherein the first polypeptide domain comprises a Cas protein and the second polypeptide domain has an activity such as transcription activation activity, transcription repression activity, transcription release factor activity, histone modification activity, nuclease activity, nucleic acid association activity, methylase activity, or demethylase activity. The fusion protein can include a Cas9 protein or a mutated/engineered Cas9 protein, fused to a second polypeptide domain that has an activity such as transcription activation activity, transcription repression activity, transcription release factor activity, histone modification activity, nuclease activity, nucleic acid association activity, methylase activity, or demethylase activity.

A Cas9 molecule or a Cas9 fusion protein can interact with one or more gRNA molecule and, in concert with the gRNA molecule(s), localizes to a site which comprises a target domain, and in certain embodiments, a PAM sequence. The ability of a Cas9 molecule or a Cas9 fusion protein to recognize a PAM sequence can be determined, e.g., using a transformation assay as described previously (Jinek et al., SCIENCE 2012; 337(6096):816-821).

In certain embodiments, the ability of a Cas9 molecule or a Cas9 fusion protein to interact with and cleave a target nucleic acid is PAM sequence dependent. A PAM sequence is a sequence in the target nucleic acid. In certain embodiments, cleavage of the target nucleic acid occurs upstream from the PAM sequence. Cas9 molecules from different bacterial species can recognize different sequence motifs (e.g., PAM sequences).

In certain embodiments, the at least one Cas9 molecule is an S. pyogenes Cas9 molecule. In certain embodiments, an S. pyogenes Cas9 molecule recognizes a PAM sequence of NGG and directs cleavage of a target nucleic acid sequence 1 to 10, e.g., 3 to 5, bp upstream from that sequence (see, e.g., Mali 2013).

In certain embodiments, the at least one Cas9 molecule is an S. aureus Cas9 molecule. In certain embodiments, an S. aureus Cas9 molecule recognizes the PAM sequence of NNGRRT (R=A or G) (SEQ ID NO: 24) and directs cleavage of a target nucleic acid sequence 1 to 10, e.g., 3 to 5, bp upstream from that sequence. In certain embodiments, an S. aureus Cas9 molecule recognizes a PAM sequence of NNGRRV (R=A or G) (SEQ ID NO: 25) and directs cleavage of a target nucleic acid sequence 1 to 10, e.g., 3 to 5, bp upstream from that sequence. In the aforementioned embodiments, N can be any nucleotide residue, e.g., any of A, G, C, or T. Cas9 molecules can be engineered to alter the PAM specificity of the Cas9 molecule.

In certain embodiments, the at least one Cas9 molecule is a mutant Cas9 molecule. Exemplary mutations with reference to the S. pyogenes Cas9 sequence include: D10A, E762A, H840A, N854A, N863A and/or D986A. Exemplary mutations with reference to the S. aureus Cas9 sequence include D10A and N580A. In certain embodiments, the Cas9 molecule is a mutant S. aureus Cas9 molecule. In certain embodiments, the mutant S. aureus Cas9 molecule comprises a D10A mutation. The nucleotide sequence encoding this mutant S. aureus Cas9 is set forth in SEQ ID NO: 26.

In certain embodiments, the mutant S. aureus Cas9 molecule comprises a N580A mutation. The nucleotide sequence encoding this mutant S. aureus Cas9 molecule is set forth in SEQ ID NO: 27.

A nucleic acid encoding a Cas9 molecule can be a synthetic nucleic acid sequence. For example, the synthetic nucleic acid molecule can be chemically modified. The synthetic nucleic acid sequence can be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein.

Additionally or alternatively, a nucleic acid encoding a Cas9 molecule or Cas9 polypeptide may comprise a nuclear localization sequence (NLS). Nuclear localization sequences are known in the art.

An exemplary codon optimized nucleic acid sequence encoding a Cas9 molecule of S. pyogenes is set forth in SEQ ID NO: 28. The corresponding amino acid sequence of an S. pyogenes Cas9 molecule is set forth in SEQ ID NO: 29. In certain embodiments, the S. pyogenes Cas9 molecule is an S. pyogenes Cas9 variant. In certain embodiments, the S. pyogenes Cas9 variant is a EQR variant that has a sequence set forth in SEQ ID NO: 30. In certain embodiments, the S. pyogenes Cas9 variant is a VRER variant that has a sequence set forth in SEQ ID NO: 31.

Exemplary codon optimized nucleic acid sequences encoding an S. aureus Cas9 molecule are set forth in SEQ ID NOs: 32-36. An amino acid sequence of an S. aureus Cas9 molecule is set forth in SEQ ID NO: 37.

If any of the above Cas9 sequences are fused with a peptide or polypeptide at the C-terminus, it is understood that the stop codon can be removed.

8. Genetic Constructs for Genome Editing of HSV Viral Genes

The presently disclosed subject matter provides for genetic constructs for genome editing or genomic alteration of a HSV viral gene (e.g., a UL19 gene (e.g., a HSV-1 UL19 gene), a UL30 gene (e.g., a HSV-1 UL30 gene, a UL48 gene (e.g., a HSV-1 UL48 gene), a UL54 gene (e.g., a HSV-1 UL54 gene), a RS1 gene (e.g., a HSV-1 RS1 gene), a RL2 gene (e.g., a HSV-1 RL2 gene), or a LAT gene (e.g., a HSV-1 LAT gene)).

A presently disclosed genetic construct encodes a genome editing system (e.g., a CRISPR/Cas9 system) that comprises at least one Cas9 molecule or a Cas9 fusion protein and at least one gRNA molecule. The presently disclosed subject matter also provides for compositions comprising such genetic constructs. The genetic construct can be present in a cell as a functioning extrachromosomal molecule. The genetic construct can be a linear minichromosome including centromere, telomeres or plasmids or cosmids.

The genetic construct can be part of a genome of a recombinant viral vector, including recombinant lentivirus, recombinant adenovirus, and recombinant adenovirus associated virus. The genetic construct can be part of the genetic material in attenuated live microorganisms or recombinant microbial vectors which live in cells. The genetic constructs can comprise regulatory elements for gene expression of the coding sequences of the nucleic acid. The regulatory elements may be a promoter, an enhancer, an initiation codon, a stop codon, or a polyadenylation signal.

In certain embodiments, the genetic construct is a vector. The vector can be an Adeno-associated virus (AAV) vector, which encode at least one Cas9 molecule and at least one gRNA molecule; the vector is capable of expressing the at least one Cas9 molecule and the at least gRNA molecule, in the cell of a mammal. The vector can be a plasmid. The vectors can be used for in vivo gene therapy.

In certain embodiments, an AAV vector is a small virus belonging to the genus Dependovirus of the Parvoviridae family that infects humans and some other primate species.

Coding sequences can be optimized for stability and high levels of expression. In certain instances, codons are selected to reduce secondary structure formation of the RNA such as that formed due to intramolecular bonding.

The vector can further comprise an initiation codon, which can be upstream of the genome editing system (e.g., CRISPR/Cas9-based system), and a stop codon, which can be downstream of the genome editing system (e.g., CRISPR/Cas9-based system) or the site-specific nuclease coding sequence. The initiation and termination codon can be in frame with the genome editing system (e.g., CRISPR/Cas9-based system) or the site-specific nuclease coding sequence. The vector can also comprise a promoter that is operably linked to the genome editing system (e.g., CRISPR/Cas9-based system). The promoter operably linked to the genome editing system (e.g., CRISPR/Cas9-based system) can be a promoter from simian virus 40 (SV40) (e.g., SV40 early promoter, SV40 late promoter), bacteriophage T7 promoter, bacteriophage T3 promoter, SP6 promoter, lac operator-promoter, tac promoter, a mouse mammary tumor virus (MMTV) promoter, a human immunodeficiency virus (HIV) promoter (e.g., the bovine immunodeficiency virus (BIV) promoter), a long terminal repeat (LTR) promoter (e.g., RSV-LTR promoter), a Moloney virus promoter, an avian leukosis virus (ALV) promoter, a cytomegalovirus (CMV) promoter (e.g., the CMV immediate early (MIE) promoter), Epstein Barr virus (EBV) promoter, a Rous sarcoma virus (RSV) promoter, Elongation Factor-1α short (EFS) promoter, EF-1a promoter, murine stem cell virus (MSCV) promoter, phosphoglycerate kinase (PGK) promoter, or a CAG promoter. The promoter can also be a promoter from a human gene such as human ubiquitin C (hUbC), human actin, human myosin, human hemoglobin, human muscle creatine, or human metalothionein.

The vector can also comprise a polyadenylation signal, which can be downstream of the genome editing system (e.g., CRISPR/Cas9-based system). The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector.

The vector can also comprise an enhancer upstream of the genome editing system (e.g., CRISPR/Cas9-based system) for DNA expression. The enhancer can be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector can also comprise a mammalian origin of replication in order to maintain the vector extrachromosomally and produce multiple copies of the vector in a cell. The vector can also comprise a regulatory sequence, which may be well suited for gene expression in a mammalian or human cell into which the vector is administered. The vector can also comprise a reporter gene, such as green fluorescent protein ("GFP") and/or a selectable marker, such as hygromycin ("Hygro").

The vectors can be expression vectors or systems to produce protein by routine techniques and readily available starting materials including Sambrook et al., Molecular Cloning and Laboratory Manual, Second Ed., Cold Spring Harbor (1989), which is incorporated fully by reference.

The presently disclosed genetic constructs (e.g., vectors) can be used for genome editing a HSV viral gene (e.g., a UL19 gene (e.g., a HSV-1 UL19 gene), a UL30 gene (e.g., a HSV-1 UL30 gene, a UL48 gene (e.g., a HSV-1 UL48 gene), a UL54 gene (e.g., a HSV-1 UL54 gene), a RS1 gene (e.g., a HSV-1 RS1 gene), a RL2 gene (e.g., a HSV-1 RL2 gene), or a LAT gene (e.g., a HSV-1 LAT gene)) in eye(s) of a subject.

9. Compositions

The presently disclosed subject matter provides for compositions comprising the above-described gRNA molecules or genetic constructs (e.g., vectors). The compositions can be in a pharmaceutical composition. The pharmaceutical compositions can be formulated according to the mode of administration to be used. In cases where pharmaceutical compositions are injectable pharmaceutical compositions, they are sterile, pyrogen free and particulate free. An isotonic formulation is preferably used. Generally, additives for isotonicity may include sodium chloride, dextrose, mannitol, sorbitol and lactose. In certain embodiments, isotonic solutions such as phosphate buffered saline are preferred. Stabilizers include gelatin and albumin. In certain embodiments, a vasoconstriction agent is added to the formulation.

The composition may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the composition for genome editing in skeletal muscle or cardiac muscle at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In certain embodiments, the DNA vector encoding the composition may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. 17.

10. Target Cells

The presently disclosed genome editing systems, genetic constructs (e.g., vectors) and compositions can be used to manipulate a cell, e.g., to edit a target nucleic acid, in a wide variety of cells.

In certain embodiments, a cell is manipulated by editing (e.g., introducing a mutation in) one or more HSV viral gene. In certain embodiments, the cell is infected with HSV-1 and/or HSV-2. In certain embodiments, the cell is from a subject having an HSV-1 and/or HSV-2 infection. In certain embodiments, the cell or subject has a latent HSV-1 and/or HSV-2 infection. In certain embodiments, the expression of one or more HSV viral genes is modulated, e.g., in vivo.

The presently disclosed genome editing systems, genetic constructs (e.g., vectors) and compositions can be delivered to a target cell. In certain embodiments, the target cell is an epithelial cell, e.g., an epithelial cell of the oropharynx (including, e.g., an epithelial cell of the nose, gums, lips, tongue or pharynx), an epithelial cell of the finger or fingernail bed, or an epithelial cell of the ano-genital area (including, e.g., an epithelial cell of the penis, scrotum, vulva, vagina, cervix, anus or thighs). In certain embodiments, the target cell is a neuronal cell, e.g., a cranial ganglion neuron (e.g. a trigeminal ganglion neuron, e.g., an oculomotor nerve ganglion neuron, e.g., an abducens nerve ganglion neuron, e.g., a trochlear nerve ganglion neuron), e.g. a cervical ganglion neuron, e.g., a sacral ganglion neuron, a sensory ganglion neuron, a cortical neuron, a cerebellar neuron or a hippocampal neuron. In certain embodiments, the target cell is an optic cell, e.g. an epithelial cell of the eye, e.g. an epithelial cell of the eyelid, e.g., a conjunctival cell, e.g., a conjunctival epithelial cell, e.g., a corneal keratocyte, e.g., a limbus cell, e.g., a corneal epithelial cell, e.g., a corneal stromal cell, e.g., a ciliary body cell, e.g., a scleral cell, e.g., a lens cell, e.g., a choroidal cell, e.g., a retinal cell, e.g., a rod photoreceptor cell, e.g., a cone photoreceptor cell, e.g., a retinal pigment epithelium cell, e.g., a horizontal cell, e.g., an amacrine cell, e.g., a ganglion cell.

11. Delivery, Formulations and Routes of Administration

Provided herein is a method for delivering a presently disclosed genome editing system, a presently disclosed genetic construct (e.g., a vector) or a composition comprising thereof to a cell or a tissue of a subject (e.g., a subject suffering from HSV infection). Upon delivery, the transfected cells can express the Cas9 molecule and the gRNA molecule. The genome editing systems, genetic constructs or compositions comprising thereof can be administered to a mammal to alter gene expression or to re-engineer or alter the genome. For example, the genome editing systems, genetic constructs or compositions comprising thereof can be administered to a mammal to alter a HSV viral gene (e.g., knock out a HSV viral gene) in a mammal. The mammal can be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

In certain embodiments, a presently disclosed genetic construct (e.g., a vector) or a composition comprising thereof is administered to a target cell (e.g., any of the target cells disclosed in Section 9) to genetically alter (e.g., knock out) a HSV viral gene (e.g., a HSV-1 viral gene). In certain embodiments, the cell is from a subject suffering from HSV infection (HSV-1 or HSV-2 infection).

The components (e.g., at least one Cas9 molecule and at least one gRNA molecule, optionally a donor template nucleic acid) of a presently disclosed genome editing system, composition or genetic construct can be delivered, formulated, or administered in a variety of forms, see, e.g., as those disclosed in Tables 2 and 3.

TABLE 2

| Elements | | | |
|---|---|---|---|
| Cas9 Molecule(s) | gRNA Molecule(s) | Donor Template Nucleic Acid | Comments |
| DNA | DNA | DNA | In certain embodiments, a Cas9 molecule and a gRNA are transcribed from DNA. In certain embodiments, they are encoded on separate molecules. In certain embodiments, the donor template is provided as a separate DNA molecule. |
| DNA | DNA | | In certain embodiments, a Cas9 molecule and a gRNA are transcribed from DNA. In certain embodiments, they are encoded on separate molecules. In certain embodiments, the donor template is provided on the same DNA molecule that encodes the gRNA. |
| | DNA | DNA | In certain embodiments, a Cas9 molecule and a gRNA are transcribed from DNA, here from a single molecule. In certain embodiments, the donor template is provided as a separate DNA molecule. |
| DNA | DNA | | In certain embodiments, a Cas9 molecule, and a gRNA are transcribed from DNA. In certain embodiments, they are encoded on separate molecules. In certain embodiments, the donor template is provided on the same DNA molecule that encodes the Cas9. |
| DNA | RNA | DNA | In certain embodiments, a Cas9 molecule is transcribed from DNA, and a gRNA is provided as in vitro transcribed or synthesized RNA. In certain embodiments, the donor template is provided as a separate DNA molecule. |
| DNA | RNA | | In certain embodiments, a Cas9 molecule is transcribed from DNA, and a gRNA is provided as in vitro transcribed or synthesized RNA. In certain embodiments, the donor template is provided on the same DNA molecule that encodes the Cas9. |

TABLE 2-continued

| Cas9 Molecule(s) | gRNA Molecule(s) | Donor Template Nucleic Acid | Comments |
|---|---|---|---|
| mRNA | RNA | DNA | In certain embodiments, a Cas9 molecule is translated from in vitro transcribed mRNA, and a gRNA is provided as in vitro transcribed or synthesized RNA. In certain embodiments, the donor template is provided as a DNA molecule. |
| mRNA | DNA | DNA | In certain embodiments, a Cas9 molecule is translated from in vitro transcribed mRNA, and a gRNA is transcribed from DNA. In certain embodiments, the donor template is provided as a separate DNA molecule. |
| mRNA | DNA | | In certain embodiments, a Cas9 molecule (e.g., an eaCas9 or eiCas9 molecule) is translated from in vitro transcribed mRNA, and a gRNA is transcribed from DNA. In certain embodiments, the donor template is provided on the same DNA molecule that encodes the gRNA. |
| Protein | DNA | DNA | In certain embodiments, a Cas9 molecule is provided as a protein, and a gRNA is transcribed from DNA. In certain embodiments, the donor template is provided as a separate DNA molecule. |
| Protein | DNA | | In certain embodiments, a Cas9 molecule is provided as a protein, and a gRNA is transcribed from DNA. In certain embodiments, the donor template is provided on the same DNA molecule that encodes the gRNA. |
| Protein | RNA | DNA | In certain embodiments is provided as a protein, and a gRNA is provided as transcribed or synthesized RNA. This delivery method is referred to as "RNP delivery". In certain embodiments, the donor template is provided as a DNA molecule. |

TABLE 3

| | Delivery Vector/Mode | Delivery into Non-Dividing Cells | Duration of Expression | Genome Integration | Type of Molecule Delivered |
|---|---|---|---|---|---|
| | Physical (e.g., electroporation, particle gun, Calcium Phosphate transfection, cell compression or squeezing) | YES | Transient | NO | Nucleic Acids and Proteins |
| Viral | Retrovirus | NO | Stable | YES | RNA |
| | Lentivirus | YES | Stable | YES/NO with modifications | RNA |
| | Adenovirus | YES | Transient | NO | DNA |
| | Adeno-Associated Virus (AAV) | YES | Stable | NO | DNA |
| | Vaccinia Virus | YES | Very Transient | NO | DNA |
| | Herpes Simplex Virus | YES | Stable | NO | DNA |
| Non-Viral | Cationic Liposomes | YES | Transient | Depends on what is delivered | Nucleic Acids and Proteins |
| | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
| | Engineered Bacteriophages | YES | Transient | NO | Nucleic Acids |
| | Mammalian Virus-like Particles | YES | Transient | NO | Nucleic Acids |
| | Biological liposomes: Erythrocyte Ghosts and Exosomes | YES | Transient | NO | Nucleic Acids |

10.1 DNA-Based Delivery of a Cas9 Molecule and or One or More gRNA Molecule

Nucleic acid compositions encoding Cas9 molecules, gRNA molecules, a donor template nucleic acid, or any combination (e.g., two or all) thereof can be administered to subjects or delivered into cells by art-known methods or as described herein. For example, Cas9-encoding and/or gRNA-encoding DNA, as well as donor template nucleic acids can be delivered, e.g., by vectors (e.g., viral or non-viral vectors), non-vector based methods (e.g., using naked DNA or DNA complexes), or a combination thereof.

Nucleic acid compositions encoding Cas9 molecules and/or gRNA molecules can be conjugated to molecules (e.g., N-acetylgalactosamine) promoting uptake by the target cells (e.g., the target cells described herein). Donor template molecules can likewise be conjugated to molecules (e.g., N-acetylgalactosamine) promoting uptake by the target cells (e.g., the target cells described herein).

In certain embodiments, the Cas9- and/or gRNA-encoding DNA is delivered by a vector (e.g., viral vector/virus or plasmid).

Vectors can comprise a sequence that encodes a Cas9 molecule and/or a gRNA molecule, and/or a donor template with high homology to the region (e.g., target sequence) being targeted. In certain embodiments, the donor template comprises all or part of a target sequence. Exemplary donor templates are a repair template, e.g., a gene correction template, or a gene mutation template, e.g., point mutation (e.g., single nucleotide (nt) substitution) template). A vector can also comprise a sequence encoding a signal peptide (e.g., for nuclear localization, nucleolar localization, or mitochondrial localization), fused, e.g., to a Cas9 molecule sequence. For example, the vectors can comprise a nuclear localization sequence (e.g., from SV40) fused to the sequence encoding the Cas9 molecule.

One or more regulatory/control elements, e.g., promoters, enhancers, introns, polyadenylation signals, a Kozak consensus sequences, internal ribosome entry sites (IRES), a 2A sequence, and splice acceptor or donor can be included in the vectors. In certain embodiments, the promoter is recognized by RNA polymerase II (e.g., a CMV promoter). In other embodiments, the promoter is recognized by RNA polymerase III (e.g., a U6 promoter). In certain embodiments, the promoter is a regulated promoter (e.g., inducible promoter). In certain embodiments, the promoter is a constitutive promoter. In certain embodiments, the promoter is a tissue specific promoter. In certain embodiments, the promoter is a viral promoter. In certain embodiments, the promoter is a non-viral promoter.

In certain embodiments, the vector or delivery vehicle is a viral vector (e.g., for generation of recombinant viruses). In certain embodiments, the virus is a DNA virus (e.g., dsDNA or ssDNA virus). In certain embodiments, the virus is an RNA virus (e.g., an ssRNA virus). In certain embodiments, the virus infects dividing cells. In other embodiments, the virus infects non-dividing cells. Exemplary viral vectors/viruses include, e.g., retroviruses, lentiviruses, adenovirus, adeno-associated virus (AAV), vaccinia viruses, poxviruses, and herpes simplex viruses.

In certain embodiments, the virus infects dividing cells. In other embodiments, the virus infects non-dividing cells. In certain embodiments, the virus infects both dividing and non-dividing cells. In certain embodiments, the virus can integrate into the host genome. In certain embodiments, the virus is engineered to have reduced immunity, e.g., in human. In certain embodiments, the virus is replication-competent. In other embodiments, the virus is replication-defective, e.g., having one or more coding regions for the genes necessary for additional rounds of virion replication and/or packaging replaced with other genes or deleted. In certain embodiments, the virus causes transient expression of the Cas9 molecule or molecules and/or the gRNA molecule or molecules. In other embodiments, the virus causes long-lasting, e.g., at least 1 week, 2 weeks, 1 month, 2 months, 3 months, 6 months, 9 months, 1 year, 2 years, or permanent expression, of the Cas9 molecule or molecules and/or the gRNA molecule or molecules. The packaging capacity of the viruses may vary, e.g., from at least about 4 kb to at least about 30 kb, e.g., at least about 5 kb, 10 kb, 15 kb, 20 kb, 25 kb, 30 kb, 35 kb, 40 kb, 45 kb, or 50 kb.

In certain embodiments, the viral vector recognizes a specific cell type or tissue. For example, the viral vector can be pseudotyped with a different/alternative viral envelope glycoprotein; engineered with a cell type-specific receptor (e.g., genetic modification(s) of one or more viral envelope glycoproteins to incorporate a targeting ligand such as a peptide ligand, a single chain antibody, or a growth factor); and/or engineered to have a molecular bridge with dual specificities with one end recognizing a viral glycoprotein and the other end recognizing a moiety of the target cell surface (e.g., a ligand-receptor, monoclonal antibody, avidin-biotin and chemical conjugation).

Exemplary viral vectors/viruses include, e.g., retroviruses, lentiviruses, adenovirus, adeno-associated virus (AAV), vaccinia viruses, poxviruses, and herpes simplex viruses.

In certain embodiments, the Cas9- and/or gRNA-encoding sequence is delivered by a recombinant retrovirus. In certain embodiments, the retrovirus (e.g., Moloney murine leukemia virus) comprises a reverse transcriptase, e.g., that allows integration into the host genome. In certain embodiments, the retrovirus is replication-competent. In certain embodiments, the retrovirus is replication-defective, e.g., having one of more coding regions for the genes necessary for additional rounds of virion replication and packaging replaced with other genes, or deleted.

In certain embodiments, the Cas9- and/or gRNA-encoding nucleic acid sequence (optionally the donor template nucleic acid) is delivered by a recombinant lentivirus. For example, the lentivirus is replication-defective, e.g., does not comprise one or more genes required for viral replication.

In certain embodiments, the Cas9- and/or gRNA-encoding nucleic acid sequence (optionally the donor template nucleic acid) is delivered by a recombinant adenovirus. In certain embodiments, the adenovirus is engineered to have reduced immunity in human.

In certain embodiments, the Cas9- and/or gRNA-encoding nucleic acid sequence (optionally the donor template nucleic acid) is delivered by a recombinant AAV. In certain embodiments, the AAV does not incorporate its genome into that of a host cell, e.g., a target cell as describe herein. In certain embodiments, the AAV can incorporate at least part of its genome into that of a host cell, e.g., a target cell as described herein. In certain embodiments, the AAV is a self-complementary adeno-associated virus (scAAV), e.g., a scAAV that packages both strands which anneal together to form double stranded DNA. AAV serotypes that may be used in the disclosed methods, include AAV1, AAV2, modified AAV2 (e.g., modifications at Y444F, Y500F, Y730F and/or S662V), AAV3, modified AAV3 (e.g., modifications at Y705F, Y731F and/or T492V), AAV4, AAV5, AAV6, modified AAV6 (e.g., modifications at S663V and/or T492V), AAV8, AAV 8.2, AAV9, AAV rh10, and pseudotyped AAV, such as AAV2/8, AAV2/5 and AAV2/6 can also be used in the disclosed methods. In certain embodiments, an AAV capsid that can be used in the methods described herein is a capsid sequence from serotype AAV1, AAV2, AAV3, AAV4, AAV5, AAV6, AAV7, AAV8, AAV9, AAV.rh8, AAV.rh10, AAV.rh32/33, AAV.rh43, AAV.rh64R1, or AAV7m8.

In certain embodiments, the Cas9- and/or gRNA-encoding nucleic acid sequence (optionally the donor template nucleic acid) is delivered in a re-engineered AAV capsid, e.g., with about 50% or greater, e.g., about 60% or greater, about 70% or greater, about 80% or greater, about 90% or greater, or about 95% or greater, sequence homology with a capsid sequence from serotypes AAV1, AAV2, AAV3, AAV4, AAV5, AAV6, AAV7, AAV8, AAV9, AAV.rh8, AAV.rh10, AAV.rh32/33, AAV.rh43, or AAV.rh64R1.

In certain embodiments, the Cas9- and/or gRNA-encoding nucleic acid sequence (optionally the donor template nucleic acid) is delivered by a chimeric AAV capsid. Exemplary chimeric AAV capsids include, but are not limited to, AAV9i1, AAV2i8, AAV-DJ, AAV2G9, AAV2i8G9, or AAV8G9.

In certain embodiments, the AAV is a self-complementary adeno-associated virus (scAAV), e.g., a scAAV that packages both strands which anneal together to form double stranded DNA.

In certain embodiments, the Cas9- and/or gRNA-encoding DNA (optionally the donor template nucleic acid) is delivered by a hybrid virus, e.g., a hybrid of one or more of the viruses described herein. In certain embodiments, the hybrid virus is hybrid of an AAV (e.g., of any AAV serotype), with a Bocavirus, B19 virus, porcine AAV, goose AAV, feline AAV, canine AAV, or MVM.

A packaging cell is used to form a virus particle that is capable of infecting a target cell. Exemplary packaging cells include 293 cells, which can package adenovirus, and ψ2 or PA317 cells, which can package retrovirus. A viral vector used in gene therapy is usually generated by a producer cell line that packages a nucleic acid vector into a viral particle. The vector typically contains the minimal viral sequences required for packaging and subsequent integration into a host or target cell (if applicable), with other viral sequences being replaced by an expression cassette encoding the protein to be expressed, e.g., components for a Cas9 molecule, e.g., two Cas9 components. For example, an AAV vector used in gene therapy typically only possesses inverted terminal repeat (ITR) sequences from the AAV genome which are required for packaging and gene expression in the host or target cell. The missing viral functions can be supplied in trans by the packaging cell line and/or plasmid containing E2A, E4, and VA genes from adenovirus, and plasmid encoding Rep and Cap genes from AAV, as described in "Triple Transfection Protocol." Henceforth, the viral DNA is packaged in a cell line, which contains a helper plasmid encoding the other AAV genes, namely rep and cap, but lacking ITR sequences. In certain embodiments, the viral DNA is packaged in a producer cell line, which contains E1A and/or E1B genes from adenovirus. The cell line is also infected with adenovirus as a helper. The helper virus (e.g., adenovirus or HSV) or helper plasmid promotes replication of the AAV vector and expression of AAV genes from the helper plasmid with ITRs. The helper plasmid is not packaged in significant amounts due to a lack of ITR sequences. Contamination with adenovirus can be reduced by, e.g., heat treatment to which adenovirus is more sensitive than AAV.

In certain embodiments, the viral vector is capable of cell type and/or tissue type recognition. For example, the viral vector can be pseudotyped with a different/alternative viral envelope glycoprotein; engineered with a cell type-specific receptor (e.g., genetic modification of the viral envelope glycoproteins to incorporate targeting ligands such as peptide ligands, single chain antibodies, growth factors); and/or engineered to have a molecular bridge with dual specificities with one end recognizing a viral glycoprotein and the other end recognizing a moiety of the target cell surface (e.g., ligand-receptor, monoclonal antibody, avidin-biotin and chemical conjugation).

In certain embodiments, the viral vector achieves cell type specific expression. For example, a tissue-specific promoter can be constructed to restrict expression of the transgene (Cas9 and gRNA) to only the target cell. The specificity of the vector can also be mediated by microRNA-dependent control of transgene expression. In certain embodiments, the viral vector has increased efficiency of fusion of the viral vector and a target cell membrane. For example, a fusion protein such as fusion-competent hemagglutin (HA) can be incorporated to increase viral uptake into cells. In certain embodiments, the viral vector has the ability of nuclear localization. For example, a virus that requires the breakdown of the nuclear envelope (during cell division) and therefore can not infect a non-diving cell can be altered to incorporate a nuclear localization peptide in the matrix protein of the virus thereby enabling the transduction of non-proliferating cells.

In certain embodiments, the Cas9- and/or gRNA-encoding nucleic acid sequence is delivered by a non-vector based method (e.g., using naked DNA or DNA complexes). For example, the DNA can be delivered, e.g., by organically modified silica or silicate (Ormosil), electroporation, transient cell compression or squeezing (e.g., as described in Lee, et al, 2012, Nano Lett 12: 6322-27), gene gun, sonoporation, magnetofection, lipid-mediated transfection, dendrimers, inorganic nanoparticles, calcium phosphates, or a combination thereof.

In certain embodiments, delivery via electroporation comprises mixing the cells with the Cas9- and/or gRNA-encoding DNA in a cartridge, chamber or cuvette and applying one or more electrical impulses of defined duration and amplitude. In certain embodiments, delivery via electroporation is performed using a system in which cells are mixed with the Cas9- and/or gRNA-encoding DNA in a vessel connected to a device (e.g, a pump) which feeds the mixture into a cartridge, chamber or cuvette wherein one or more electrical impulses of defined duration and amplitude are applied, after which the cells are delivered to a second vessel.

In certain embodiments, the Cas9- and/or gRNA-encoding nucleic acid sequence is delivered by a combination of a vector and a non-vector based method. In certain embodiments, the donor template nucleic acid is delivered by a combination of a vector and a non-vector based method. For example, virosomes combine liposomes combined with an inactivated virus (e.g., HIV or influenza virus), which can result in more efficient gene transfer, e.g., in respiratory epithelial cells than either viral or liposomal methods alone.

In certain embodiments, the delivery vehicle is a non-viral vector. In certain embodiments, the non-viral vector is an inorganic nanoparticle. Exemplary inorganic nanoparticles include, e.g., magnetic nanoparticles (e.g., $Fe_3MnO_2$) and silica. The outer surface of the nanoparticle can be conjugated with a positively charged polymer (e.g., polyethylenimine, polylysine, polyserine) which allows for attachment (e.g., conjugation or entrapment) of payload. In certain embodiments, the non-viral vector is an organic nanoparticle (e.g., entrapment of the payload inside the nanoparticle). Exemplary organic nanoparticles include, e.g., SNALP liposomes that contain cationic lipids together with neutral helper lipids which are coated with polyethylene glycol (PEG) and protamine and nucleic acid complex coated with lipid coating.

Exemplary lipids for gene transfer are shown below in Table 4.

TABLE 4

Lipids Used for Gene Transfer

| Lipid | Abbreviation | Feature |
|---|---|---|
| 1,2-Dioleoyl-sn-glycero-3-phosphatidylcholine | DOPC | Helper |
| 1,2-Dioleoyl-sn-glycero-3-phosphatidylethanolamine | DOPE | Helper |
| Cholesterol | | Helper |
| N-[1-(2,3-Dioleyloxy)propyl]N,N,N-trimethylammonium chloride | DOTMA | Cationic |
| 1,2-Dioleoyloxy-3-trimethylammonium-propane | DOTAP | Cationic |
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |
| 1-(2,3-Dioleoyloxypropyl)-2,4,6-trimethylpyridinium | 2Oc | Cationic |
| 2,3-Dioleyloxy-N-[2(sperminecarboxamido-ethyl]-N,N-dimethyl-1-propanaminium trifluoroacetate | DOSPA | Cationic |
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3β-[N-(N',N'-Dimethylaminoethane)-carbamoyl]cholesterol | DC-Chol | Cationic |
| Bis-guanidium-tren-cholesterol | BGTC | Cationic |
| 1,3-Diodeoxy-2-(6-carboxy-spermyl)-propylamide | DOSPER | Cationic |
| Dimethyloctadecylammonium bromide | DDAB | Cationic |
| Dioctadecylamidoglicylspermidin | DSL | Cationic |
| rac-[(2,3-Dioctadecyloxypropyl)(2-hydroxyethyl)]-dimethylammonium chloride | CLIP-1 | Cationic |
| rac-[2(2,3-Dihexadecyloxypropyl-oxymethyloxy)ethyl]trimethylammonium bromide | CLIP-6 | Cationic |
| Ethyldimyristoylphosphatidylcholine | EDMPC | Cationic |
| 1,2-Distearyloxy-N,N-dimethyl-3-aminopropane | DSDMA | Cationic |
| 1,2-Dimyristoyl-trimethylammonium propane | DMTAP | Cationic |
| O,O'-Dimyristyl-N-lysyl aspartate | DMKE | Cationic |
| 1,2-Distearoyl-sn-glycero-3-ethylphosphocholine | DSEPC | Cationic |
| N-Palmitoyl D-erythro-sphingosyl carbamoyl-spermine | CCS | Cationic |
| N-t-Butyl-N0-tetradecyl-3-tetradecylaminopropionamidine | diC14-amidine | Cationic |
| Octadecenolyoxy[ethyl-2-heptadecenyl-3 hydroxyethyl] imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propylamino)-N-ditetradecylcarbamoylme-ethyl-acetamide | RPR209120 | Cationic |
| 1,2-dilinoleyloxy-3-dimethylaminopropane | DLinDMA | Cationic |
| 2,2-dilinoleyl-4-dimethylaminoethyl-[1,3]-dioxolane | DLin-KC2-DMA | Cationic |
| dilinoleyl-methyl-4-dimethylaminobutyrate | DLin-MC3-DMA | Cationic |

Exemplary polymers for gene transfer are shown below in Table 5.

TABLE 5

Polymers Used for Gene Transfer

| Polymer | Abbreviation |
|---|---|
| Poly(ethylene)glycol | PEG |
| Polyethylenimine | PEI |
| Dithiobis(succinimidylpropionate) | DSP |
| Dimethyl-3,3'-dithiobispropionimidate | DTBP |
| Poly(ethylene imine) biscarbamate | PEIC |
| Poly(L-lysine) | PLL |
| Histidine modified PLL | |
| Poly(N-vinylpyrrolidone) | PVP |
| Poly(propylenimine) | PPI |
| Poly(amidoamine) | PAMAM |
| Poly(amido ethylenimine) | SS-PAEI |
| Triethylenetetramine | TETA |
| Poly(β-aminoester) | |
| Poly(4-hydroxy-L-proline ester) | PHP |
| Poly(allylamine) | |
| Poly(α-[4-aminobutyl]-L-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly (2-(dimethylamino)ethyl methacrylate) | pDMAEMA |
| Poly(2-aminoethyl propylene phosphate) | PPE-EA |
| Chitosan | |
| Galactosylated chitosan | |
| N-Dodacylated chitosan | |
| Histone | |
| Collagen | |
| Dextran-spermine | D-SPM |

In certain embodiments, the vehicle has targeting modifications to increase target cell update of nanoparticles and liposomes, e.g., cell specific antigens, monoclonal antibodies, single chain antibodies, aptamers, polymers, sugars (e.g., N-acetylgalactosamine (GalNAc)), and cell penetrating peptides. In certain embodiments, the vehicle uses fusogenic and endosome-destabilizing peptides/polymers. In certain embodiments, the vehicle undergoes acid-triggered conformational changes (e.g., to accelerate endosomal escape of the cargo). In certain embodiments, a stimuli-cleavable polymer is used, e.g., for release in a cellular compartment. For example, disulfide-based cationic polymers that are cleaved in the reducing cellular environment can be used.

In certain embodiments, the delivery vehicle is a biological non-viral delivery vehicle. In certain embodiments, the vehicle is an attenuated bacterium (e.g., naturally or artificially engineered to be invasive but attenuated to prevent pathogenesis and expressing the transgene (e.g., *Listeria monocytogenes*, certain *Salmonella* strains, *Bifidobacterium longum*, and modified *Escherichia coli*), bacteria having nutritional and tissue-specific tropism to target specific tissues, bacteria having modified surface proteins to alter target tissue specificity). In certain embodiments, the vehicle is a genetically modified bacteriophage (e.g., engineered phages having large packaging capacity, less immunogenic, containing mammalian plasmid maintenance sequences and having incorporated targeting ligands). In certain embodiments, the vehicle is a mammalian virus-like particle. For example, modified viral particles can be generated (e.g., by purification of the "empty" particles followed by ex vivo assembly of the virus with the desired cargo). The vehicle can also be engineered to incorporate targeting ligands to alter target tissue specificity. In certain embodiments, the vehicle is a biological liposome. For example, the biological liposome is a phospholipid-based particle derived from human cells (e.g., erythrocyte ghosts, which are red blood cells broken down into spherical structures derived from the subject (e.g., tissue targeting can be achieved by attachment of various tissue or cell-specific ligands), or secretory exosomes-subject (i.e., patient) derived membrane-bound nanovesicle (30-100 nm) of endocytic origin (e.g., can be produced from various cell types and can therefore be taken up by cells without the need of for targeting ligands).

In certain embodiments, one or more nucleic acid molecules (e.g., DNA molecules) other than the components of a Cas system, e.g., the Cas9 molecule component or components and/or the gRNA molecule component or components described herein, are delivered. In certain embodiments, the nucleic acid molecule is delivered at the same time as one or more of the components of the Cas system are delivered. In certain embodiments, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Cas system are delivered. In certain embodiments, the nucleic acid molecule is delivered by a different means than one or more of the components of the Cas system, e.g., the Cas9 molecule component and/or the gRNA molecule component, are delivered. The nucleic acid molecule can be delivered by any of the delivery methods described herein. For example, the nucleic acid molecule can be delivered by a viral vector, e.g., an integration-deficient lentivirus, and the Cas9 molecule component or components and/or the gRNA molecule component or components can be delivered by electroporation, e.g., such that the toxicity caused by nucleic acids (e.g., DNAs) can be reduced. In certain embodiments, the nucleic acid molecule encodes a therapeutic protein, e.g., a protein described herein. In certain embodiments, the nucleic acid molecule encodes an RNA molecule, e.g., an RNA molecule described herein.

11.2 Delivery of a RNA Encoding a Cas9 Molecule

RNA encoding Cas9 molecules and/or gRNA molecules can be delivered into cells, e.g., target cells described in Section 9, by art-known methods or as described herein. For example, Cas9-encoding and/or gRNA-encoding RNA can be delivered, e.g., by microinjection, electroporation, transient cell compression or squeezing (e.g., as described in Lee, et al., 2012, Nano Lett 12: 6322-27), lipid-mediated transfection, peptide-mediated delivery, or a combination thereof. Cas9-encoding and/or gRNA-encoding RNA can be conjugated to molecules to promote uptake by the target cells (e.g., target cells described herein).

In certain embodiments, delivery via electroporation comprises mixing the cells with the RNA encoding Cas9 molecules and/or gRNA molecules with or without donor template nucleic acid molecules, in a cartridge, chamber or cuvette and applying one or more electrical impulses of defined duration and amplitude. In certain embodiments, delivery via electroporation is performed using a system in which cells are mixed with the RNA encoding Cas9 molecules and/or gRNA molecules with or without donor template nucleic acid molecules, in a vessel connected to a device (e.g., a pump) which feeds the mixture into a cartridge, chamber or cuvette wherein one or more electrical impulses of defined duration and amplitude are applied, after which the cells are delivered to a second vessel. Cas9-encoding and/or gRNA-encoding RNA can be conjugated to molecules to promote uptake by the target cells (e.g., target cells described herein).

11.3 Delivery of a Cas9 Molecule Protein

Cas9 molecules can be delivered into cells by art-known methods or as described herein. For example, Cas9 protein molecules can be delivered, e.g., by microinjection, electroporation, transient cell compression or squeezing (e.g., as described in Lee, et al, 2012, Nano Lett 12: 6322-27), lipid-mediated transfection, peptide-mediated delivery, or a combination thereof. Delivery can be accompanied by DNA encoding a gRNA or by a gRNA. Cas9 protein can be conjugated to molecules promoting uptake by the target cells (e.g., target cells described herein).

In certain embodiments, delivery via electroporation comprises mixing the cells with the Cas9 molecules and/or gRNA molecules with or without donor nucleic acid, in a cartridge, chamber or cuvette and applying one or more electrical impulses of defined duration and amplitude. In certain embodiments, delivery via electroporation is performed using a system in which cells are mixed with the Cas9 molecules and/or gRNA molecules in a vessel connected to a device (e.g., a pump) which feeds the mixture into a cartridge, chamber or cuvette wherein one or more electrical impulses of defined duration and amplitude are applied, after which the cells are delivered to a second vessel. Cas9-encoding and/or gRNA-encoding RNA can be conjugated to molecules to promote uptake by the target cells (e.g., target cells disclosed in Section 9).

11.4 RNP Delivery of Cas9 Molecule Protein and gRNA

In certain embodiments, the Cas9 molecule and gRNA molecule are delivered to target cells via Ribonucleoprotein (RNP) delivery. In certain embodiments, the Cas9 molecule is provided as a protein, and the gRNA molecule is provided as transcribed or synthesized RNA. The gRNA molecule can be generated by chemical synthesis. In certain embodiments, the gRNA molecule forms a RNP complex with the Cas9 molecule protein under suitable condition prior to delivery to the target cells. The RNP complex can be delivered to the target cells by any suitable methods known in the art, e.g., by electroporation, lipid-mediated transfection, protein or DNA-based shuttle, mechanical force, or hydraulic force. In certain embodiments, the RNP complex is delivered to the target cells by electroporation.

11.5 Route of Administration

Systemic modes of administration include oral and parenteral routes. Parenteral routes include, by way of example, intravenous, intrarterial, intraosseous, intramuscular, intradermal, subcutaneous, intranasal and intraperitoneal routes. Components administered systemically may be modified or formulated to target the components to epithelial or neuronal cells.

Local modes of administration include, by way of example, intrathecal, intraspinal, intra-cerebroventricular, and intraparenchymal (e.g., into the parenchyma of the brain or spinal cord).

In certain embodiments, local modes of administration include intra-parenchymal into the dorsal root ganglion at the level of the trigeminal nerve. In certain embodiments, local modes of administration include intra-parenchymal into the dorsal root ganglion at the level of the sacral ganglia. In certain embodiments, local modes of administration include intra-parenchymal into the dorsal root ganglion at the level of the lumbar ganglia. In certain embodiments, local modes of administration include intra-parenchymal into the dorsal root ganglion at the level of the thoracic ganglia. In certain embodiments, local modes of administration include intra-parenchymal into the dorsal root ganglion at the level of the cervical ganglia, e.g., superior cervical ganglion, e.g., middle cervical ganglion, e.g., inferior cervical ganglion. In certain embodiments, local modes of administration include intra-parenchymal into the dorsal root ganglion at the level of the cranial nerve ganglia, e.g. cranial nerve ganglia I-XII.

In certain embodiments, significantly smaller amounts of the components (compared with systemic approaches) may exert an effect when administered locally compared to when administered systemically (for example, intravenously).

Local modes of administration can reduce or eliminate the incidence of potentially toxic side effects that may occur when therapeutically effective amounts of a component are administered systemically.

In certain embodiments, components described herein are delivered to epithelial cells, e.g., epithelial cells of the oropharynx (including, e.g., epithelial cells of the nose, gums, lips, tongue or pharynx), epithelial cells of the finger or fingernail bed, or epithelial cells of the ano-genital area (including, e.g., epithelial cells of the penis, vulva, vagina or anus). In certain embodiments, components described herein are delivered to the eye (including, e.g., corneal epithelium, e.g., corneal stroma, e.g., epithelium of upper and lower eyelid, e.g., lens).

Administration may be provided as a periodic bolus or as continuous infusion from an internal reservoir or from an external reservoir (for example, from an intravenous bag). Components may be administered locally, for example, by continuous release from a sustained release drug delivery device.

Administration may be provided as continuous infusion from an internal reservoir (for example, from an implant disposed at an intra- or extra-ocular location (see, U.S. Pat. Nos. 5,443,505 and 5,766,242)) or from an external reservoir (for example, from an intravenous bag). Components may be administered locally, for example, by continuous release from a sustained release drug delivery device immobilized to an inner wall of the eye or via targeted transscleral controlled release into the choroid (see, for example, PCT/US00/00207, PCT/US02/14279, Ambati et al. (2000) Invest. Ophthalmol. Vis. Sci. 41:1181-1185, and Ambati et al. (2000) Invest. Ophthalmol. Vis. Sci. 41:1186-1191). A variety of devices suitable for administering components locally to the inside of the eye are known in the art. See, for example, U.S. Pat. Nos. 6,251,090, 6,299,895, 6,416,777, 6,413,540, and PCT/US00/28187.

In certain embodiments, components may be formulated to permit release over a prolonged period of time. A release system can include a matrix of a biodegradable material or a material which releases the incorporated components by diffusion. The components can be homogeneously or heterogeneously distributed within the release system. A variety of release systems may be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly(caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used for injection. Typically the microspheres are composed of a polymer of lactic acid and glycolic acid, which are structured to form hollow spheres. The spheres can be approximately 15-30 microns in diameter and can be loaded with components described herein.

11.6 Bi-Modal or Differential Delivery of Components

Separate delivery of the components of a Cas system, e.g., the Cas9 molecule component or components and the gRNA molecule component or components, and more particularly, delivery of the components by differing modes, can enhance performance, e.g., by improving tissue specificity and safety.

In certain embodiments, the Cas9 molecule or molecules and the gRNA molecule or molecules are delivered by different modes, or as sometimes referred to herein as differential modes. Different or differential modes, as used herein, refer modes of delivery that confer different pharmacodynamic or pharmacokinetic properties on the subject component molecule, e.g., a Cas9 molecule or gRNA molecule, a donor template nucleic acid. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., AAV or lentivirus, delivery.

By way of example, the components, e.g., a Cas9 molecule and a gRNA molecule, can be delivered by modes that differ in terms of resulting half-life or persistence of the delivered component within the body, or in a particular compartment, tissue or organ. In certain embodiments, a gRNA molecule can be delivered by such modes. The Cas9 molecule component can be delivered by a mode which results in less persistence or less exposure to the body or a particular compartment or tissue or organ. In certain embodiments, two Cas9 molecules can by delivered by modes that differ in terms of resulting half-life or persistence of the delivered component within the body, or in a particular compartment, tissue or organ. In certain embodiments, two or more gRNA molecules can by delivered by modes that differ in terms of resulting half-life or persistence of the delivered component within the body, or in a particular compartment, tissue or organ.

More generally, in certain embodiments, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component, in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In certain embodiments, the first pharmacodynamic or pharmacokinetic property, e.g., distribution, persistence or exposure, is more limited than the second pharmacodynamic or pharmacokinetic property.

In certain embodiments, the first mode of delivery is selected to optimize, e.g., minimize, a pharmacodynamic or pharmacokinetic property, e.g., distribution, persistence or exposure.

In certain embodiments, the second mode of delivery is selected to optimize, e.g., maximize, a pharmacodynamic or pharmacokinetic property, e.g., distribution, persistence or exposure.

In certain embodiments, the first mode of delivery comprises the use of a relatively persistent element, e.g., a nucleic acid, e.g., a plasmid or viral vector, e.g., an AAV or lentivirus. As such vectors are relatively persistent product transcribed from them would be relatively persistent.

In certain embodiments, the second mode of delivery comprises a relatively transient element, e.g., an RNA or protein.

In certain embodiments, the first component comprises gRNA, and the delivery mode is relatively persistent, e.g., the gRNA is transcribed from a plasmid or viral vector, e.g., an AAV or lentivirus. Transcription of these genes would be of little physiological consequence because the genes do not encode for a protein product, and the gRNAs are incapable of acting in isolation. The second component, a Cas9 molecule, is delivered in a transient manner, for example as mRNA or as protein, ensuring that the full Cas9 molecule/gRNA molecule complex is only present and active for a short period of time.

In certain embodiments, the second component, two Cas9 molecules, is delivered in a transient manner, for example as mRNA or as protein, ensuring that the full Cas9/gRNA complex is only present and active for a short period of time. In certain embodiments, the second components, two Cas9 molecules, are delivered at two separate time points, e.g. a first Cas9 molecule delivered at one time point and a second Cas9 molecule delivered at a second time point, for example as mRNA or as protein, ensuring that the full Cas9/gRNA complexes are only present and active for a short period of time.

Furthermore, the components can be delivered in different molecular form or with different delivery vectors that complement one another to enhance safety and tissue specificity.

Use of differential delivery modes can enhance performance, safety and efficacy. E.g., the likelihood of an eventual off-target modification can be reduced. Delivery of immunogenic components, e.g., Cas9 molecules, by less persistent modes can reduce immunogenicity, as peptides from the bacterially-derived Cas enzyme are displayed on the surface of the cell by MHC molecules. A two-part delivery system can alleviate these drawbacks.

Differential delivery modes can be used to deliver components to different, but overlapping target regions. The formation active complex is minimized outside the overlap of the target regions. Thus, in certain embodiments, a first component, e.g., a gRNA molecule is delivered by a first delivery mode that results in a first spatial, e.g., tissue, distribution. A second component, e.g., a Cas9 molecule is delivered by a second delivery mode that results in a second spatial, e.g., tissue, distribution. Two distinct second components, e.g., two distinct Cas9 molecules, are delivered by two distinct delivery modes that result in a second and third spatial, e.g., tissue, distribution. In certain embodiments, the first mode comprises a first element selected from a liposome, nanoparticle, e.g., polymeric nanoparticle, and a nucleic acid, e.g., viral vector. The second mode comprises a second element selected from the group. The third mode comprises a second element selected from the group. In certain embodiments, the first mode of delivery comprises a first targeting element, e.g., a cell specific receptor or an antibody, and the second mode of delivery does not include that element. In embodiment, the second mode of delivery comprises a second targeting element, e.g., a second cell specific receptor or second antibody. In embodiment, the third mode of delivery comprises a second targeting element, e.g., a second cell specific receptor or second antibody.

When the Cas9 molecule or molecules are delivered in a virus delivery vector, a liposome, or polymeric nanoparticle, there is the potential for delivery to and therapeutic activity in multiple tissues, when it may be desirable to only target a single tissue. A two-part delivery system can resolve this challenge and enhance tissue specificity. If the gRNA molecule or molecules and the Cas9 molecule or molecules are packaged in separated delivery vehicles with distinct but overlapping tissue tropism, the fully functional complex is only be formed in the tissue that is targeted by both vectors.

In certain embodiments, components designed to alter (e.g., introduce a mutation into RL2, LAT or RS1) in one target position are delivered prior to, concurrent with, or subsequent to components designed to alter (e.g., introduce a mutation into RL2, LAT, or RS1) a second target position.

11.7 Ex Vivo Delivery

In certain embodiments, each component of the genome editing system or genetic construct described in Table 2 are introduced into a cell which is then introduced into the subject, e.g., cells are removed from a subject, manipulated ex vivo and then introduced into the subject. Methods of introducing the components can include, e.g., any of the delivery methods described in Table 3.

EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The presently disclosed subject matter has multiple aspects, illustrated by the following non-limiting examples.

Example 1—Reduction of HSV-1 Infection in Cells Transfected by Plasmids Encoding a Cas9 Molecule and a Presently Disclosed gRNA Molecule 24 plasmids (see Table 6), each of which encodes a wild-type *S. aureus* Cas9 molecule and one gRNA molecule targeting one HSV-1 viral gene were made.

TABLE 6

| Plasmid Name | gRNA sequence | Nt length | The gene targeted by the gRNA molecule |
|---|---|---|---|
| pAF002 (control) | GAUAUUUCCUUGUAACUAGU (SEQ ID NO: 38) | 20 | A non-HSV viral gene |
| pAF060 | GCGUCAUCGACCUCGUCGGACU (SEQ ID NO: 1) | 22 | HSV-1 RS1 gene |
| pAF061 | GUCAUCGACCUCGUCGGACU (SEQ ID NO: 2) | 20 | HSV-1 RS1 gene |
| pAF062 | GGGCGCGGCGACAGGCGGUCCG (SEQ ID NO: 3) | 22 | HSV-1 RS1 gene |
| pAF063 | GCGCGGCGACAGGCGGUCCG (SEQ ID NO: 4) | 20 | HSV-1 RS1 gene |
| pAF064 | GACGGGCCUCCAUCCCGGGU (SEQ ID NO: 5) | 20 | HSV-1 UL19 gene |
| pAF065 | GCGAGGUCGUGAAGCUGGAAU (SEQ ID NO: 6) | 21 | HSV-1 UL48 gene |
| pAF066 | GACACGCACCGCCAGGAGUGU (SEQ ID NO: 7) | 21 | HSV-1 UL54 gene |
| pAF067 | GGAGUGUUCGAGUCGUGUCU (SEQ ID NO: 8) | 20 | HSV-1 UL54 gene |
| pAF068 | GGAGAGCCGCCGCGACGACC (SEQ ID NO: 9) | 20 | HSV-1 UL54 gene |
| pAF069 | GACCUGGAAUCGGACAGCAGCG (SEQ ID NO: 10) | 22 | HSV-1 UL54 gene |
| pAF070 | GCGACCGUCUCCUCUACCUC (SEQ ID NO: 11) | 20 | HSV-1 UL30 gene |
| pAF071 | GCCCCCCCGGCCCUGAGUCGGAGG (SEQ ID NO: 12) | 24 | HSV-1 RL2 gene |
| pAF072 | GUCUCUGUUGUUUGCAAGGGGG (SEQ ID NO: 13) | 22 | HSV-1 RL2 gene |
| pAF073 | CCUUGUGAAACAGUACGGCC (SEQ ID NO: 14) | 20 | HSV-1 UL30 gene |
| pAF074 | GUACGGCCCCGAGUUCGUGA (SEQ ID NO: 15) | 20 | HSV-1 UL30 gene |
| pAF190 | GAGGCCGCCGAGGACGUCAG (SEQ ID NO: 16) | 24 | HSV-1 RL2 gene |
| pAF191 | GCCCCUCCGGGGGGUUGGGGU (SEQ ID NO: 17) | 24 | HSV-1 RL2 gene |
| pAF192 | GGGGGGCGUCUGGCCCCUCCGG (SEQ ID NO: 18) | 24 | HSV-1 RL2 gene |
| pAF193 | UCGGGGCCGUACUGUUUCAC (SEQ ID NO: 19) | 24 | HSV-1 UL30 gene |
| pAF075 | GGUCCGUGCUGUCCGCCUCGGAGG (SEQ ID NO: 20) | 20 | HSV-1 RL2 gene |
| pAF076 | GCCUGAUAGUGGGCGUGACGCCCA (SEQ ID NO: 21) | 22 | HSV-1 RL2 gene |
| pAF077 | GUCAUCGUCGUCGGCUCGAAAGGC (SEQ ID NO: 22) | 22 | HSV-1 RL2 gene |
| pAF078 | GCCCCGCUCGUCGCGGUCUGGGCU (SEQ ID NO: 23) | 20 | HSV-1 UL30 gene |

All 24 plasmids were transfected into HEK293T cells. The transfected HEK293T cells were challenged with lytic HSV-1 viruses and assayed by qPCR for HSV-1 viral genomes. In particular, on Day 0, a multi-well plate with seeded HEK293T cells was transfected with the plasmids including one for the expression of S. aureus Cas9, one for the expression of different HSV-1 targeting gRNAs, and one for the expression of Blasticidin resistance, e.g., those listed in Table 6. On Day 2, cells were challenged with Blasticidin to kill off any that had failed to be transfected. On Day 5, cells were infected with HSV-1 viruses at a dose of 0.1 MOI (Multiplicity of Infection). On Day 6, cells were removed from the plate and the DNA was harvested with Qiagen's DNeasy kit. SYBR-green qPCR was run on DNA samples using primers specific for HSV-1 genome and for actin.

As shown in FIG. 1, the qPCR results illustrate knockdown or reduction of HSV-1 replication in some plasmids but not all tested plasmids.

It is understood that the foregoing detailed description and accompanying examples are merely illustrative and are not to be taken as limitations upon the scope of the presently disclosed subject matter, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the presently disclosed subject matter, may be made without departing from the spirit and scope thereof.

What is claimed is:

1. A vector encoding a guide RNA (gRNA) molecule and a Cas9 molecule, wherein the gRNA molecule comprises a targeting domain comprising the nucleotide sequence set forth in SEQ ID NO: 21 or SEQ ID NO: 23.

2. The vector of claim 1, wherein the vector is configured to alter an HSV viral gene selected from the group consisting of a UL30 gene and a RL2 gene.

3. The vector of claim 1, wherein the Cas9 molecule is an *S. aureus* Cas9 molecule.

4. The vector of claim 1, wherein the Cas9 molecule recognizes a Protospacer Adjacent Motif (PAM) of either NNGRRT (SEQ ID NO: 24) or NNGRRV (SEQ ID NO: 25).

5. The vector of claim 1, wherein the vector is a viral vector.

6. A composition comprising the vector of claim 1.

7. A genome editing system comprising:
(a) a gRNA molecule comprising a targeting domain that comprises the nucleotide sequence set forth in SEQ ID NO: 21 or SEQ ID NO: 23; and
(b) a Cas9 molecule.

8. The genome editing system of claim 7, wherein the genome editing system is configured to alter an HSV viral gene selected from the group consisting of a UL30 gene and a RL2 gene.

9. The genome editing system of claim 7, wherein the Cas9 molecule is an *S. aureus* Cas9 molecule.

10. The genome editing system of claim 7, wherein the Cas9 molecule recognizes a PAM of either NNGRRT (SEQ ID NO: 24) or NNGRRV (SEQ ID NO: 25).

11. An isolated cell comprising the vector of claim 1.

12. An isolated cell comprising the genome editing system of claim 7.

13. A method of reducing HSV infection in a cell, comprising administering to the cell:
(a) a vector encoding a gRNA molecule and a Cas9 molecule; or
(b) a genome editing system comprising a gRNA molecule and a Cas9 molecule;
wherein the gRNA molecule comprises a targeting domain comprising the nucleotide sequence set forth in SEQ ID NO: 21 or SEQ ID NO: 23.

14. The method of claim 13, wherein the cell is infected with HSV.

15. The method of claim 13, wherein the HSV infection is HSV-1 infection.

16. The method of claim 13, wherein the cell is selected from the group consisting of an epithelial cell, a neuronal cell and an optic cell.

* * * * *